(12) United States Patent
De Souza et al.

(10) Patent No.: US 6,608,078 B2
(45) Date of Patent: Aug. 19, 2003

(54) ANTIBACTERIAL CHIRAL 8-(SUBSTITUTED PIPERIDINO)-BENZO [I,J] QUINOLIZINES, PROCESSES, COMPOSITIONS AND METHODS OF TREATMENT

(75) Inventors: Noel John De Souza, Mumbai (IN); Mahesh Vithalbhai Patel, Aurangabad (IN); Shiv Kumar Agarwal, Aurangabad (IN); Shirkant V Gupte, Aurangabad (IN); Dilip J Upadhyay, Mumbai (IN); Satish B Bhawsar, Aurangabad (IN); Mohammad A Jafri, Uttar Pradesh (IN)

(73) Assignee: Wockhardt Limited, Mumbai (IN)

( * ) Notice: Subject to any disclaimer, the term of this patent is extended or adjusted under 35 U.S.C. 154(b) by 0 days.

(21) Appl. No.: 09/850,669

(22) Filed: May 7, 2001

(65) Prior Publication Data

US 2002/0165227 A1 Nov. 7, 2002

Related U.S. Application Data

(60) Provisional application No. 60/202,459, filed on May 8, 2000.

(51) Int. Cl.$^7$ ..................... A61K 31/4375; A61P 31/04; C07D 455/06

(52) U.S. Cl. ................. 514/294; 514/228.5; 514/233.2; 514/253.03; 544/60; 544/126; 544/360; 546/94

(58) Field of Search ............................ 546/94; 514/294, 514/228.5, 233.2, 253.03; 544/60, 126, 360

(56) References Cited

U.S. PATENT DOCUMENTS

| | | | |
|---|---|---|---|
| 3,924,042 A | 12/1975 | Gerster et al. | 424/258 |
| 3,984,403 A | 10/1976 | Fujisawa et al. | 260/243.3 |
| 3,985,882 A | 10/1976 | Gerster | 424/258 |
| 4,051,247 A | 9/1977 | Schuppan et al. | 424/258 |
| 4,382,892 A | 5/1983 | Hayakawa et al. | 260/243.3 |
| 4,399,134 A * | 8/1983 | Ishikawa et al. | 514/228.2 |
| 4,404,207 A | 9/1983 | Stern et al. | 424/258 |
| 4,416,884 A | 11/1983 | Ishikawa et al. | 424/250 |
| 4,443,447 A | 4/1984 | Gerster et al. | 424/248.53 |
| 4,472,406 A | 9/1984 | Gerster et al. | 424/258 |
| 4,472,407 A | 9/1984 | Stern et al. | 424/258 |
| 4,535,161 A | 8/1985 | Hayakawa et al. | 546/94 |
| 4,552,879 A | 11/1985 | Ishikawa et al. | 514/253 |
| 4,594,347 A | 6/1986 | Ishikawa et al. | 514/252 |
| 4,599,418 A | 7/1986 | Irikura et al. | 544/361 |
| 4,642,355 A | 2/1987 | Nakamura et al. | 548/533 |
| 4,777,175 A | 10/1988 | Culbertson et al. | 514/300 |
| 4,874,764 A | 10/1989 | Ueda et al. | 514/254 |
| 4,894,458 A | 1/1990 | Masuzawa et al. | 546/156 |
| 4,935,420 A | 6/1990 | Ueda et al. | 514/235.2 |
| 5,051,509 A | 9/1991 | Nagano et al. | 546/156 |
| 5,185,337 A | 2/1993 | Fujii et al. | 514/254 |
| 5,607,942 A | 3/1997 | Petersen et al. | 546/200 |
| 5,639,886 A | 6/1997 | Zerbes et al. | 546/155 |
| 5,677,316 A | 10/1997 | Ao et al. | 514/312 |
| 5,859,026 A | 1/1999 | Ito et al. | 514/312 |
| 5,869,661 A | 2/1999 | Ochi et al. | 544/128 |
| 5,889,009 A | 3/1999 | Miyake et al. | 514/254 |
| 6,034,100 A | 3/2000 | Adachi et al. | 514/312 |
| 6,121,285 A | 9/2000 | Takemura et al. | 514/312 |
| 6,184,388 B1 | 2/2001 | Takemura et al. | 548/566 |
| 6,329,391 B1 | 12/2001 | Ledoussal et al. | 514/312 |

FOREIGN PATENT DOCUMENTS

| | | |
|---|---|---|
| EP | 0241206 | 1/1987 |
| EP | 0230295 | 7/1987 |
| EP | 0287951 | 4/1988 |
| EP | 0304087 | 8/1988 |
| EP | 0342675 | 11/1989 |
| EP | 0394553 | 11/1989 |
| EP | 0541086 | 5/1993 |
| EP | 0572259 | 5/1993 |
| EP | 0908181 | 4/1999 |
| EP | 0919553 | 6/1999 |
| JP | 57081486 | 5/1982 |
| JP | 57176987 | 10/1982 |
| JP | 58090511 | 5/1983 |
| JP | 63192753 | 8/1988 |
| JP | 02131483 | 5/1990 |
| JP | 02188570 | 7/1990 |
| JP | 02188589 | 7/1990 |
| JP | 05339238 | 12/1993 |
| WO | 9420105 | 9/1994 |
| WO | 9731000 | 8/1997 |

(List continued on next page.)

OTHER PUBLICATIONS

Oizumi, N., et al. "Relationship between mutations in the DNA gyrase and topoisomerase IV genes and nadifloxacin . . . *Staphylococcus aureus*" *J. Infect Chemotherapy*, vol. 7, p. 191–194, (2001).

(List continued on next page.)

*Primary Examiner*—Evelyn Mei Huang
(74) *Attorney, Agent, or Firm*—Ladas & Parry

(57) ABSTRACT

The present invention relates to optically pure 8-(substituted piperidino)-benzo[i,j]quinolizines, their isomers, derivatives, salts, pseudopolymorphs, polymorphs prodrugs and hydrates thereof, to processes for their preparation, and to pharmaceutical compositions comprising 8-(substituted piperidino)-benzo[i,j]quinolizines their isomers, derivatives, salts, pseudopolymorphs, polymorphs and hydrates thereof. These compounds and compositions possess potent activity in treating local and systemic infections, particularly infections caused by sensitive and resistant Gram-positive organism infections, Gram-negative organism infections, mycobacterial infections and nosocomial pathogens, and particularly those belonging to the staphylococcus, streptococcus and enterococcus groups. Methods for treating the diseases and disorders arising from the foregoing infections in humans and animals are described by administering the compounds of the invention to said humans and animals.

15 Claims, No Drawings

FOREIGN PATENT DOCUMENTS

| WO | 9744034 | 11/1997 |
|----|---------|---------|
| WO | 9914214 | 9/1998 |
| WO | 9926940 | 6/1999 |
| WO | 0018404 | 4/2000 |
| WO | 0068229 | 11/2000 |
| WO | 0185095 | 11/2001 |
| WO | 0185728 | 11/2001 |
| WO | 0209758 | 2/2002 |

OTHER PUBLICATIONS

Haustein, U–F., et al. "Topical quinolone nadifloxacin (OPC–7251) in bacterial skin disease: clinical evaluation ... testing" *J. of Dermatological Treatment*, vol. 8, p. 87–92, (1997).

Mergler et al. Proceedings of the 12$^{th}$ American Peptide Symposium. Reference cited on p. 2 of EPA 0953577.

Alsina, et al. *Tetrahedon Letters*, v38 n5, (1997) 883–886.

Edwards et al. *J. Med. Chem.*, v37 n22 (1994) 3749–3757.

Ince, Dilek et al. *Antimicrobial Agents and Chemotherapy*, (Dec. 2000), 44(12) pp3344–3350.

Oizumi, Nbuyuki et al. *J. Infect. Chemother.*, (2001) 7: 191–194.

Bundgaard, H. *Design of Prodrugs*. (1985) p1–3.

Hashimoto et al. *Chem. Pharm. Bull.* V44, n4 (1996) p642–645.

Irish, D. et al. *J. of Hospital Infection*, v39 (1998) p19–26.

Kido, M. et al. *Chem. Pharm. Bull.* V42, n4 (1994) p872–876.

Sloan et al. *Physics and Chemistry of the Organic Solid State*, eds. D. Fox, Labes and Weissberer, Interscience Publishers, (1963) 179–182.

Takahashi et al. *Arzheim–Forsc/Drug Res.*, 45(1), Nr.2 (1995), 199–197.

Morita, S. et al. *Tetrahedoni: Assymetry*, v6, n1 (1995) p245–254.

Morita, S. et al. *Chem. Pharm. Bull.*, 38(7) (1990) 2027–2029.

Ishikawa et al. *Chem. Pharm. Bull.*, 37(8) (1989) 2103–2108.

English translation of Yamada, H. et al. *Iyahukin Kenkyu*, v31, n8 (2000) p519–524.

English translation of Yamada, H. et al. *Iyahukin Kenkyu*, v31, n8 (2000) p525–528.

Berge et al. *J. of Pharmaceutical Sciences*, 66(1) (1977) 1–19.

Abstract of Koike, M. et al. *Iyakuhin Kenkyu*, v21, n5 (1990) p998–1021.

Abstract of Koike, M. et al. *Iyakuhin Kenkyu*, v21, n5 (1990) p1022–1033.

Abstract of Fujita, S. et al. *Iyakuhin Kenkyu*, v21, n6 (1990) p1156–1176.

Abstract of Koike, M. et al. *Yakubutsu Dotai*, v5, n2 (1990) p199–208.

Abstract of Yasuo, A.. et al. *Yakuri to Chiryo*, v18, n4 (1990) p1717–1730.

Abstract of Hayakawa, R. et al. *Hifu*, v32, n2 (1990) p217–230.

Abstract of Asada, Y. et al. *Yakuri to Chiryo*, v18, n4 (1990) p1717–1730.

Abstract of Awogi, T. et al. *Iyakuhin Kenkyu*, v21, n4 (1990) p626–635.

Abstract of Matsuzawa, A. et al. *Iyakuhin Kenkyu*, v21, n4 (1990) p636–646.

Abstract of Nagao T. et al. *Iyakuhin Kenkyu*, v21, n4 (1990) p647–662.

Abstract of Matsuzawa, A. et al. *Iyakuhin Kenkyu*, v21, n4 (1990) p633–670.

Abstract of Hashimoto, K.. et al. *Iyakuhin Kenkyu*, v21, n4 (1990) p670–677.

Abstract of Furukawa, M. et al. *Iyakuhin Kenkyu*, v21, n5 (1990) p989–997.

Abstract of Kojima, K. et al. *Iyakuhin Kenkyu*, v21, n5 (1990) p1034–1052.

Abstract of Nakagiri, N. et al. *Iyakuhin Kenkyu*, v21, n6 (1990) p1144–1155.

Abstract of Aoki, M. et al. *Iyakuhin Kenkyu*, v21, n6 (1990) p1177–1202.

Abstract of Matsuzawa, A. et al. *Iyakuhin Kenkyu*, v22, n1 (1990) p61–76.

Abstract of Kurokawa I. et al. *J. Am. Acad. Dermatol.*, v25, n4 (1991) p674–681.

Abstract of Bojar, R. et al. *J. of Investigative Dermatology*, v103, n3 (1994) p405.

Abstract of Haustein, U.F. et al. *J. of Dermatological Treatment*, v8, n2 (1997) p87–92.

Abstract of Smith, C.M. et al. *J. of Investigative Dermatology*, v108, n3 (1997) p123.

Abstract of Hayakawa, R. et al. *Hifu*, v40, n2 (1998) p165–171.

Fujio, N. et al. *Yakuri to Chiryo*, v26, n7 (1998) p1119–1132.

Kido, M. et al. *Chem. Pharm. Bull.*, v44, n2 (1996) p421–423.

Miller, M.A. et al. *Infection Control and Hospital Epidemiology*, v17, n12 (1995) p811–813.

Nishijima, S. et al. *The Journal of Int'l Medical Research*, v23, (1995) p328–334.

Nishijima, S. et al. *Journal of Dermatology*, v22, (1995) p153–155.

Nishijima, S. et al. *The Journal of Int'l Medical Research*, v24, (1996) p12–16.

Nishijima, S. et al. *Journal of Dermatology*, v21, (1994) p233–238.

Udo, E. E. et al. *J. of Hospital Infection*, v26, (1994) p157–165.

Abstract of Kurokawa, I. et al. *European J. of Dermatology*, v9, n1 (1999) p25–28.

Abstract of Komagata. et al. *Japanese Journal of Antibiotics*, v51, n2 (1998) p130–136.

Abstract of Gollnick, H. et al. *Dermatology*, v196, n1(1998) p119–125.

Abstract of Nishijima, S. et al. *J. of Int'l Medical Research*, v25, n4 (1997) p210–213.

Abstract of Nishijima, S. et al. *J. of In'tl Medical Research*, v24, n6 (1996) p473–477.

Abstract of Akamatsu, H. et al. *J. of Int'l Medical Research*, v23, n1 (1995) p19–26.

Abstract of Takahashi, N. et al. *Arzneimittel–Forschung*, v45, n2 (1995) p195–.

Abstract of Takahashi, N. et al. *Arzneimittal–Forschung*, v44, n11 (1994) 1p265–1268.

Abstract of Patel, M.V. 39$^{th}$ ICAAC at San Diego Poster No. F0558 (Sep. 26–29, 1999).

Chemical Abstract: Doc. No. 123:334723 Vogt, K. et al. *Drugs*, v49, Suppl.2 (1995).

Chemical Abstract: Doc. No. 123:334716 Nishijima et al. *Drugs*, v49, Suppl.2 (1995).

Chemical Abstract: Doc. No. 124:21098 Bojar, R.A. et al. *Drugs,* v49, Suppl.2 (1995).

Chemical Abstract: Doc. No. 122:213914, *Tetrahedon: Asymmetry,* v6, No. 1 (1995).

Chemical Abstract: Doc. No. 119:4810 Vogt, K. et al. *Eur. J. Clin. Microbiol. Infect.*

Chemical Abstract: Doc. No. 113:2131188 Morita, S. et al. *Chem. Pharm. Bull.* v38, n7.

Chemical Abstract: Doc. No. 112:229223, Muto, N. et al. *J. Immunoassay,* v11 n1.

Chemical Abstract: Doc. No.112: 191305, Koike, M. et al. *J. Chromatogr.* v526, n1.

Chemical Abstract: Doc. No. 112: 178631, Ishikawa, H. et al. *Chem. Pharm. Bull.* v37,.

Chemical Abstract: Doc. No. 112:52083, *Chemotherapy,* v37, n9 (1989) p1160–1178.

Abstract of Iwahara, K. et al. *European J. of Dermatology,* v9, n4 (1999) p276–277.

Abstract of Radl, S. et al. *Archiv der Pharmazie,* v329, n3 (1996) p115–119.

Abstract of Andriole, V.T., *Drugs,* v46, Suppl.3 (1993) p1–7.

Ball, Peter. "The Quinolones: History and Overview", Chapter 1, *The Quinolones,* Second Ed. Academic Press, 1998. p1–28.

Domagala, John M. *Journal of Antimicrobial Chemotherapy* (1994) 33, 685–706.

Suto, Mark J. et al. *J. of Med. Chem.* (1992) 35, 4745–4750.

Abstract of Yamakawa, T. et al. *J. Antimicrobial Chemotherapy,* 49(3) Mar. 2002, 455–465.

Hooper, David C. *Drug Resistance Updates* (1999) 2, 38–55.

Ince, Dilek and David C. Hooper. *Antimicrobial Agents and Chemotherapy* (Oct. 2001) 45(10), 2755–2764.

Fournier, Benedicte and David C. Hooper. *Antimicrobial Agents and Chemotherapy,* (Jan. 1998) 42(1) 121–128.

Zhao, Xilin et al. *Antimicrobial Agents and Chemotherapy,* (Apr. 1998) 42(4) p956–958.

Breines, David M. et al. *Antimicrobial Agents and Chemotherapy,* (Jan. 1997) 41(1) 175–179.

Fournier, Benedicte, et al. *Journal of Bacteriology,* (Feb. 2000) 182(3) 664–671.

Mandell, Lionel et al. *CIP* (2001) 32, Suppl 1, S72–S79.

Gootz, Thomas D. and Katherine E. Brighty. "Chemistry and Mechanism of Action of the Quinolone Antobacterials", *The Quinolones,* Second Ed. Chap 2. Academic Press (1998).

Takenouchi, Takashi et al. *Antomicrobial Agents and Chemotherapy,* (Aug. 1996) 40(8) p1835–1842.

Zhao, Xilin, et al. *Proc. Natl. Acad. Sci. USA,* (Dec. 1997) vol. 94, pp13991–13996.

Takei, Masaya et al. *Antimicrobial Agents and Chemotherapy,* (Dec. 2001), 45(12), pp3544–3547.

* cited by examiner

ANTIBACTERIAL CHIRAL 8-(SUBSTITUTED PIPERIDINO)-BENZO [I,J] QUINOLIZINES, PROCESSES, COMPOSITIONS AND METHODS OF TREATMENT

This application claims the priority of U.S. Patent Application No. 60/202,459 filed on May 8, 2000.

FIELD OF THE INVENTION

This invention relates to 8-(substituted piperidino)-benzo[i,j]quinolizines, to processes for their preparation and to pharmaceutical compositions comprising 8-(substituted piperidino)-benzo[i,j]quinolizines.

These compounds and compositions possess potent activity in treating local and systemic infections, particularly infections caused by sensitive and resistant Gram-positive organisms, Gram-negative organisms, mycobacteria and nosocomial pathogens, and particularly those belonging to the staphylococcus, streptococcus and enterococcus groups.

Also, disclosed are methods for treating the diseases and disorders arising from the foregoing infections in humans and animals by administering the compounds of the invention to said humans and animals.

BACKGROUND OF THE INVENTION

The active compounds of this invention are related to and derived from the fluoroquinolone antibiotic [(±)-9-fluoro-8-(4-hydroxypiperidin-1-yl)-5-methyl-6,7-dihydro-1-oxo-1H-5H-benzo[i,j]quinolizine-2-carboxylic acid disclosed in JP Patent No. 58,90,511 and U.S. Pat. No. 4,399,134. 9-fluoro-8-(4-hydroxypiperidin-1-yl)-5-methyl-6,7-dihydro-1-oxo-1H-5H-benzo[i,j]quinolizine-2-carboxylic acid has an asymmetric carbon atom at the 5-position thereof. RS-(±)-9-fluoro-8-(4-hydroxypiperidin-1-yl)-5-methyl-6,7-dihydro-1-oxo-1H-5H-benzo[i,j]quinolizine-2-carboxylic acid comprises two optically active isomers. In describing an optically active compound, the prefixes R and S or D and L are used to denote the absolute configuration of the molecule about its chiral centre(s). The prefixes (+) and (−) or d and l are employed to designate the sign of rotation of plane-polarized light by the compound, with (−) or l meaning that the compound is levorotatory. A compound prefixed with (+) or d is dextrorotatory. Compounds having a single chiral centre exist as a pair of enantiomers, which are identical except that they are non-superimposable mirror images of one another. A one-to-one mixture of enantiomers is often referred to as a racemic mixture. Racemic 9-fluoro-8-(4-hydroxypiperidin-1-yl)-5-methyl-6,7-dihydro-1-oxo-1H-5H-benzo[i,j]quinolizine-2-carboxylic acid is said to derive its biological activity primarily from the S-(−)-enantiomer. The optically active S-(−)-9-fluoro-8-(4-hydroxypiperidin-1-yl)-5-methyl-6,7-dihydro-1-oxo-1H-5H-benzo[i,j]quinolizine-2-carboxylic acid $[\alpha]^{20}_D=-312.0$ is obtained as disclosed in Chem. Pharm. Bull 44 (1996), page nos. 642–5 and Jpn. Kokai Tokyo Koho JP 63,192,753. The optically active R-(+)-9-fluoro-8-(4-hydroxypiperidin-1-yl)-5-methyl-6,7-dihydro-1-oxo-1H-5H-benzo[i,j] quinolizine-2-carboxylic acid, $[\alpha]^{20}_D=+312.0$, is obtained as disclosed in Jpn.Kokai Tokyo Koho JP 63,192,753. Pharmaceutical compositions of RS-(±)-9-fluoro-8-(4-hydroxypiperidin 1-yl)-5-methyl-6,7-dihydro-1-oxo-1H-5H-benzo[i,j]quinolizine-2-carboxylic acid are disclosed in U.S. Pat. No. 4,399,134 and U.S. Pat. No. 4,552,879.

To our knowledge no 9-fluoro-8-(4-hydroxypiperidin-1-yl)-5-methyl-6,7-dihydro-1-oxo-1H-5H-benzo[i,j]quinolizine-2-carboxylic acid derivatives are known in which the 8-(4-hydroxypiperidino) moiety is further substituted. However, Patent No. EP 0241206 A2 generically lists quinolone 3-carboxylic acid derivatives in which the fluoroquinolone core (R=cyclopropyl, X=fluoro, $R_1$=methoxy) has Y as the 7-substituent which is either a 4-hydroxypiperidino moiety or a 3-methyl-4-hydroxypiperidino moiety, of which only the compound bearing the 4-hydroxypiperidino substituent is cited as a preferred compound.

In the compounds of formula I of our invention, when for instance the 8-substituent in the 9-fluoro-8-(substituted piperidine-1-yl)-5-methyl-6,7-dihydro-1-oxo-1H-5H-benzo[i,j]quinolizine-2-carboxylic acid is 4-hydroxy piperidine-1-yl, in which $R_1$, $R_2$ or $R_4$ have the defined meanings as substituents at positions 2-, 3-, 4-, 5- or 6- of the 4-OH-piperidine ring, new asymmetric centres are introduced in the compounds of the invention leading to mixtures of isomeric compounds. One substitution pattern is shown by the following graphic representation.

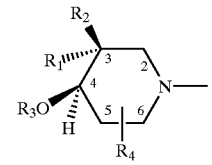

The graphic representations of racemic, ambiscalemic and scalemic or enantiomerically pure compounds used herein are taken from Maehr J.Chem.Ed. 62, 114–120 (1985): solid and broken wedges are used to denote the absolute configuration of a chiral element; wedge outlines and dotted and broken lines denotes enantiomerically pure compounds of indeterminate absolute configuration; wavy lines indicate disavowal of any stereochemical implication which the bond it represents could generate; and solid and broken lines as in the formula above are geometric descriptors indicating the relative configuration shown but specifically denoting racemic character.

The compounds of the invention which are derived from S-(−)-9-fluoro-6,7-dihydro-8-(substituted piperidin-1-yl)-5-methyl-1-oxo-1H,5H-benzo[i,j]quinolizine-2-carboxylic acid have one asymmetric centre which is fixed, viz. the 5(S)-methyl substituent. Additional asymmetric centres arise depending on the positions of the substituents in the 8-substituted piperidin-1-yl moiety of the title compounds of this invention.

For any value of $R_1$ other when $R_1$=H with $R_2$=$R_4$=H and $R_3$ is as defined in this invention, two asymmetric centres arise at C-3 and C-4 in the 8-substituted piperidin-1-yl moiety of the compounds of the invention. For instance, when $R_1$=CH3 and $R_2$=$R_3$=$R_4$=H, there are four possible isomers of a structure having two asymmetric carbons: (RR), (RS), (SR), and (SS). Adopting the convention that the first denoted chiral centre is at C-4 of the 4-hydroxypiperidine moiety and the second is at C-3 of the 4-hydroxypiperidine moiety, compounds of the invention with two asymmetric centres at C-4 and C-3 of the 4-hydroxypiperidine moiety will henceforth be referred to as (4R, 3R), (4R, 3S), (4S, 3R), (4S, 3S) isomers. As the chirality of S-(−)-9-fluoro-6,7-dihydro-8-(4-hydroxypiperidin-1-yl)-5-methyl-1-oxo-1H,5H-benzo[i,j]quinolizine-2-carboxylic acid is fixed, the compounds may comprise a mixture of four diastereomers of S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid, in proportions that can range from a 100% mixture of 5S-trans isomers (4R,3R) and (4S,3S) to a 100% mixture of the 5S-cis isomers (4R,3S) and (4S,3R). Furthermore, because the two sets of cis and trans isomers are diastereomers, they can be separated on the basis of chemical properties such as solubility and crystallisation in achiral media, or by chromatography if need be, but there is no need to do so. Furthermore, the mixture of cis isomers or the mixture of trans isomers can be separated into pure optically active isomers by any one of the chiral techniques known to those skilled in the art.

Another case arises when $R_1$ has a value other than $R_1$=H, $R_4$ is a substituent at the 2- or 5- or 6-positions of the 8-substituted piperidine moiety and has a value other than H but the same value as $R_1$ and $R_2=R_3$=H. For instance, when $R_1$=CH$_3$, $R_2=R_3$=H, $R_4$=5-CH3, there arise two asymmetric centres at C-3 and C-5, with C-4 being achiral in the 4-hydroxypiperidine moiety of the compounds of the invention, resulting in four possible isomers of a structure having two asymmetric carbons, viz. trans-(SR), trans-(RS), cis-(SR) and cis-(RS). Adopting the convention that the first denoted chiral centre is at C-3 of the 4-hydroxypiperidine moiety and the second is at C-5 of the 4-hydroxypiperidine moiety, compounds of invention with two asymmetric centres at C-3 and C-5 of the 4-hydroxypiperidine moiety will henceforth be referred to as trans-(3R,5S), trans-(3S,5R), cis-(3R,5S) and cis-(3S,5R). As the chirality of S-(−)-9-fluoro-6,7-dihydro-8-(4-hydroxypiperidin-1-yl)-5-methyl-1-oxo-1H,5H-benzo[i,j]quinolizine-2-carboxylic acid is fixed, the compounds may comprise a mixture of four diastereomers of S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid, in proportions that can range from a 100% mixture of 5S-trans isomers (3R,5S) and (3S,5R) to a 100% mixture of the 5S-cis isomers (3R,5S) and (3S,5R). Furthermore, because the two sets of cis and trans isomers are diastereomers, they can be separated on the basis of chemical properties such as solubility and crystallisation in achiral media, or by chromatography if need be, but there is no need to do so. Furthermore, the mixture of cis isomers or the mixture of trans isomers can be separated into pure optically active isomers by any one of the chiral techniques known to those skilled in the art.

Our U.S. patent application Ser. No. 09/566,875 filed on May 8, 2000 describes antibacterial optically pure benzoquinolizine carboxylic acids, their derivatives, salts and hydrates thereof, processes for their preparation, and their pharmaceutical compositions for treatment of bacterial Gram-positive, Gram-negative and anaerobic infections and for treatment of diseases caused by resistant Gram-positive organisms, Gram-negative organisms, mycobacteria and nosocomial pathogens. The subject matter of this patent application is incorporated herein by reference.

Streptococci of various groups such as Group A, Group B and Viridans groups are frequent causes of respiratory and other infections in human as well as animals. For example, Streptococcus pyogenes (group A streptococcus) is one of the most common and ubiquitous human pathogens. It is responsible for the majority of cases of sore throat in pediatric patients, and it is also a causative agent of severe life-threatening infections (sepsis, necrotising faciitis, toxic shock syndrome and non-suppurative sequelae such as rheumatic fever and acute glomerulonephritis). Disturbingly, in the recent past there is a wide spread emergence of macrolide antibiotic resistance in-group A streptococci and currently such macrolide resistant strains are routinely reported from Europe, US, Canada and Japan. More recently, macrolide resistance is also reported in Viridans group and group B streptococci.

Additionally, older fluoroquinolone antibiotics such as ciprofloxacin, ofloxacin, pefloxacin and lomefloxacin are only marginally active against streptococci and pneumococci. Several of the newer fluoroquinolones such as Levofloxacin, Gatifloxacin and Moxifloxacin although having improved potency against streptococci and pneumococci, suffer from the deficiencies that their potency against QRSA and MRSA is therapeutically inadequate.

The superior antimicrobial profile of optically pure S-(−)-9-fluoro-8-(4-hydroxypiperidin-1-yl)-5-methyl-6,7-dihydro-1-oxo-1H-5H-benzo[i,j]quinolizine-2-carboxylic acid, its derivatives, salts and hydrates thereof in comparison with RS-(±)-9-fluoro-8-(4-hydroxypiperidin-1-yl)-5-methyl-6,7-dihydro-1-oxo-1H-5H-benzo[i,j]quinolizine-2-carboxylic acid is disclosed in our PCT application WO 00/68229 published on Nov. 16, 2000 and our U.S. patent application Ser. No. 09/566,875. The subject matter of which is incorporated by reference. The novel S-(−)-9-fluoro-6,7-dihydro-8-(4-hydroxypiperidin-1-yl)-5-methyl-1-oxo-1H,5H-benzo[i,j]quinolizine-2-carboxylic acid derivatives, salts and hydrates thereof described therein have excellent potency and potent rapid bactericidal action against staphylococci including MRSA and QRSA strains, Gram-negative pathogens *E. coli*, Klebsiella, Proteus, Serratia, Citrobacter and Pseudomonas, mycobacteria and nosocomial pathogens.

SUMMARY OF THE INVENTION

It has now been discovered that 2-substituted, 3-substituted, 4-substituted, 5-substituted and 6-substituted analogs of the 8-(4-hydroxypiperidinyl) moiety of S-(−)-9fluoro-6,7-dihydro-8-(4-hydroxypiperidin-1-yl)-5-methyl-1-oxo-1H,5H-benzo[i,j]quinolizine-2-carboxylic acid in particular the compounds described below retain the antibacterial properties and profiles as described in our PCT application WO 00/68229 and U.S. patent application Ser. No. 09/566,875 and are effective agents for treating a variety of infections caused by different pathogens belonging to the streptococcus and enterococcus groups. Specially, enterococcal bacteremia, usually encountered with high incidence in large medical centres, is associated with high mortality. Enterococci can also cause serious urinary tract infections. The attributes found for the compounds of the invention are not encompassed with the same potency and cidal action quality by S-(−)-9-fluoro-6,7-dihydro-8-(4-hydroxypiperidin-1-yl)-5-methyl-1-oxo-1H,5H-benzo[i,j] quinolizine-2-carboxylic acid itself and its salts, pseudopolymorphs, polymorphs and hydrates thereof. Acquisition of these streptococcal and enterococcal cidal properties is of potential significant clinical benefit as it results into more effective eradication of pathogens from patients, leading to improved resolution of symptoms related to the respective infections. Additionally, it may also benefit patients in terms of quicker recovery, reduced period of hospitalisation, and shorter duration of antimicrobial treatment. Most significantly, it may also minimize the chances of relapse of infection due to in-vivo selection of resistant subclones of streptococci and enterococci, which might arise in case of antibiotics which have a poorer and incomplete bactericidal action.

Among the 3-substituted, 4-substituted and 5-substituted analogs of the 8-(substituted piperidinyl) moiety of S-(−)-9-fluoro-6,7-dihydro-8-(substituted piperidin-1-yl)-5-methyl-1-oxo-1H,5H-benzo[i,j]quinolizine-2-carboxylic acid, those analogs bearing the optically pure 5S-methyl isomer of the fluoroquinolone core are preferred for treating local and systemic infections, particularly infections caused by a variety of pathogens belonging to the staphylococcus, streptococcus and enterococcus groups, that avoid adverse effects associated with the administration of those analogs bearing the 5R-methyl isomer of the fluoroquinolone core. The present invention also includes processes for the preparation of compounds of this invention and pharmaceutical compositions of the compounds of the invention. The present invention furthermore includes methods for treating local and systemic infections caused by different pathogens belonging to the staphylococcus, streptococcus and enterococcus groups by administering a compound of the invention and more particularly the compounds of the invention bearing the 5S-methyl isomer of the fluoroquinolone core to said human or animal.

DETAILED DESCRIPTION OF THE INVENTION

This invention relates to optically active 8-(substituted piperidino)-benzo [i,j]quinolizines of the formula 1.

Formula I

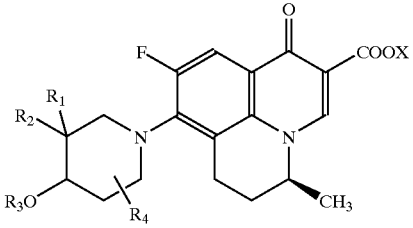

Wherein
X=hydrogen,
or X is $C_1$–$C_{20}$ alkyl, such as straight chain or branched chain aliphatic residues such as methyl, ethyl, propyl, isopropyl, butyl, isobutyl, tertiary butyl, pentyl, hexyl or their branched chain isomers;
or X is aralkyl such as benzyl;
or X is —$(CH_2)_n$—$CHR_{10}$—$OCOR_{11}$, or X is $(CH_2)_n$—$CHR_{10}$—$OCO_2R_{11}$ wherein $R_{10}$ is H, or $CH_3$; n is 0–3 and $R_{11}$ is $C_1$–$C_{20}$ alkyl as hereinbefore defined or substituted $C_1$–$C_6$ alkyl such as hydroxybutyl or aralkyl such as benzyl;
or $R_{11}$ is

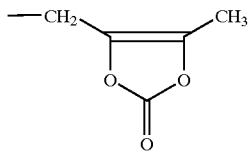

or X is a group such as acetoxymethyl, acetoxyethyl, carbethoxymethyl, pivaloyloxymethyl or pivaloyloxyethyl group;
or X is

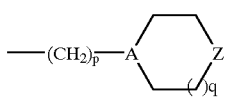

wherein A is CH or N, and when A is CH, Z is NH or $NCH_3$, and when A is N, Z is CH2, O, NH, S, or $NCH_3$; p is 0–2;

q is 0–2, wherein X is a group such as N-methylpiperidin-4-yl, pyrrolidin-2-yl-ethyl, piperidin-2-yl-ethyl, or morpholin-2-yl-ethyl.

$R_1$=$R_2$=H, $C_{1-4}$ alkyl, aralkyl, aminoalkyl, trifluoroalkyl, halogen, except that when $R_1$=H, $R_2$ is not equal to H $R_3$ is hydrogen, or $C_1$–$C_{20}$ alkyl as hereinbefore defined, or glycosyl, or aralkyl such as benzyl, or $C_1$–$C_6$ alkanoyl such as acetyl, propionyl, pivaloyl, stearoyl, or nonadecanoyl or aminoalkanoyl such as amino acid residues derived from one of the 20 naturally occurring amino acids viz. alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine, or the optically active isomers thereof, or the racemic mixtures thereof, or $R_3$ is 1-aminocyclohexylcarbonyl or $R_3$ is $COOR_{11}$ wherein $R_{11}$ is as hereinbefore defined or$(CH_2)_n$—$CHR_{10}$—$OCOR_{11}$ or —$(CH_2)_n$—$CHR_{10}$—$OCOOR_{11}$, where n, $R_{10}$ and $R_{11}$ are as hereinbefore defined, or $C_6H_{11}O_6$, $PO_2(CH_3)$H, $PO_3H_2$, $PO_2(OCH_3)$H or $SO_3H$ thus giving respectively the gluconic acid, phosphonic acid, phosphoric acid and sulfonic acid ester derivatives of the compounds, provided all three of $R_1$, $R_2$ and $R_3$ are not equal to H at the same time;

$R_4$ is H, $C_{1-4}$ alkyl, $CF_3$, phenyl, or F, $R_4$ is present at one or more of the positions of 2-, 4-, 5-, or 6- of the piperidine ring;

or an optical isomer, diastereomer or enantiomer thereof, or polymorphs and pseudopolymorphs or prodrugs thereof or pharmaceutically acceptable salts and hydrates thereof.

"Optical isomer", "stereoisomer", and "diastereomer" as referred to herein have the standard art recognized meanings.

The compounds of the invention may have one or more chiral centers. As a result, one may selectively prepare one optical isomer, including diastereomer and enantiomer, over another, for example by use of chiral starting materials, catalysts or solvents, one may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers, they may be separated using known methods, such as chiral resolution, chiral chromatography and the like.

In addition, it is recognised that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Preferred salts include cationic salts include the alkali metal salts (such as sodium and potassium), alkaline earth metal salts (such as magnesium and calcium), inorganic salts, such as ammonium, substituted ammonium, choline and organic base salts from basic amines such as diethanolamine, n-methylglucamine, ethylenediamine, guanidine or heterocyclic amines such as piperidine, hydroxyethylpyrrolidine, hydroxyethylpiperidine, morpholine, piperazine, N-methyl piperazine and the like or basic amino acids such as optically pure and racemic isomers of arginine, lysine, histidine, tryptophan and the like.

Examples of appropriate acid addition salts include, but are not limited to acetate, adipate, ascorbate, aspartate, benzenesulfonate, benzoate, bicarbonate, bitartrate, butyrate, calcium edetate, camsylate, carbonate, citrate, cyclohexanesulfamate, dodecyl sulfate, edetate, edisylate, estolate, esylate, fumarate, formate, gluceptate, gluconate, glutamate, glycollylarsanilate, glutarate, hexylresorcinate, hydrabamine, hydroxynaphthoate, hydrochloride, hydrobromide, hydroiodide, hydrogensulfate, isethionate, lactate, malate, maleate, mandelate, malonate, methanesulfonate, methylbromide, methylnitrate, methylsulphate, mucate, napsylate, nitrate, oxalate, pamoate (embonate), pantothenate, phosphate/diphosphate, polygalacturonate, propionate, salicylate, stearate, subacetate, succinate, sulfate, tannate, tartrate, teoclate, triethiodide, trifluoroacetate, trifluoromethanesulfonate, p-toluenesulfonate, and the like. However, other appropriate medicinally acceptable salts within the scope of the invention are those derived from other mineral acids, organic acids and amino acids. The amino acid may be selected from one of the 20 naturally occurring amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof or dipeptides, tripeptides and polypeptides derived from the monoaminoacid units thereof.

Preferred compounds of the invention are those wherein:

X = Acetoxymethyl, carbethoxymethyl, pivaloyloxymethyl, 2-piperazinoethyl, 2-morpholinoethyl, 2-pyrrolidinoethyl, or 4-N-methyl piperidinyl;

$R_1$=$CH_3$, $C_2H_5$, n-$C_3H_7$, i-$C_3H_7$, n-$C4H_9$, i-$C_4H_9$, $CF_3$, $CH_2C_6H_5$, $CH_2NH_2$, or F;

$R_2$=H, $CH_3$, $C_2H_5$, n-$C_3H_7$, or n-$C_4H_9$;

$R_3$=H, $CH_3$, $C_2H_5$, $COCH_3$, or $COC(CH_3)_3$; and $R_4$=H, 5-$CH_3$, 5-$C_2H_5$, 4-$CH_3$, 4-$CF_3$, or 4-$C_6H_5$;

or an optical isomer, diastereomer or enantiomer thereof, or polymorphs and pseudopolymorphs or prodrugs thereof or pharmaceutically acceptable salts and hydrates thereof.

Specific compounds of the invention are:

S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid sodium salt. (mixture of cis racemate and trans racemate);

S-(−)-9-fluoro-6,7-dihydro-8-(4-methoxy-3-methylpiperidin-1-yl)-5-methyl-1-oxo-1H,5H-benzo[i,j]quinolizine-2-carboxylic acid. (mixture of cis racemate and trans racemate);

S-(−)-9-fluoro-6,7-dihydro-8-(4-ethoxy-3-methylpiperidin-1-yl)-5-methyl-1-oxo-1H,5H-benzo[i,j]quinolizine-2-carboxylic acid. (mixture of cis racemate and trans racemate);

S-(−)-9-fluoro-6,7-dihydro-8-(4-acetoxy-3-methylpiperidin-1-yl)-5-methyl-1-oxo-1H,5H-benzo[i,j]quinolizine-2-carboxylic acid. (mixture of cis racemate and trans racemate);

S-(−)-9-fluoro-6,7-dihydro-8-(3-methyl-4-pivaloyloxypiperidin-1-yl)-5-methyl-1-oxo-1H,5H-benzo[i,j]quinolizine-2-carboxylic acid. (mixture of cis racemate and trans racemate);

S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylic acid, its isomers, prodrugs and salts;

S-(−)-9-fluoro-6,7-dihydro-8-{trans-(−)-4-R-hydroxy-3-R-methylpiperidin-1-yl}-5-methyl-1-oxo-1H,5H-benzo[i,j]quinolizine-2-carboxylic acid;

S-(−)-9-fluoro-6,7-dihydro-8-{trans-(−)-4-R-hydroxy-3-R-methylpiperidin-1-yl}-5-methyl-1-oxo-1H,5H-benzo[i,j]quinolizine-2-carboxylic acid arginine salt S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid arginine salt;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid histidine salt;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid lysine salt;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid arginine methyl ester salt;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid histidine methyl ester salt;

S-(−)-9-fluoro-6,7-dihydro-8-{cis-4-(RS)-hydroxy-3-(RS)-methylpiperidin-1-yl}-5-methyl-1-oxo-1H,5H-benzo[i,j]quinolizine-2-carboxylic acid, its isomers, prodrugs and salts;

S-(−)-9-fluoro-6,7-dihydro-8-{cis-(−)-4-R-hydroxy-3-S-methylpiperidin-1-yl}-5-methyl-1-oxo-1H,5H-benzo[i,j]quinolizine-2-carboxylic acid, its prodrugs and salts;

S-(−)-9-fluoro-6,7-dihydro-8-{cis-(+)-4-S-hydroxy-3-R-methylpiperidin-1-yl}-5-methyl-1-oxo-1H,5H-benzo[i,j]quinolizine-2-carboxylic acid, its prodrugs and salts;

S-(−)-9-fluoro-6,7-dihydro-8-(4-hydroxy-3-trifluoromethylpiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-(3,3-dimethyl-4-hydroxypiperidin-1-yl)-5-methyl-1-oxo-1H,5H-benzo[i,j]quinolizine-2-carboxylic acid and its isomers;

S-(−)-9-fluoro-6,7-dihydro-8-(4-acetoxy-3,3-dimethylpiperidin-1-yl)-5-methyl-1-oxo-1H,5H-benzo[i,j]quinolizine-2-carboxylic acid and its isomers;

S-(−)-9-fluoro-6,7-dihydro-8-(3,3-dimethyl-4-pivaloyloxypiperidin-1-yl)-5-methyl-1-oxo-1H,5H-benzo[i,j]quinolizine-2-carboxylic acid and its isomers;

S-(−)-9-fluoro-6,7-dihydro-8-(3-ethyl-4-hydroxypiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-(4-acetoxy-3-ethylpiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-(3-ethyl-4-pivaloyloxypiperidin-1-yl)-5-methyl-1-oxo-1H,5H-benzo[i,j]quinolizine-2-carboxylic acid and its isomers;

S-(−)-9-fluoro-6,7-dihydro-8-(3,3-diethyl-4-hydroxypiperidin-1-yl)-5-methyl-1-oxo-1H,5H-benzo[i,j]quinolizine-2-carboxylic acid and its isomers;

S-(−)-9-fluoro-6,7-dihydro-8-(3-ethyl-4-hydroxy-3-methylpiperidin-1-yl)-5-methyl-1-oxo-1H,5H-benzo[i,j]quinolizine-2-carboxylic acid and its isomers;

S-(−)-9-fluoro-6,7-dihydro-8-(4-acetoxy-3-ethyl-3-methylpiperidin-1-yl)-5-methyl-1-oxo-1H,5H-benzo[i,j]quinolizine-2-carboxylic acid and its isomers;

S-(−)-9-fluoro-6,7-dihydro-8-(3-ethyl-4-pivaloyloxy-3-methylpiperidin-1-yl)-5-methyl-1-oxo-1H,5H-benzo[i,j]quinolizine-2-carboxylic acid and its isomers;

S-(−)-9-fluoro-6,7-dihydro-8-(3,5-dimethyl-4-hydroxypiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-(trans-3,5-dimethyl-4-hydroxypiperidin-1-yl)-5-methyl-1-oxo-1H,5H-benzo[i,j]quinolizine-2-carboxylic acid, its isomers, prodrugs and salts;

S-(−)-9-fluoro-6,7-dihydro-8-(cis-3,5-dimethyl-4-hydroxypiperidin-1-yl)-5-methyl-1-oxo-1H,5H-benzo[i,j]quinolizine-2-carboxylic acid, its isomers, its prodrugs and salts;

S-(−)-9-fluoro-6,7-dihydro-8-(4-hydroxy-3-n-propylpiperidin-1-yl)-5-methyl-1-oxo-1H,5H-benzo[i,j]quinolizine-2-carboxylic acid and its isomers;

S-(−)-9-fluoro-6,7-dihydro-8-(3,3-di-n-propyl-4-hydroxypiperidin-1-yl)-5-methyl-1-oxo-1H,5H-benzo[i,j]quinolizine-2-carboxylic acid and its isomers;

S-(−)-9-fluoro-6,7-dihydro-8-(4-hydroxy-3-isopropylpiperidin-1-yl)-5-methyl-1-oxo-1H,5H-benzo[i,j]quinolizine-2-carboxylic acid and its isomers;

S-(−)-9-fluoro-6,7-dihydro-8-(3-n-butyl-4-hydroxypiperidin-1-yl)-5-methyl-1-oxo-1H,5H-benzo[i,j]quinolizine-2-carboxylic acid and its isomers;

S-(−)-9-fluoro-6,7-dihydro-8-(3,3-di-n-butyl-4-hydroxypiperidin-1-yl)-5-methyl-1-oxo-1H,5H-benzo[i,j]quinolizine-2-carboxylic acid and its isomers;

S-(−)-9-fluoro-6,7-dihydro-8-(4-hydroxy-3-iso-butylpiperidin-1-yl)-5-methyl-1-oxo-1H,5H-benzo[i,j]quinolizine-2-carboxylic acid and its isomers;

S-(−)-9-fluoro-6,7-dihydro-8-(3-benzyl-4-hydroxypiperidin-1-yl)-5-methyl-1-oxo-1H,5H-benzo[i,j]quinolizine-2-carboxylic acid and its isomers;

S-(−)-9-fluoro-6,7-dihydro-8-(4-hydroxy-4-methylpiperidin-1-yl)-5-methyl-1-oxo-1H, 5H-benzo[i,j]quinolizine-2-carboxylic acid;

S-(−)-9-fluoro-6,7-dihydro-8-(4-hydroxy-4-trifluoromethylpiperidin-1-yl)-5-methyl-1-oxo-1H,5H-benzo[i,j]quinolizine-2-carboxylic acid;

S-(−)-9-fluoro-6,7-dihydro-8-(4-hydroxy-4-phenylpiperidin-1-yl)-5-methyl-1-oxo-1H,5H-benzo[i,j]quinolizine-2-carboxylic acid;

S-(−)-9-fluoro-6,7-dihydro-8-(4-hydroxy-3-methyl-4-trifluoromethylpiperidin-1-yl)-5-methyl-1-oxo-1H,5H-benzo[i,j]quinolizine-2-carboxylic acid and its isomers;

S-(−)-9-fluoro-6,7-dihydro-8-(3-fluoro-4-hydroxypiperidin-1-yl)-5-methyl-1-oxo-1H, 5H-benzo[i,j]quinolizine-2-carboxylic acid and its isomers;

S-(−)-9-fluoro-6,7-dihydro-8-(3-aminomethyl-4-hydroxypiperidin-1-yl)-5-methyl-1-oxo-1H,5H-benzo[i,j]quinolizine-2-carboxylic acid and its isomers;

S-(−)-9-fluoro-6,7-dihydro-8-(4-hydroxy-3,3,5-trimethylpiperidin-1-yl)-5-methyl-1-oxo-1H,5H-benzo[i,j]quinolizine-2-carboxylic acid and its isomers;

S-(−)-9-fluoro-6,7-dihydro-8-(3,5-dimethyl-3-ethyl-4-hydroxypiperidin-1-yl)-5-methyl-1-oxo-1H,5H-benzo[i,j]quinolizine-2-carboxylic acid and its isomers;

S-(−)-9-fluoro-6,7-dihydro-8-(3,5-diethyl-4-hydroxy-3-methylpiperidin-1-yl)-5-methyl-1-oxo-1H,5H-benzo[i,j]quinolizine-2-carboxylic acid and its isomers;

Pivaloyloxymethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

Acetoxymethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

Carbethoxymethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

2-Piperazino-ethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

2-Morpholino-ethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

2-Pyrrolidino-ethyl S-(−)-9-fluoro-6,7-dihydro-8-{trans-4-(RS)-hydroxy-3-(RS)-methyl piperidin-1-yl}-5-methyl-1-oxo-1H,5H-benzo[i,j]quinolizine-2-carboxylate;

4-(N-methyl)-piperidinyl S-(−)-9-fluoro-6,7-dihydro-8-{trans-4-(RS)-hydroxy-3-(RS)-methyl piperidin-1-yl}-5-methyl-1-oxo-1H,5H-benzo[i,j]quinolizine-2-carboxylate;

Another embodiment of the invention encompasses a process to make the compounds of the invention, which comprise the following general methods.

General Methods

Method 1

S-(−)-9-fluoro-6,7-dihydro-8-(3-or 4- or 5-substituted-4-hydroxypiperidin-1-yl)-5-methyl-1-oxo-1H,5H-benzo[i,j]quinolizine-2-carboxylic acid was prepared by heating a mixture of (O-B)-diacetoxy-{S-(−)-8,9-difluoro-5-methyl-6,7-dihydro-5-methyl-1-oxo-1H,5H-benzo[i,j]quinolizine-2-carboxy}borane with appropriate 3-or 4- or 5-substituted-4-hydroxypiperidine in an organic solvent preferably acetonitrile or dimethyl sulphoxide, optionally in the presence of a base such as triethylamine, at 50°–120° C. preferably 90° C. for 4–24 hr.

Method 2

This invention also includes a method for preparing S-(−)-9-fluoro-6,7-dihydro-8-(3-or 4- or 5-substituted-4-alkanoyloxypiperidin-1-yl)-5-methyl-1-oxo-1H,5H-benzo[i,j]quinolizine-2-carboxylic acid comprising the steps of stirring a mixture of S-(−)-9-fluoro-6,7-dihydro-8-(3- or 4- or 5-substituted-4-hydroxypiperidin-1-yl)-5-methyl-1-oxo-1H,5H-benzo[i,j]quinolizine-2-carboxylic acid with an appropriate alkanoylating agent in presence of a base in the presence or absence of an organic solvent at 0°–100° C. for 0.5–8 hr.

S-(−)-9-fluoro-6,7-dihydro-8-(3-or 4- or 5-substituted-4-acetoxypiperidin-1-yl)-5-methyl-1-oxo-1H,5H-benzo[i,j]quinolizine-2-carboxylic acid was prepared by stirring a mixture of S-(−)-9-fluoro-6,7-dihydro-8-(3-, or 4- or 5-substituted-4-hydroxypiperidin-1-yl)-5-methyl-1-oxo-1H,5H-benzo[i,j]quinolizine-2-carboxylic acid with acetic anhydride in presence of a base preferably pyridine or triethylamine in the presence or absence of an organic solvent at 0°–100° C. for 0.5–8 hr preferably 2 hr.

Similarly prepared was S-(−)-9-fluoro-6,7-dihydro-8-(3- or 4- or 5-substituted-4-pivaloyloxypiperidin-1-yl)-5-methyl-1-oxo-1H,5H-benzo[i,j]quinolizine-2-carboxylic acid using pivaloyl chloride in place of acetic anhydride.

Method 3

This invention also includes a method for preparing alkanoyloxymethyl S-(−)-9-fluoro-6,7-dihydro-8-(trans 4-hydroxy-3-methylpiperidin-1-yl)-5-methyl-1-oxo-1H,5H-benzo[i,j]quinolizine-2-carboxylic acid comprising the steps of treating S-(−)-9-fluoro-6,7-dihydro-8-(4-hydroxy-3-methylpiperidin-1-yl)-5-methyl-1-oxo-1H,5H-benzo[i,j]

quinolizine-2-carboxylic acid with halomethyl alkanoate in presence of a base in the presence or absence of an organic solvent at 0°–100° C. for 2–24 hr.

Pivaloyloxymethyl S-(−)-9-fluoro-6,7-dihydro-8-{trans-4-hydroxy-3-methylpiperidin-1-yl)-5-methyl-1-oxo-1H,5H-benzo[i,j]quinolizine-2-carboxylate was prepared by treating S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid with chloromethyl pivalate in the presence of a base preferably potassium carbonate in the presence or absence of an organic solvent at 0°–100° C. preferably 50° C. for 2–24 hr preferably 18 hr.

Similarly prepared were acetoxymethyl S-(−)-9-fluoro-6,7-dihydro-8-{trans-4-hydroxy-3-methylpiperidin-1-yl)-5-methyl-1-oxo-1H,5H-benzo[i,j]quinolizine-2-carboxylate and propionyloxymethyl S-(−)-9-fluoro-6,7-dihydro-8-{trans-4-hydroxy-3-methylpiperidin-1-yl)-5-methyl-1-oxo-1H,5H-benzo[i,j]quinolizine-2-carboxylate by using chloromethyl acetate or ethyl bromo acetate respectively in place of chloromethyl pivalate.

Method 4

This invention also includes a method for preparing heterocyclic amino/heterocyclic aminoalkyl S-(−)-9-fluoro-6,7-dihydro-8-{trans-4-hydroxy-3-methylpiperidin-1-yl)-5-methyl-1-oxo-1H,5H-benzo[i,j]quinolizine-2-carboxylate comprising the steps of treating S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid with hydroxy heteroycyclic amine/hydroxyalkyl heterocyclic amine in presence of a base in the presence or absence of an organic solvent at 50°–100° C. for 2–48 hr.

2-Piperazinoethyl S-(−)-9-fluoro-6,7-dihydro-8-{trans-4-hydroxy-3-methylpiperidin-1-yl)-5-methyl-1-oxo-1H,5H-benzo[i,j]quinolizine-2-carboxylate was prepared by treating S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid with N-2-hydroxyethyl piperazine in presence of a base such as 4-N,N-dimethylamino pyridine and triethylamine, in the presence of a condensing agent such as N,N-dicyclohexylcarbodiimide and in the presence or absence of an organic solvent such as N,N-dimethyl acetamide at 50°–100° C. for 2–48 hr.

Similarly prepared were 2-Morpholino ethyl S-(−)-9-fluoro-6,7-dihydro-8-{trans-4-hydroxy-3-methylpiperidin-1-yl)-5-methyl-1-oxo-1H,5H-benzo[i,j]quinolizine-2-carboxylate, 2-pyrrolidino ethyl S-(−)-9-fluoro-6,7-dihydro-8-{trans-4-hydroxy-3-methylpiperidin-1-yl)-5-methyl-1-oxo-1H,5H-benzo[i,j]quinolizine-2-carboxylate and 4-(N-methyl)-piperidinyl S-(−)-9-fluoro-6,7-dihydro-8-{trans-4-hydroxy-3-methylpiperidin-1-yl)-5-methyl-1-oxo-1H,5H-benzo[i,j]quinolizine-2-carboxylate by using N-2-hydroxyethyl morpholine, N-2-hydroxyethyl pyrrolidine or 4-hydroxy-N-methylpiperidine respectively in place of N-2 hydroxyethyl piperazine.

Method 5

The pharmaceutically acceptable cationic salts of compounds I may be prepared by conventional methods from the corresponding acids e.g. by reaction with about one equimolar amount of a base. Examples of suitable cationic salts are those of alkali metals such as sodium or potassium, alkaline earth metals such as magnesium or calcium and ammonium or organic amines such as diethanolamine or N-methylglucamine, ethylenediamine, guanidine or heterocyclic amines such as piperidine, hydroxyethylpyrrolidine, hydroxyethylpiperidine, morpholine, piperazine, N-methyl piperazine and the like or basic amino acids such as optically pure and racemic isomers of arginine, lysine, histidine, tryptophan and the like.

The hydrates, pseudopolymorphs and polymorphs of all the compounds of the invention are also included.

The present invention also encompasses the process of making the intermediate amines, as illustrated in the detailed preparations that are used in the condensation with the fluoroquinolone nucleus. For instance, the 3-substituted-4-hydroxy piperidine intermediates can exist as a mixture of cis and trans isomers. Each cis and trans isomer is a racemic mixture and can be resolved into optically active enantiomeric forms. Each cis or trans isomer, optionally debenzylated and/or deacetylated can be resolved into their optically active enantiomers by conventional methods known to those skilled in the art of resolving racemic mixtures by fractional crystallisation of their salts with appropriate resolving agents or by chromatography or by enzymatic techniques. The methods for preparation of the mixture of cis and trans isomers and their resolution into enantiomeric forms is exemplified for instance by the following example of 3-methyl-4-hydroxy piperidine 1-Benzyl-4-acetoxy-3-methylpiperidine (a mixture of cis and trans isomers) was prepared according to the literature procedure [A. F. Casy and W. K. Jeffery, Can.J.Chem. 50 (1972), 803] and separated by silica gel chromatography into the respective cis and trans isomers. The end result of using such resolution and/or chemical procedures is to obtain the optically active enantiomer of cis-3-methyl-4-hydroxypiperidine and of trans-3-methyl-4-hydroxypiperidine. Using any one of the enantiomeric mixtures of cis-3-methyl-4-hydroxypiperidine or trans-3-methyl-4-hydroxypiperidine or one of their optically pure enantiomers, the compounds of the invention can be prepared by condensing the respective 3-methyl-4-hydroxypiperidine with (O-B)-diacetoxy-[S-(−)-8,9-difluoro-5-methyl-1-oxo-1H,5H-benzo[i,j]quniolizine-2-carboxy]borane, as exemplified in the section on examples described later in this specification.

The present invention also encompasses antiinfective compositions for the treatment of humans and animals in need of therapy for systemic or topical infections especially resistant Gram-positive organism infections, Gram-negative organism infections, mycobacterial infections and nosocomial pathogen infections. A composition according to this invention comprises an amount of optically pure compounds of the invention, or the derivatives, salts, hydrates, pseudopolymorphs and polymorphs thereof, preferably, substantially free of the compounds of the invention bearing the 5R-methyl enantiomer of the fluoroquinolone core, said amount being sufficient to eradicate said infection. The composition should provide a therapeutic dose, which is insufficient to cause the toxic effects associated with the comparable compositions comprised of compounds of the invention bearing the 5RS-isomeric mixture of the fluoroquinolone core.

In addition the compounds of the invention have superior bactericidal activity against pneumococci, streptococci and enterococci of various groups. Cidal features available in such molecules add to their clinical attractiveness as it would offer clinicians a valuable treatment option to treat a broader range of infections caused by staphylococci, MRSA, MRSE, pneumococci, streptococci and enterococci in a situation such as patients allergic to β-lactam or possibility of infections due to macrolide resistant strains of streptococci, pneumococci and enterococci or MRSA/

QRSA/VRE. The compounds of the invention have potential not only to suppress the growth of VRE strains but also a dual advantage of reducing or curtailing vacomycin usage for the treatment of MRSA infections and thereby not creating circumstances favourable for VRE emergence. Moreover, the molecules of the invention also retain the other valuable features of S-(−)-9-fluoro-6,7-dihydro-8-(4-hydroxypiperidin-1-yl)-5-methyl-1-oxo-1H,5H-benzo[i,j]quinolizine-2-carboxylic acid its derivatives, salts, pseudopolymorphs, polymorphs and hydrates thereof, of being bactericidal to fluoroquinolone resistant staphylococci (QRSA with resistant gyrase) and even to staphylococcal isolates possessing Nor A efflux pump. A combination of all these properties coupled with overall good safety and tolerability observed in a new molecule renders it worthy of therapeutic use in humans and animals.

The above list of pathogens is merely by way of example and is in no way to be interpreted as limiting. Streptococci are implicated as one of the most common pathogens, in both the pediatric and adult population in diverse infections/diseases. Examples which may be mentioned of diseases, which can thus be prevented, alleviated and/or cured by the formulations according to the invention are meningitis, otitis externa, otitis media; pharyngitis; pneumonia; life-threatening bacteremia, peritonitis; pyelonephritis; cystitis; endocarditis; systemic infections; bronchitis; arthritis; local infections; septic diseases. Examples of enterococcal diseases are specially enterococcal bacteremia and urinary tract infections.

These findings have an important implication from the point of view of the systemic use of the compounds of the invention in view of their superior potency, superior bactericidal activity, expanded biospectrum, better bioavailability and improved tolerability are now enabled to be administered systemically in therapeutically effective doses.

Utilising the substantially optically pure or optically pure isomer or optically pure compounds of the invention, the derivatives and salts thereof, whether in systemic or topical dosage form, results in clearer dose-related definitions of efficacy, diminished toxic effects and accordingly an improved therapeutic index.

The pharmaceutical compositions are prepared according to conventional procedures used by persons skilled in the art to make stable and effective compositions. In the solid, liquid, parenteral and topical dosage forms, an effective amount of the active compound or the active ingredient is any amount, which produces the desired results.

For the purpose of this invention the pharmaceutical compositions may contain the active compounds of the invention, their derivatives, salts and hydrates thereof, in a form to be administered alone, but generally in a form to be administered in admixture with a pharmaceutical carrier selected with regard to the intended route of administration and standard pharmaceutical practice. Suitable carriers which can be used are, for example, diluents or excipients such as fillers, extenders, binders, emollients, wetting agents, disintegrants, surface active agents and lubricants which are usually employed to prepare such drugs depending on the type of dosage form.

Any suitable route of administration may be employed for providing the patient with an effective dosage of the compound of the invention their derivatives, salts and hydrates thereof. For example, oral, rectal, parenteral (subcutaneous, intramuscular, intravenous), transdermal, topical and like forms of administration may be employed. Dosage forms include (solutions, suspensions, etc) tablets, pills, powders, troches, dispersions, suspensions, emulsions, solutions, capsules, injectable preparations, patches, ointments, creams, lotions, shampoos and the like.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

The compositions of the present invention include compositions such as suspensions, solutions, elixirs, aerosols, and solid dosage forms. Carriers as described in general above are commonly used in the case of oral solid preparations (such as powders, capsules and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. Examples of suitable carriers include excipients such as lactose, white sugar, sodium chloride, glucose solution, urea, starch, calcium carbonate, kaolin, crystalline cellulose and silicic acid, binders such as water, ethanol, prepanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic acid salts, boric acid powder, polyethylene glycol and solid polyethylene glycol.

The tablet, if desired, can be coated, and made into sugar-coated tablets, gelatin-coated tablets, enteric-coated tablets, film-coated tablets, or tablets comprising two or more layers.

If desired, tablets may be coated by standard aqueous or nonaqueous techniques.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, gelatin, and semi-synthetic glycerides.

A second preferred method is parenterally for intramuscular, intravenous or subcutaneous administration.

A third preferred route of administration is topically, for which creams, ointments, shampoos, lotions, dusting powders and the like are well suited. Generally, an effective amount of the compound according to this invention in a topical form 0.1% composition is to about 10% by weight of the total composition. Preferably, the effective amount is 1% of the total composition.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

Desirably, each tablet contains from about 200 mg to about 1500 mg of the active ingredient. Most preferably, the tablet, cachet or capsule contains either one of three dosages, about 200 mg, about 400 mg, or about 600 mg of the active ingredient.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

The antimicrobial pharmaceutical composition may further contain ordinary dissolving aids, buffers, pain-alleviating agents, and preservatives, and optionally coloring agents, perfumes, flavors, sweeteners, and other drugs.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient preferably in combination with a solid or liquid inert carrier material.

A specific embodiment of the invention is the preparation of storage stable compositions of the compounds of the invention of formula I. Such stable compositions can be advantageously made through the use of selective stabilizers. Different stabilizers are known to those skilled in the art of making pharmaceutical compositions. Of special utility for making storage stable compositions of the compound of the invention of formula I, stabilizers such as disodium EDTA, tromethamine, cyclodextrins such as gamma-cyclodextrin, hydroxy-propyl-gamma-cyclodextrin have been found to be useful. A specific embodiment of the invention utilises arginine as an excipient in compositions to facilitate the aqueous solubility of the compounds of the invention which comprises utilising an appropriate molar amount of arginine with a specific compound of the invention.

In a specific embodiment of the invention, the pharmaceutical compositions contain an effective amount of the active compounds of the invention, its derivatives, salts or hydrates thereof described in this specification as hereinbefore described in admixture with a pharmaceutically acceptable carrier, diluent or excipients, and optionally other therapeutic ingredients.

The prophylactic or therapeutic dose of the compounds of the invention, their derivatives, salts or hydrates thereof, in the acute or chronic management of disease will vary with the severity of condition to be treated, and the route of administration. In addition, the dose, and perhaps the dose frequency, will also vary according to the age, body weight and response of the individual patient. In general, the total daily dose range, for the compounds of the invention, the derivatives, salts or hydrates thereof, for the conditions described herein, is from about 200 mg to about 1500 mg, in single or divided doses. Preferably, a daily dose range should be between about 400 mg to 1200 mg, in single or divided dosage, while most preferably a daily dose range should be between about 500 mg to about 1000 mg in divided dosage. While intramuscular administration may be a single dose or up to 3 divided doses, intravenous administration can include a continuous drip. It may be necessary to use dosages outside these ranges in some cases as will be apparent to those skilled in the art. Further, it is noted that the clinician or treating physician will know how and when to interrupt, adjust, or terminate therapy in conjunction with individual patient's response. The term "an amount sufficient to eradicate such infections but insufficient to cause said toxic effect" is encompassed by the above-described dosage amount and dose frequency schedule.

The invention is further defined by reference to the following examples describing in detail the preparation of the composition of the present invention as well as their utility. It will be apparent to those skilled in the art that many modifications, both to materials and methods may be practiced without departing from the purpose and scope of this invention.

The following preparations and examples illustrate the methods of preparation of the compounds of the invention and are provided only as examples, but not to limit the scope of the compounds of the invention.

Preparation 1

4-Hydroxy-4-trifluoromethylpiperidine

A mixture of 1-benzyl-4-piperidone (2.2 g, 11.67 mmole) and (trifluoromethyl)-trimethyl silane (2.37 g, 16.7 mmole) in dry THF (10 ml) at 0° C. was treated with tetrabutylammonium fluoride (0.02 g) in THF. The mixture was stirred at 0° C. for 15 min and allowed to stir at 25–30° C. for 2 hr. THF (10 ml) and 3N HCl were added and stirred for 2 hr. The reaction mixture was extracted with ethyl acetate (3×25 ml), washed with water (2×10 ml) and brine (20 ml), dried ($Na_2SO_4$). Residue obtained after evaporation of solvent was purified by column chromatography over silica gel. Elute from a mixture of 5% methanol in chloroform gave 1-benzyl-4-hydroxy-4-trifluoromethylpiperidine as an oil. Yield 2.2 g, (73%), $C_{13}H_{24}NOF_3$, m/z 260 (M+1), PMR ($CDCl_3$): 1.7 (2H, d, $CH_2$, j=10 Hz), 1.85 (1H, bs, OH, $D_2O$ exchangeable), 1.9 (2H, t, $CH_2$, j=10 Hz), 2.3 (2H, t, $CH_2$, j=10 Hz), 2.8 (2H, d, $CH_2$, j=10 Hz), 3.55 (2H, s, $CH_2Ar$), 7.2–7.4 (5H, m, ArH).

1-Benzyl-4-hydroxy-4-trifluoromethylpiperidine (2.0 g, 7.72 mmole) was stirred with 20% palladium hydroxide (0.15 g) in methanol under hydrogen for 40 hr at 30° C. The reaction mixture was filtered and concentrated at reduced pressure to furnish 4-hydroxy-4-trifluoro-methylpiperidine. Yield 1.28 g (98%) $C_6H_{10}NOF_3$, m/z 170 (M+1), PMR ($CDCl_3$): 1.8–2.1 (4H, m, 2×$CH_2$), 3.1–3.5 (4H, m, 2×$CH_2$).

Preparation 2 trans-4-(RS)-Hydroxy-3-(RS)-methylpiperidine

A mixture of trans-1-benzyl-4-(RS)-acetoxy-3-(RS)-methylpiperidine [7 g, 28.5 mmole {prepared according to literature procedure described in A. F. Casy and W. K. Jeffery, Can.J.Chem., 50 (1972), 803}] and 20% palladium hydroxide (1.8 g) in methanol (25 ml) was stirred at 50–55° C. under hydrogen (1 atmosphere) for 20 hr. The catalyst was filtered off and washed with methanol. Filtrate was concentrated to give trans-4-(RS)-acetoxy-3-(RS)-methyl piperidine as oil. Yield 4.41 g (100%), $C_8H_{15}NO_2$, m/z 158 (M+1), PMR (CDCl$_3$): 0.94 (3H, d, CH$_3$, j=8 Hz), 1.42 (1H, m, H$_3$), 1.67 (1H, m, H$_5$), 1.98 (1H, m, H$_5$), 2.08 (3H, s, COCH$_3$), 2.3 (1H, t, H$_2$, j=12 Hz), 2.68 (1H, dt, H$_2$, j=3 Hz, 12 Hz), 3.04 (2H, in, H$_6$), 4.5 (1H, dt, H$_4$, j=3 Hz, 12 Hz).

The obtained trans-4-(RS)-acetoxy-3-(RS)-methylpiperidine (4.41 g) was refluxed with aqueous NaOH (25 ml, 10%) for 5 hr, cooled and extracted with ethyl acetate (2×50 ml). The extract was washed with water, dried (sodium sulphate), concentrated to furnish trans-4-(RS)-hydroxy-3-(RS)-methylpiperidine as colourless oil. Yield 3.26 g (90%), $C_6H_{13}NO$, m/z 116 (M+1), PMR (CD$_3$OD): 0.98 (3H, d, CH$_3$, j=8 Hz), 1.6 (2H, m, H$_3$ & H$_5$), 2.04 (1H, m, H$_5$), 2.64 (1H, t, H$_2$, j=12 Hz), 2.92 (1H, dt, H$_2$, j=3 Hz, 12 Hz), 3.28 (3H, m, H$_4$ & H$_6$).

Preparation 3

Trans-(+)-4S-acetoxy-3 S-methylpiperidine

Method 1

A solution of 1-benzyl-3-methylpiperidin-4-one (25.3 g, 125.0 mmole) in dry tetrahydrofuran (100 ml) was added to the stirred solution of (−)-diisopinocampheyl borane (35.9 g, 126.0 mmole {prepared according to the procedure described in H. C. Brown, J.Org.Chem., 49 (1984), 945}) in dry tetrahydrofuran (200 ml) at −78° C. over a period of 1 hr under nitrogen atmosphere. The stirring was continued for 2 hr at −78° C. and stirring continued for 12 at ambient temperature. The resulting stirred borane complex was decomposed with aqueous NaOH solution (10%) and hydrogen peroxide (7 ml, 30%) respectively at 0° C. over a period of 1 hr. The reaction mixture was extracted with ethyl acetate (2×250 ml), ethyl acetate extract was washed with brine solution, dried (Na$_2$SO$_4$) and concentrated to give a crude mixture of cis- and trans-1-benzyl-4-hydroxy-3-methylpiperidine as oil. Yield 21 g (82%), $C_{13}H_{19}NO$, m/z 206 (M+1).

Acetic anhydride (12.54 ml, 122.0 mmole) was added dropwise to the stirred solution of the above obtained crude mixture of cis-/trans-1-benzyl-4-hydroxy-3-methylpiperidine (21 g, 102.0 mmole) and 4-N,N-dimethylpyridine (0.25 g) in pyridine (50 ml) at 0–5° C. The reaction mixture was stirred for 2 hr at ambient temperature and concentrated to dryness. The residue thus obtained was dissolved in ethyl acetate, washed with water, dried (Na$_2$SO$_4$) and concentrated to dryness to furnish crude mixture of cis- and trans-4-acetoxy-1-benzyl-3-methylpiperidine as oil. The obtained mixture of cis and trans 4-acetoxy-1-benzyl-3-methylpiperidine was separated on silica column. Elution from 7% ethyl acetate in hexane gave trans-(+)-4-S-acetoxy-1-benzyl-3-S-methylpiperidine. Yield 6.0 g (35%), $[\alpha]_D$+16.8°, $C_{15}H_{21}NO_2$, m/z 248 (M+1), PMR (CDCl$_3$): 0.94 (3H, d, CH$_3$, j=8 Hz), 1.62 (1H, m, H$_3$), 1.78–2.2 (2H, m, H$_5$), 2.08 (3H, s, COCH$_3$), 2.84 (4H, m, H$_2$ & H$_6$), 3.5 (2H, s, NCH$_2$), 4.42 (1H, dt, H$_4$, j=3 Hz, 12 Hz), 7.31 (5H, s, ArH).

Elution from 7% ethyl acetate in hexane gave mixture of cis- and trans-4-acetoxy-1-benzyl-3-methylpiperidine. Yield 6.3 g (37%). Further elution from 20% ethyl acetate in hexane gave cis-(+)-4-S-acetoxy-1-benzyl-3-R-methylpiperidine. Yield 4.5 g (26%),$[\alpha]_D$+22°, $C_{15}H_{21}NO_2$, m/z 248 (M+1), PMR (CDCl$_3$): 0.92 (3H, d, CH$_3$, j=8 Hz), 1.84 (2H, m, H$_5$), 2.12 (3H, s, COCH$_3$), 2.2–2.76 (5H, m, H$_2$, H$_3$ & H$_6$), 3.62 (2H, s, NCH$_2$), 4.98 (1H, m, H$_4$), 7.36 (5H, s, ArH).

Method 2

A solution of dibenzoyl L-(−)-tartaric acid monohydrate (19.0 g, 50.9 mmole) in ethyl acetate (32 ml) was added to the stirred solution of trans-4-(RS)-acetoxy-3-(RS)-methylpiperidine (16.0 g, 101.9 mmole) in ethyl acetate (32 ml). The solid thus separated was filtered, washed with ethyl acetate (250 ml) and recrystallized from methanol to give dibenzoyl trans-(−)-4S-acetoxy-3S-methylpiperidine-L-tartrate. Yield 10.75 g (39.8%), $[\alpha]_D$−60.2°. $C_{26}H_{29}NO_{10}$, m/z 516 (M+1), PMR (D$_2$O): 0.92 (3H, d, CH$_3$, j=8 Hz), 1.64 (1H, m, H$_3$), 2.05 (3H, s, COCH$_3$), 2.2 (2H, m, H$_5$), 2.82 (1H, t, H$_2$, j=12 Hz), 3.08 (1H, dt, H$_2$, j=3 Hz, 12 Hz), 3.4 (2H, m, H$_6$), 4.66 (1H, m, H$_4$), 5.65 (2H, s, CH), 7.5 (4H, t, ArH, j=8 Hz), 7.65 (2H, t, ArH, j=8 Hz), 8.08 (4H, d, ArH, j=8 Hz).

Dibenzoyl trans-(−)-4S-acetoxy-3S-methylpiperidine-L-tartrate (21.5 g, 41.7 mmole) was suspended in ethyl acetate (250 ml) and basified (pH 8.5) with aqueous sodium carbonate solution (10%). Ethyl acetate layer was separated, washed with water, dried (Na$_2$SO$_4$) and concentrated to dryness to furnish trans-(+)-4S-acetoxy-3S-methylpiperidine as colourless oil. Yield 6.3 g (95.7%), $[\alpha]_D$+24°, $C_8H_{15}NO_2$, m/z 158 (M+1), PMR (CDCl$_3$): 0.94 (3H, d, CH$_3$, j=8 Hz), 1.42 (1H, m, H$_3$), 1.67 (1H, m, H$_5$), 1.98 (1H, m, H$_5$), 2.08 (3H, s, COCH$_3$), 2.3 (1H, t, H$_2$, j=12 Hz), 2.68 (1H, dt, H$_2$, j=3 Hz, 12 Hz), 3.04 (2H, m, H$_6$), 4.5 (1H, dt, H$_4$, j=3 Hz, 12 Hz).

Preparation 4

Trans-(+)-4S-hydroxy-3 S-methylpiperidine

A solution of 1-benzyl-trans-(+)-4S-acetoxy-3S-methylpiperidine (6.0 g, 24.2 mmole) in aqueous NaOH (10 ml, 10%) was refluxed for 15 hr, cooled and extracted with ethyl acetate (2×50 ml). The ethyl acetate extract was washed with water, dried (Na$_2$SO$_4$) and concentrated to furnish (+)-trans-1-benzyl-4S-hydroxy-3S-methylpiperidine as a colourless oil. Yield 4.7 g (95.9%), $[\alpha]_D$+° (c=1%, methanol solution), $C_{13}H_{19}NO$, m/z 206 (M+1) PMR (CDCl$_3$): 0.98 (3H, d, CH$_3$, j=8 Hz), 1.56–1.8 (3H, m, H$_3$ & H$_5$), 1.88–2.14 (2H, m, H$_6$), 2.86 (2H, dt, H$_2$, j=3 Hz, 12 Hz), 3.14 (1H, m, H$_4$), 3.52 (2H, s, N—CH$_2$), 7.3 (5H, m, ArH).

A mixture of trans-(+)-1-benzyl-4S-hydroxy-3S-methylpiperidine (4.7 g, 0.023 mole) and palladium hydroxide (1.5 g) in a methanol (25 ml) was stirred at 50–55° C. under hydrogen (1 atmosphere) for 20 hr. The catalyst was filtered off, washed with methanol, filtrate and washings were concentrated to dryness to give trans-(+)-4S-hydroxy-3S-methylpiperidine as an oil. Yield 2.59 g (98%), $[\alpha]_D$+° (c=1%, methanol solution), $C_6H_{13}NO$, m/z 116 (M+1), PMR (CD$_3$OD): 0.98 (3H, d, CH$_3$, j=8 Hz), 1.6 (2H, m, H$_3$ & H$_5$), 2.04 (1H, m, H$_5$), 2.64 (1H, t, H$_2$, j=12 Hz), 2.92 (1H, dt, H$_2$, j=3 Hz, 12 Hz), 3.28 (3H, m, H$_4$ & H$_6$).

Preparation 5

Trans-(−)-4R-acetoxy-3R-methylpiperidine

Method 1

A solution of 1-benzyl-3-methylpiperidin-4-one (15.0 g, 0.073 mole) in dry tetrahydrofuran (125 ml) was added to the stirred solution of (+)-diisopinocampheyl borane (20.8 g, 0.075 mole {prepared according to the procedure described in H. C. Brown, J.Org.Chem., 49 (1984), 945}) in dry tetrahydrofuran (125 ml) at −78° C. over a period of 1 hr under nitrogen atmosphere. The stirring was continued for 2 hr at −78° C. and stirring continued for 24 at ambient temperature. The resulting stirred borane complex was decomposed with aqueous NaOH solution (10%) and hydrogen peroxide (10 ml, 30%) respectively at 0° C. over a period of 1 hr. The reaction mixture was extracted with ethyl acetate (2×100 ml), ethyl acetate extract was washed with brine solution, dried ($Na_2SO_4$) and concentrated to give a mixture of cis- and trans-1-benzyl-4-hydroxy-3-methylpiperidine as oil. Yield 6.9 g (82%), $C_{13}H_{19}NO$, m/z 206 (M+1).

Acetic anhydride (4.08 ml, 0.04 mole) was added dropwise to the stirred solution of the obtained mixture of cis-/trans-1-benzyl-4-hydroxy-3-methylpiperidine (6.9 g, 0.033 mole) and 4-N,N-dimethylpyridine (0.05 g) in pyridine (20 ml) at 0–5° C. The reaction mixture was stirred for 2 hr at ambient temperature and concentrated to dryness. The residue thus obtained was dissolved in ethyl acetate, washed with water, dried ($Na_2SO_4$) and concentrated to dryness to furnish a mixture of cis- and trans-4-acetoxy-1-benzyl-3-methylpiperidine as oil. The obtained mixture of cis and trans 4-acetoxy-1-benzyl-3-methylpiperidine was separated on silica column. Elution from 5% ethyl acetate in hexane gave trans-(−)-4-R-acetoxy-1-benzyl-3-R-methylpiperidine. Yield 2.12 g (25%), $[\alpha]_D$ −13.2° (c=1%, methanol solution), $C_{15}H_{21}NO_2$, m/z 248 (M+1), PMR ($CDCl_3$): 0.94 (3H, d, $CH_3$, j=8 Hz), 1.62 (1H, m, $H_3$), 1.78–2.2 (2H, m, $H_5$), 2.08 (3H, s, $COCH_3$), 2.84 (4H, m, $H_2$ & $H_6$), 3.5 (2H, s, $NCH_2$), 4.42 (1H, dt, $H_4$, j=3 Hz, 12 Hz), 7.31 (5H, s, ArH).

Further elution from 10% ethyl acetate in hexane gave cis-(−)-4-R-acetoxy-1-benzyl-3-S-methylpiperidine. Yield 3.34 g (40%), $[\alpha]_D$ −6° (c=1%, methanol solution), $C_{15}H_{21}NO_2$, m/z 248 (M+1), PMR ($CDCl_3$): 0.92 (3H, d, $CH_3$, j=8 Hz), 1.84 (2H, m, $H_5$), 2.12 (3H, s, $COCH_3$), 2.2–2.76 (5H, m, $H_2,H_3$ & $H_6$), 3.62 (2H, s, $NCH_2$), 4.98 (1H, m, $H_4$), 7.36 (5H, s, ArH).

Method 2

A solution of dibenzoyl D-(+)-tartaric acid (18.1 g, 50.9 mmole) in ethyl acetate (32 ml) was added to the stirred solution of trans-4-(RS)-acetoxy-3-(RS)-methylpiperidine (16 g, 101.9 mmole) in ethyl acetate (32 ml). The salt thus separated was filtered, washed with ethyl acetate (250 ml) and recrystallized from methanol to give dibenzoyl trans-(+)-4R-acetoxy-3R-methylpiperidine-D-tartrate. Yield 9.4 g (37.6%), $[\alpha]_D$ +59.3° (c=1%, methanol solution), $C_{26}H_{29}NO_{10}$, m/z 516 (M+1), PMR ($D_2O$): 0.92 (3H, d, $CH_3$, j=8 Hz), 1.64 (1H, m, $H_3$), 2.05 (3H, s, $COCH_3$), 2.2 (2H, m, $H_5$), 2.82 (1H, t, $H_2$, j=12 Hz), 3.08 (1H, dt, $H_2$, j=3 Hz, 12 Hz), 3.4 (2H, m, $H_6$), 4.66 (1H, m, $H_4$), 5.65 (2H, s, CH), 7.5 (4H, t, ArH, j=8 Hz), 7.65 (2H, t, ArH, j=8 Hz), 8.08 (4H, d, ArH, j=8 Hz).

Dibenzoyl trans-(+)-4R-acetoxy-3R-methylpiperidine-D-tartrate (18.8 g, 36.5 mole) was suspended in ethyl acetate (250 ml) and basified (pH 8.5) with 10% sodium carbonate solution. Ethyl acetate layer was separated, washed with water, dried ($Na_2SO_4$) and concentrated to afford trans-(−)-4R-acetoxy-3R-methylpiperidine. Yield 5.4 g (95.7%), $[\alpha]_D$ −12° (c=1%, methanol solution), $C_8H_{15}NO_2$, m/z 158 (M+1), PMR ($CDCl_3$): 0.94 (3H, d, $CH_3$, j=8 Hz), 1.42 (1H, m, $H_3$), 1.67 (1H, m, $H_5$), 1.98 (1H, m, $H_5$), 2.08 (3H, s, $COCH_3$), 2.3 (1H, t, $H_2$, j=12 Hz), 2.68 (1H, dt, $H_2$, j=3 Hz, 12 Hz), 3.04 (2H, m, $H_6$), 4.5 (1H, dt, $H_4$, j=3 Hz, 12 Hz).

Preparation 6

Trans-(−)-4R-hydroxy-3R-methylpiperidine

A solution of trans-(−)-1-benzyl-4R-acetoxy-3R-methylpiperidine (5.4 g, 0.0218 mole) in aqueous NaOH (10 ml, 10%) was refluxed for 15 hr, cooled and extracted with ethyl acetate (2×50 ml). The ethyl acetate extract was washed with water, dried over sodium sulphate, concentrated to furnish trans-(−)-1-benzyl-4R-hydroxy-3R-methylpiperidine as colorless oil. Yield 4.1 g (94%), $C_{13}H_{19}NO$, m/z 206 (M+1), PMR ($CDCl_3$): 0.98 (3H, d, $CH_3$, j=8 Hz), 1.56–1.8 (3H, m, $H_3$ & $H_5$), 1.88–2.14 (2H, m, $H_6$), 2.86 (2H, dt, $H_2$, j=3 Hz, 12 Hz), 3.14 (1H, m, $H_4$), 3.52 (2H, s, N—$CH_2$), 7.3 (5H, m, ArH).

A mixture of trans-(−)-benzyl-4R-hydroxy-3R-methylpiperidine (4.1 g, 0.02 mole) and palladium hydroxide (1.4 g) in methanol (25 ml) was stirred at 50–55° C. under hydrogen (1 atmosphere) for 20 hr. The catalyst was filtered off and washed with methanol The filtrate was concentrated to dryness to give trans-(−)-4R-hydroxy-3R-methylpiperidine as an oil. Yield 2.3 g (98%), $C_6H_{13}NO$, m/z 116 (M+1), PMR ($CD_3OD$): 0.98 (3H, d, $CH_3$, j=8 Hz), 1.6 (2H, m, $H_3$ & $H_5$), 2.04 (1H, m, $H_5$), 2.64 (1H, t, $H_2$, j=12 Hz), 2.92 (1H, dt, $H_2$, j=3 Hz, 12 Hz), 3.28 (3H, m, $H_4$ & $H_6$).

Preparation 7

Cis-4-(RS)-acetoxy-3-(SR)-methylpiperidine

A mixture of cis-1-benzyl-4-(RS)-acetoxy-3-(SR)-methylpiperidine [7 g, 28.5 mmole {prepared according to literature procedure described in A. F. Casy and W. K. Jeffery, Can.J.Chem., 50 (1972), 803}] and 20% palladium hydroxide (1.8 g) in methanol (25 ml) was stirred at 50–55° C. under hydrogen (1 atmosphere) for 20 hr. The catalyst was filtered off and washed with methanol. Filtrate was concentrated to give cis-4-(RS)-acetoxy-3-(SR)-methylpiperidine as oil. Yield 4.4 g (99%), $C_8H_{15}NO_2$, m/z 158 (M+1), PMR ($CDCl_3$): 0.94 (3H, d, $CH_3$, j=8 Hz), 1.42 (1H, m, $H_3$), 1.67 (1H, m, $H_5$), 1.98 (1H, m, $H_5$), 2.08 (3H, s, $COCH_3$), 2.31 (1H, t, $H_2$, j=12 Hz), 2.68 (1H, dt, $H_2$, j=3 Hz, 12 Hz), 3.04 (2H, m, $H_6$), 4.95 (1H, d, $H_4$, j=6 Hz).

Preparation 8

Cis-(+)-4S-acetoxy-3R-methylpiperidine

A solution of dibenzoyl L-(−)-tartaric acid monohydrate (4.42 g, 11.78 mmole) in ethyl acetate (10 ml) was added to the stirred solution of cis-4-(RS)-acetoxy-3-(SR)-methylpiperidine (3.7 g, 23.56 mole) in ethyl acetate (10 ml). The solid thus separated was filtered, washed with ethyl acetate (25 ml) and recrystallized from methanol to give dibenzoyl cis-(−)-4S-acetoxy-3R-methylpiperidine-L-tartrate. Yield 1.8 g (30%), $[\alpha]_D$ −43.8°. $C_{26}H_{29}NO_{10}$, m/z 516 (M+1), PMR ($D_2O$): 0.94 (3H, d, $CH_3$, j=8 Hz), 1.42 (1H, m, $H_3$), 1.67 (1H, m, $H_5$), 1.98 (1H, m, $H_5$), 2.08 (3H, s, $COCH_3$), 2.31 (1H, t, $H_2$, j=12 Hz), 2.68 (1H, dt, $H_2$, j=3 Hz, 12 Hz), 3.04 (2H, m, $H_6$), 4.95 (1H, m, $H_4$), 5.65 (2H, s, CH), 7.5 (4H, t, ArH, j=8 Hz), 7.65 (2H, t, ArH, j=8 Hz), 8.08 (4H, d, ArH, j=8 Hz).

Dibenzoyl cis-(−)-4S-acetoxy-3R-methylpiperidine-L-tartrate (1.8 g, 3.495 mmole) was suspended in ethyl acetate (10 ml) and basified (pH 8.5) with 10% sodium carbonate solution. Ethyl acetate layer was separated, washed with water, dried ($Na_2SO_4$) and concentrated to dryness to furnish cis-(+)-4S-acetoxy-3R-methylpiperidine as colourless oil. Yield 0.5 g (90%), $[\alpha]_D$+22°, $C_8H_{15}NO_2$, m/z 158 (M+1), PMR ($CDCl_3$): 0.94 (3H, d, $CH_3$, j=8 Hz), 1.42 (1H, m, $H_3$), 1.67 (1H, m, $H_5$), 1.98 (1H, m, $H_5$), 2.08 (3H, s, $COCH_3$), 2.31 (1H, t, $H_2$, j=12 Hz), 2.68 (1H, dt, $H_2$, j=3 Hz, 12 Hz), 3.04 (2H, m, $H_6$), 4.95 (1H, d, $H_4$, j=6 Hz).

Preparation 9

Cis-(−)-4R-acetoxy-3S-methylpiperidine

A solution of dibenzoyl D-(+)-tartaric acid (4.19 g, 11.78 mmole) in ethyl acetate (10 ml) was added to the stirred solution of cis-4-(RS)-acetoxy-3-(SR)-methylpiperidine (3.7 g, 23.56 mole) in ethyl acetate (10 ml). The salt thus separated was filtered, washed with ethyl acetate (10 ml) and recrystallized from methanol to give dibenzoyl cis-(+)-4R-acetoxy-3 S-methyl piperidine-D-tartrate. Yield 1.5 g (25%), $[\alpha]_D$+42°, $C_{26}H_{29}NO_{10}$, m/z 516 (M+1), PMR ($D_2O$): 0.94 (3H, d, $CH_3$, j=8 Hz), 1.42 (1H, m, $H_3$), 1.67 (1H, m, $H_5$), 1.98 (1H, m, $H_5$), 2.08 (3H, s, $COCH_3$), 2.31 (1H, t, $H_2$, j=12 Hz), 2.68 (1H, dt, $H_2$, j=3 Hz, 12 Hz), 3.04 (2H, m, $H_6$), 4.95 (1H, m, $H_4$), 5.65 (2H, s, CH), 7.5 (4H, t, ArH, j=8 Hz), 7.65 (2H, t, ArH, j=8 Hz), 8.08 (4H, d, ArH, j=8 Hz).

Dibenzoyl cis-(+)-4R-acetoxy-3S-methylpiperidine-D-tartrate (1.5 g, 2.913 mmole) was suspended in ethyl acetate (10 ml) and basified (pH 8.5) with 10% sodium carbonate solution. Ethyl acetate layer was separated, washed with water, dried ($Na_2SO_4$) and concentrated to afford cis-(−)-4R-acetoxy-3S-methylpiperidine. Yield 0.46 g (100%), $[\alpha]_D$−30.5°, $C_8H_{15}NO_2$, m/z 158 (M+1), PMR ($CDCl_3$): 0.94 (3H, d, $CH_3$, j=8 Hz), 1.42 (1H, m, $H_3$), 1.67 (1H, m, $H_5$), 1.98 (1H, m, $H_5$), 2.08 (3H, s, $COCH_3$), 2.31 (1H, t, $H_2$, j=12 Hz), 2.68 (1H, dt, $H_2$, j=3 Hz, 12 Hz), 3.04 (2H, m, $H_6$), 4.95 (1H, d, $H_4$, j=6 Hz).

Preparation 10

4-Hydroxy-3-trifluoromethylpiperidine 1-benzylpiperidin-4-one (12 g, 63.5 mmole) was added to the stirred suspension of sodium hydride (3.0 g, 127.0 mmole) in tetrahydrofuran (100 ml) at −5° C. The reaction mixture was stirred for 15 min, trifluoromethyl iodide (25 g, 127.0 mmole) was bubbled over a period of 4 hr at −5° C. and stirring continued for 1 hr. The resulting mixture was stirred for 16 hr at ambient temperature, saturated sodium sulphate solution (20 ml) was added and diluted with ethyl acetate (200 ml). Ethyl acetate layer was separated, dried ($Na_2SO_4$) and concentrated to furnish crude product, which was purified through column chromatography. Elute from hexane afforded 1-benzyl-3-trifluoromethylpiperidin-4-one as oil and 20% ethyl acetate in hexane gave the unreacted 1-benzylpiperidin-4-one (9.5 g). Yield 2.1 g (44%, based on reacted 1-benzyl piperidin-4-one), $C_{13}H_{14}F_3NO$, m/z 258 (M+1), PMR ($CDCl_3$): 2.54 (2H, m, $H_6$), 3.02 (2H, m, $H_2$), 3.6 (3H, m, $H_3$ & $H_5$), 4.36 (2H, s, N—$CH_2$), 7.28 (5H, m, ArH).

Sodium borohydride (0.6 g, 16.0 mmole) was added to the stirred solution of 1-benzyl-3-trifluoromethylpiperidin-4-one (2.1 g, 8.2 mmole) in methanol (25 ml) at 0–5° C. over a period of 5 min, and stirring was continued for 2 hr at ambient temperature. The reaction mixture was concentrated to dryness, triturated with water (20 ml) and extracted with chloroform. The chloroform extract was dried over sodium sulphate and concentrated to dryness to furnish 1-benzyl-4-hydroxy-3-trifluoromethylpiperidine as oil. Yield 1.8 g (85%), $C_{13}H_{16}F_3NO$, m/z 259 (M+1).

A mixture of 1-benzyl-4-hydroxy-3-trifluoromethylpiperidine (1.8 g, 6.94 mmole and 20% palladium hydroxide (0.5 g) in methanol (25 ml) was stirred in hydrogen atmosphere (1.atm.) for 17 hr at 50° C. Catalyst was filtered off, washed with methanol, filtrate was concentrated to dryness to give 4-hydroxy-3-trifluoromethylpiperidine as oil. Yield 0.7 g (60%), C6H10F3NO, m/z 170 (M+1).

Preparation 11

3,3-Dimethyl-4-hydroxypiperidine

Sodium borohydride (0.456 g, 12.0 mmole) was added to the stirred solution of 1-benzyl-3,3-dimethylpiperidin-4-one [{prepared according to literature procedure described in U.S. Pat. No. 5,846,980} 5.4 g, 24.0 mmole] in methanol (25 ml) at 0–5° C. over a period of 15 min, and stirring was continued for 30 min. The reaction mixture was concentrated to dryness, triturated with water (25 ml) and extracted with ethyl acetate (2×100 ml). The extract was dried (sodium sulphate) and concentrated to dryness to furnish 1-benzyl-3,3-dimethyl-4-hydroxypiperidine as oil. Yield 5.2 g (96%), $C_{14}H_{21}NO$, m/z 220 (M+1), PMR ($CDCl_3$): 0.83 (3H, s, $CH_3$), 1.13 (3H, s, $CH_3$), 1.29 (1H, m, $H_5$), 1.62–1.9 (2H, m, $H_2$ & $H_5$), 2.14 (1H, m, $H_6$), 2.38 (1H, d, $H_2$, j=12 Hz), 2.8 (1H, m, $H_6$), 3.12 (1H, m, $H_4$), 3.46 (2H, s, N—$CH_2$), 7.3 (5H, m, ArH).

A mixture of 1-benzyl-3,3-dimethyl-4-hydroxypiperidine (5.0 g, 22.0 mmole) and 20% palladium hydroxide (1.5 g) in methanol (100 ml) was stirred at 50–55° C. in hydrogen atmosphere (1 atm.) for 20 hr. Catalyst was filtered off, washed with methanol, filtrate was concentrated to dryness to give 3,3-dimethyl-4-hydroxypiperidine as oil. Yield 2.9 g (94%), $C_7H_{15}NO$, m/z 130 (M+1), PMR ($CDCl_3$): 0.83 (3H, s, $CH_3$), 1.13 (3H, s, $CH_3$), 1.29 (1H, m, $H_5$), 1.45–1.9 (2H, m, $H_5$ & $H_6$), 2.4 (1H, d, $H_2$, j=12 Hz), 2.68 (1H, d, $H_2$, j=12 Hz), 3.08 (1H, m, $H_6$), 3.4 (1H, dd, $H_4$, j=6 Hz & 12 Hz).

Preparation 12

3-Ethyl-4-hydroxypiperidine

Sodium borohydride (0.456 g, 12.0 mmole) was added to the stirred solution of 1-benzyl-3-ethyl piperidin-4-one (5.4 g, 24.0 mmole) in methanol (25 ml) at 0–5° C. over a period of 15 min, and stirring was continued for 30 min at ambient temperature. The reaction mixture was concentrated to dryness, triturated with water (25 ml) and extracted with ethyl acetate (2×100 ml). The extract was dried (sodium sulphate) and concentrated to dryness to furnish 1-benzyl-3-ethyl-4-hydroxypiperidine product as oil, which was used as such in the next step. Yield 5.2 g (96%), $C_{14}H_{21}NO$, m/z 220 (M+1).

A mixture of 1-benzyl-3-ethyl-4-hydroxypiperidine (5.0 g, 22.0 mmole) and palladium hydroxide (1.5 g) in methanol (100 ml) was stirred at 5.0 g, 22.0 mmole) and palladium hydroxide (1.5 g) in methanol (100 ml) was stirred at 50–55° C. in hydrogen atmosphere (1 atm.) for 20 hr. The catalyst was filtered off, washed with methanol, and filtrate was concentrated to dryness to give 3-ethyl-4-hydroxypiperidine as oil. Yield 2.9 g (94%), $C_7H_{15}NO$, m/z 130 (M+1).

Preparation 13

3,3-Diethyl-4-hydroxypiperidine

Sodium borohydride (0.3 g, 8.13 mmole) was added to the stirred solution of 1-benzyl-3,3-diethylpiperidin-4-one (4.0 g, 16.26 mmole) in methanol (22 ml) at 0–5° C. over a period of 15 min, and stirring was continued for 30 min. The reaction mixture was concentrated to dryness, triturated with water (25 ml) and extracted with ethyl acetate (2×100 ml). The extract was dried (sodium sulphate) and concentrated to dryness to furnish 1-benzyl-3,3-diethyl-4-hydroxypiperidine as oil. Yield 3.9 g (97%), $C_{16}H_{24}NO$, m/z 248 (M+1).

A mixture of 1-benzyl-3,3-diethyl-4-hydroxypiperidine (3.9 g, 15.85 mmole) and 20% palladium hydroxide (1.0 g) in methanol (100 ml) was stirred at 40° C. in hydrogen atmosphere (3.5 atm.) for 6 hr. Catalyst was filtered off, washed with methanol, filtrate was concentrated to dryness to give 3,3-diethyl-4-hydroxypiperidine as oil. Yield 1.8 g (73%), $C_9H_{19}NO$, m/z 158 (M+1).

Preparation 14

3,5-Dimethyl-4-hydroxypiperidine

Sodium borohydride (6.5 g, 0.173 mole) was added to the stirred solution of 1-benzyl-3,5-dimethylpiperidin-4-one (25.0 g, 0.15 mole) in methanol (200 ml) at 5–10° C. over a period of 30 min, and stirring was continued for 30 min at 35° C. The reaction mixture was concentrated to dryness, triturated with water (50 ml) and extracted with chloroform (2×50 ml). The extract was dried ($Na_2SO_4$) and concentrated to dryness to finish 1-benzyl-3,5-dimethyl-4-hydroxypiperidine as oil. Yield 25.0 g (99%), $C_{14}H_{21}NO$, m/z 220 (M+1).

A mixture of 1-benzyl-3,5-dimethyl-4-hydroxypiperidine (1.0 g, 4.56 mmole) and 20% palladium hydroxide (0.3 g) in methanol (20 ml) was stirred at room temperature in hydrogen atmosphere (1 atm.) for 4 hr. Catalyst was filtered off, washed with methanol, filtrate was concentrated to dryness to give 3,5-dimethyl-4-hydroxypiperidine. Yield 0.5 g (90%), $C_7H_{15}NO$, m/z 130 (M+1), PMR ($CDCl_3$): 0.9 (6H, m, 2×$CH_3$), 1.44 (1H, m, $H_3$), 1.7 (1H, m, $H_5$), 2.3 (1H, m, $H_6$), 2.46–2.84 (2H, m, $H_2$ & $H_6$), 2.98 (1H, m, $H_2$), 3.3–3.7 (1H, m, $H_4$).

Preparation 15

4-Acetoxy-1-benzyl-3,5-dimethylpiperidine

A mixture of N-benzyl-4-hydroxy-3,5-dimethylpiperidine (21.9 g, 0.1 mole), acetic anhydride (15.3 g), N,N-dimethyl-4-aminopyridine (0.01 g) and pyridine (100 ml) was stirred at 110° C. for 2 hr. The reaction mixture was concentrated to dryness, triturated with water (50 ml) and extracted with chloroform (2×50 ml). The extract was dried ($Na_2SO_4$) and concentrated to dryness to furnish a crude mixture of cis- and trans-4-acetoxy-1-benzyl-3,5-dimethylpiperidine. Yield 16 g (61.3%), $C_{16}H_{23}NO_2$, m/z 262 (M+1).

The obtained mixture of cis- and trans-4-acetoxy-1-benzyl-3,5-dimethylpiperidine was separated by silica column chromatography. Elute from 5% ethyl acetate in hexane gave trans-4-acetoxy-1-benzyl-3,5-dimethylpiperidine. Yield 9.2 g (30.9%), m.p. 43° C., $C_{16}H_{23}NO_2$, m/z 262 (M+1), PMR ($CDCl_3$): 0.88 (6H, d, 2×$CH_3$, j=6 $H_Z$), 1.68–1.92 (4H, m, $H_2$, $H_3$, $H_5$ & $H_6$), 2.08 (3H, s, $COCH_3$), 2.83 (2H, d, $H_2$ & $H_6$, j=8 $H_Z$), 3.46 (2H, s, $CH_2$—Ar), 4.28 (1H, t, $H_4$, j=12 $H_Z$), 7.24–7.4 (5H, m, Ph).

Elute from 10% ethyl acetate in hexane gave cis-4-acetoxy-1-benzyl-3,5-dimethylpiperidine. Yield 5.0 g (16.8%), m.p. 48° C. $C_{16}H_{23}NO_2$, m/z 262 (M+1), PMR ($CDCl_3$): 0.78 (6H, d, 2×$CH_3$, j=6 Hz), 1.86–2.02 (4H, m, $H_2$, $H_3$, $H_5$ & $H_6$), 2.1 (3H, s, $COCH_3$), 2.55 (2H, d, $H_2$ & $H_6$, j=8 $H_Z$), 3.52 (2H, s, $CH_2$—Ar), 5.08 (1H, s, $H_4$), 7.21–7.4 (5H, m, Ph).

Preparation 16

Trans-3,5-Dimethyl-4-hydroxypiperidine

The obtained trans-4-acetoxy-1-benzyl-3,5-dimethylpiperidine (9.2 g, 0.035 mole) was refluxed with a mixture of ethanol (10 ml) and aqueous 5 N NaOH (50 ml) for 24 hr, cooled, diluted with water and extracted with ethyl acetate (2×50 ml).

The extract was washed with water, dried (sodium sulphate), concentrated to furnish trans-1-benzyl-4-hydroxy-3,5-dimethylpiperidine. Yield 7.72 g (100%), m.p. 85° C., $C_{14}H_{21}NO$, m/z 220 (M+1), PMR ($CDCl_3$): 0.9 (6H, d, 2×$CH_3$, j=6 $H_Z$), 1.42 (1H, bs, OH, $D_2O$ exchangeable), 1.64–1.9 (4H, m, $H_2$, $H_3$, $H_5$ & $H_6$), 2.66 (1H, t, $H_4$, j=12 $H_Z$), 2.81 (2H, d, $H_2$ & $H_6$, j=8 $H_Z$), 3.44 (2H, s, $CH_2$—Ar), 7.22–7.4 (5H, m, Ph).

A mixture of trans-1-benzyl-3,5-dimethyl-4-hydroxypiperidine (7.72 g, 0.0353 mole) and 20% palladium hydroxide (1.0 g) in methanol (80 ml) was stirred at room temperature in hydrogen atmosphere (3 atm.) for 15 hr. Catalyst was filtered off, washed with methanol, filtrate was concentrated to dryness to give trans-3,5-dimethyl-4-hydroxypiperidine. Yield 4.54 g (100%), m.p. 120–22° C., $C_7H_{15}NO$, m/z 130 (M+1), PMR ($CDCl_3$): 0.95 (6H, m, 2×$CH_3$), 1.4–1.7 (4H, m, $H_3$, $H_5$, NH & OH, 2H $D_2O$ exchangeable), 2.3 (2H, m, $H_2$ & $H_6$), 2.76 (1H, t, $H_4$, j=12 $H_Z$), 3.02 (2H, m, $H_2$ & $H_6$).

Preparation 17

Cis-3,5-Dimethyl-4-hydroxypiperidine

The obtained cis-4-acetoxy-1-benzyl-3,5-dimethylpiperidine (4.9 g, 0.0188 mole) was refluxed with a mixture of ethanol (8 ml) and aqueous 5 N NaOH (40 ml) for 24 hr, cooled, diluted with water and extracted with ethyl acetate (2×50 ml). The extract was washed with water, dried (sodium sulphate), concentrated to furnish cis-1-benzyl-4-hydroxy-3,5-dimethylpiperidine. Yield 4.11 g (100%), m.p. 60° C., $C_{14}H_{21}NO$, m/z 220 (M+1), PMR ($CDCl_3$): 0.9 (6H, d, 2×$CH_3$, j=6 $H_Z$), 1.64 (1H, bs, OH, $D_2O$ exchangeable), 1.8–2.05 (4H, m, $H_2$, $H_3$, $H_5$ & $H_6$), 2.5 (2H, d, $H_2$ & $H_6$, j=8 $H_Z$), 3.48 (2H, s, $CH_2$—Ar), 3.54 (1H, t, $H_4$, j=12 Hz), 7.24–7.4 (5H, m, Ph).

A mixture of cis-1-benzyl-3,5-dimethyl-4-hydroxypiperidine (4.11 g, 0.01877 mole) and 20% palladium hydroxide (0.5 g) in methanol (50 ml) was stirred at room temperature in hydrogen atmosphere (3 atm.) for 15 hr. Catalyst was filtered off, washed with methanol, filtrate was concentrated to dryness to give cis-3,5-dimethyl-4-hydroxypiperidine. Yield 2.1 g (86.8%), m.p. 162–64° C., $C_7H_{15}NO$, m/z 130 (M+1), PMR ($CDCl_3$): 0.94 (6H, m, 2×$CH_3$), 1.68–1.84 (2H, m, $H_3$ & $H_5$), 2.5 (2H, m, NH & OH $D_2O$ exchangeable), 2.48–2.72 (4H, m, $H_2$ & $H_6$), 3.62 (1H, s, $H_4$).

Preparation 18

3-Ethyl-4-hydroxy-3-methylpiperidine

Method 1

1-Benzyl-3-methyl-piperidin-4-one (50 g, 246 mmole) was added to the stirred suspension of sodium hydride (12.0 g, 300.0 mmole) in tetrahydrofuran (500 ml) at ambient temperature and stirring was continued for 1 hr. Ethyl iodide (42.5 ml, 520.0 mmole) in dry tetrahydrofuran (100 ml) was added it at 0–5° C. The resulting mixture stirred at room temperature for 18 hr, water (100 ml) and ethyl acetate (800 ml) were added respectively. Organic layer was separated, dried ($Na_2SO_4$) and concentrated to give crude product, which was purified through column chromatography. Elute from 5% ethyl acetate in hexane afforded 1-benzyl-3,5-diethyl-3-methylpiperidin-4-one. Yield 12.0 g (19%), $C_{17}H_{25}NO$, m/z 260 (M+1).

Elution from 10% ethyl acetate in hexane gave 1-benzyl-3-ethyl-3-methylpiperidin-4-one as oil, which was used in the next step. Yield 25.0 g (46%) $C_{15}H_{21}NO$, m/z 232 (M+1).

Method 2

1-Benzyl-3-ethylpiperidin-4-one (2 g, 9.2 mmole) was added to the stirred suspension of potassium tert.-butoxide (1.5 g, 13.3 mmole) in tetrahydrofuran (25 ml) at 0° C. The reaction mixture was stirred for 15 min, methyl iodide (2 g, 14.1 mmole) was added over a period of 10 min at 0° C. and stirring continued for 1 hr. The resulting mixture was stirred for 16 hr at ambient temperature, water (25 ml) was added and extracted with ethyl acetate (100 ml). Ethyl acetate layer on concentrated furnished 1-benzyl-3-ethyl-3-methylpiperid-4-one as oil, which was used as such in the next step. Yield 1.5 g (71%), $C_{15}H_2NO$, m/z 232 (M+1).

Sodium borohydride (0.3 g, 9.0 mmole) was added to the stirred solution of the 1-benzyl-3-ethyl-3-methylpiperid-4-one (1.5 g, 6.5 mmole) in methanol (20 ml) at 0–5° C. over a period of 5 min, and stirring was continued for 2 hr at ambient temperature. The reaction mixture was concentrated to dryness, triturated with water (20 ml) and extracted with ethyl acetate (2×50 ml). The extract was dried over sodium sulphate and concentrated to dryness to furnish 1-benzyl-3-ethyl-4-hydroxy-3-methylpiperidine product as oil, which was used as such in the next step. Yield 1.1 g (74%), $C_{15}H_{23}NO$, m/z 234 (M+1).

A mixture of 1-benzyl-3-ethyl-4-hydroxy-3-methylpiperidine (1.1 g, 4.74 mmole) and 20% palladium hydroxide (0.4 g) in methanol (20 ml) was stirred at ambient temperature in hydrogen atmosphere (1 atm.) for 20 hr. Catalyst was filtered off, washed with methanol, filtrate was concentrated to dryness to give 3-ethyl-4-hydroxy-3-methylpiperidine as oil. Yield 0.6 g (90%), $C_8H_{17}NO$, m/z 144 (M+1), PMR ($CDCl_3$): 0.7–1.06 (6H, m, 2×$CH_3$), 1.24–2.0 (5H, m, $CH_2$, $H_5$, NH & OH, NH & OH $D_2O$ exchangeable), 2.3 (1H, m, $H_5$), 2.62–3.18 (2H, m, $H_2$), 3.3–3.8 (3H, m, $H_4$ & $H_6$).

Preparation 19

4-Hydroxy-3-n-propylpiperidine 1-benzylpiperidin-4-one (10 g, 53.0 mmole) was added to the stirred suspension of potassium tert. butoxide (6.0 g, 54.0 mmole) in tetrahydrofuran (50 ml) at 10° C. The reaction mixture was stirred for 15 min, n-propyl iodide (13 g, 76.0 mmole) was added at 10° C. The resulting mixture allowed coming at room temperature and stirred for 16 hr and concentrated to dryness. The residue was triturated with water, extracted with ethyl acetate, dried ($Na_2SO_4$) and concentrated to give a mixture of 1-benzyl-3-n-propylpiperidin-4-one and 1-benzyl-3,3-n-dipropylpiperidin-4-one, which were separated through column chromatography. Elute from 10% ethyl acetate in hexane afforded 1-benzyl-3-n-propylpiperidin-4-one. Yield 4.0 g (33%), $C_{15}H_{21}NO$, m/z 232 (M+1).

Further elution from 10% ethyl acetate in hexane furnished 1-benzyl-3,3-n,n-dipropylpiperidin-4-one as oil. Yield 3.1 g (22%), $C_{18}H_{27}NO$, m/z 274 (M+1).

Sodium borohydride (0.5 g, 15.6 mmole) was added to the stirred solution of 1-benzyl-3-n-propylpiperidin-4-one (4.0 g, 17.3 mmole) in methanol (25 ml) at 0–5° C. over a period of 5 min, and stirring was continued for 1 hr at ambient temperature. The reaction mixture was concentrated to dryness, triturated with water (20 ml) and extracted with ethyl acetate. The ethyl acetate extract was dried ($Na_2SO_4$) and concentrated to dryness to furnish 1-benzyl-4-hydroxy-3-n-propylpiperidine as oil. Yield 3.3 g (81%), $C_{15}H_{23}NO$, m/z 234 (M+l).

A mixture of 1-benzyl-4-hydroxy-3-n-propylpiperidine (3.3 g, 14.16 mmole) and 20% palladium hydroxide (0.25 g) in methanol (25 ml) was stirred in hydrogen atmosphere (1 atm.) for 24 hr at 30° C. Catalyst was filtered off, washed with methanol, filtrate was concentrated to dryness to give 4-hydroxy-3-n-propylpiperidine as oil. Yield 1.8 g (90%), $C_8H_{17}NO$, m/z 144 (M+1), PMR ($CDCl_3$): 0.92 (3H, t, $CH_3$, j=8 Hz), 1.2–1.52 (5H, m, 2×$CH_2$ & $H_3$), 1.72 (1H, m, $H_5$), 1.94 (2H, m, $H_5$, & OH, $D_2O$ exchangeable), 2.22 (1H, m, $H_2$), 2.62 (1H, m, $H_6$), 3.12 (1H, m, $H_2$), 3.3 (1H, m, $H_6$), 3.5 (1H, bs, NH, $D_2O$ exchangeable), 3.98 (1H, m, $H_4$).

Preparation 20

3,3-Di-n-propyl-4-hydroxypiperidine

Sodium borohydride (0.4 g, 10.8 mmole) was added to the stirred solution of 1-benzyl-3,3-n,n-dipropylpiperidin-4-one (3.1 g, 11.35 mmole) in methanol (25 ml) at 0–5° C. over a period of 15 min, and stirring was continued for 30 min. The reaction mixture was concentrated to dryness, triturated with water (25 ml) and extracted with ethyl acetate (2×100 ml). The extract was dried (sodium sulphate) and concentrated to dryness to furnish 1-benzyl-3,3-di-n-propyl-4-hydroxypiperidine as oil. Yield 2.7 g (86%), $C_{18}H_{29}NO$, m/z 276 (M+1).

A mixture of 1-benzyl-3,3-di-n-propyl-4-hydroxypiperidine (0.9 g, 3.27 mmole) and 20% palladium hydroxide (0.2 g) in methanol (20 ml) was stirred at ambient temperature in hydrogen atmosphere (1 atm.) for 8 hr. Catalyst was filtered off, washed with methanol, filtrate was concentrated to dryness to give 3,3-di-n-propyl-4-hydroxypiperidine as oil. Yield 0.5 g (84%), $C_{12}H_{23}NO$, m/z 186 (M+1).

Preparation 21

4-Hydroxy-3-isopropylpiperidine 1-benzylpiperidin-4-one (10 g, 53.0 mmole) was added to the stirred suspension of potassium tert. butoxide (6.0 g, 54.0 mmole) in tetrahydrofuran (50 ml) at 10° C. The reaction mixture was stirred for 15 min, isopropyl iodide (10 g, 54.0 mmole) was added at 10° C. The resulting mixture allowed coming at room temperature and stirred for 16 hr, refluxed for 3 hr and concentrated to dryness. The residue was triturated with water, extracted with ethyl acetate, dried ($Na_2SO_4$) and concentrated to give crude product, which was purified through column chromatography. Elute from 10% ethyl acetate in hexane afforded 1-benzyl-3-isopropylpiperid-4-one. Yield 3.3 g (28%), $C_{15}H_{21}NO$, m/z 232 (M+1).

Sodium borohydride (0.5 g, 15.6 mmole) was added to the stirred solution of 1-benzyl-3-isopropylpiperid-4-one (3.3 g, 14.2 mmole) in methanol (25 ml) at 0–5° C. over a period of 5 min, and stirring was continued for 1 hr at ambient temperature. The reaction mixture was concentrated to dryness, triturated with water (20 ml) and extracted with ethyl acetate. The ethyl acetate extract was dried ($Na_2SO_4$) and concentrated to dryness to furnish 1-benzyl-4-hydroxy-3-isopropylpiperidine as oil. Yield 2.9 g (85%), $C_{15}H_{23}NO$, m/z 234 (M+1).

A mixture of 1-benzyl-4-hydroxy-3-isopropylpiperidine (2.9 g, 12.44 mmole) and 20% palladium hydroxide (0.25 g) in methanol (25 ml) was stirred in hydrogen atmosphere (1 atm.) for 24 hr at 30° C. Catalyst was filtered off, washed with methanol, filtrate was concentrated to dryness to give 4-hydroxy-3-isopropylpiperidine as oil. Yield 1.6 g (80%), C8H17NO, m/z 144 (M+1) PMR (CDCl3): 0.9 (6H, m, 2×CH3), 1.1–1.64 (2H, m, CH & H3), 1.66–2.42 (3H, m, H5, & OH, D2O exchangeable), 2.62 (1H, m, H2), 3.02 (2H, m, H6), 3.45 (1H, bs, NH, D2O exchangeable), 3.54 (1H, m, H6), 4.18 (1H, m, H4).

Preparation 22

3-n-But-4-hydroxpiperidine 1-benzylpiperidin-4-one (10 g, 53.0 mmole) was added to the stirred suspension of potassium tert. butoxide (6.0 g, 54.0 mmole) in tetrahydrofuran (50 ml) at 10° C. The reaction mixture was stirred for 15 min, n-butyl iodide (13 g, 70.6 mmole) was added at 10° C. The resulting mixture allowed coming at room temperature and stirred for 48 hr and concentrated to dryness. The residue was triturated with water, extracted with ethyl acetate, dried ($Na_2SO_4$) and concentrated to give a mixture of 1-benzyl-3-n-butylpiperidin-4-one and 1-benzyl-3,3-n,n-dibutylpiperidin-4-one, which were separated through column chromatography. Elute from 10% ethyl acetate in hexane afforded 1-benzyl-3-n-butylpiperidin-4-one. Yield 2.8 g (22%), $C_{16}H_{23}NO$, m/z 246 (M+1).

Further elution from 10% ethyl acetate in hexane furnished 1-benzyl-3,3-n,n-dibutylpiperidin-4-one as oil. Yield 3.8 g (28%), $C_{20}H_{31}NO$, m/z 302 (M+1).

Sodium borohydride (0.4 g, 12.2 mmole) was added to the stirred solution of 1-benzyl-3-n-butylpiperidin-4-one (2.8 g, 9.3 mmole) in methanol (20 ml) at 0–5° C. over a period of 5 min, and stirring was continued for 1 hr at ambient temperature. The reaction mixture was concentrated to dryness, triturated with water (20 ml) and extracted with ethyl acetate. The ethyl acetate extract was dried ($Na_2SO_4$) and concentrated to dryness to furnish 1-benzyl-3-n-butyl-4-hydroxypiperidine as oil. Yield 2.5 g (86%), $C_{16}H_{25}NO$, m/z 248 (M+1).

A mixture of 1-benzyl-3-n-butyl-4-hydroxypiperidine (2.5 g, 10.0 mmole) and 20% palladium hydroxide (0.2 g) in methanol (25 ml) was stirred in hydrogen atmosphere (1 atm.) for 24 hr at 30° C. Catalyst was filtered off, washed with methanol, filtrate was concentrated to dryness to give 3-n-butyl-4-hydroxypiperidine as oil. Yield 1.4 g (87%), C9H19NO, m/z 158 (M+1) PMR (CDCl3): 0.94 (3H, t, CH3, j=8 Hz), 1.04–1.54 (7H, m, 3×CH2 & H3), 1.74 (1H, m, H5), 1.98 (2H, m, H5, & OH, D2O exchangeable), 2.22 (1H, m, H2), 2.7 (1H, m, H6), 3.12 (1H, m, H2), 3.3 (1H, m, H6), 3.46 (1H, bs, NH, D2O exchangeable), 3.98 (1H, m, H4).

Preparation 23

3,3-Di-n-butyl-4-hydroxypiperidine

Sodium borohydride (0.5 g, 15.6 mmole) was added to the stirred solution of 1-benzyl-3,3-n,n-dibutylpiperidin-4-one (3.8 g, 12.6 mmole) in methanol (25 ml) at 0–5° C. over a period of 15 min, and stirring was continued for 30 min. The reaction mixture was concentrated to dryness, triturated with water (25 ml) and extracted with ethyl acetate (2×100 ml). The extract was dried (sodium sulphate) and concentrated to dryness to furnish 1-benzyl-3,3-di-n-butyl-4-hydroxy-piperidine as oil. Yield 3.0 g (78%), $C_{20}H_{33}NO$, m/z 304 (M+1).

A mixture of 1-benzyl-3,3-di-n-butyl-4-hydroxypiperidine (0.9 g, 2.97 mmole) and 20% palladium hydroxide (0.2 g) in methanol (20 ml) was stirred at ambient temperature in hydrogen atmosphere (1 atm.) for 8 hr. Catalyst was filtered off, washed with methanol, filtrate was concentrated to dryness to give 3,3-di-n-butyl-4-hydroxypiperidine as oil. Yield 0.5 g (85%), $C_{14}H_{27}NO$, m/z 214 (M+1).

Preparation 24

4-Hydroxy-3-isobutylpiperidine 1-benzylpiperidin-4-one (10 g, 53.0 mmole) was added to the stirred suspension of potassium tert. butoxide (7.0 g, 59.0 mmole) in tetrahydrofuran (50 ml) at 10° C. The reaction mixture was stirred for 15 min, isobutyl iodide (10.0 g, 54.0 mmole) was added at 10° C. The resulting mixture stirred for 16 hr at room temperature, refluxed for 3 hr and concentrated to dryness. The residue was triturated with water, extracted with ethyl acetate, dried ($Na_2SO_4$) and concentrated to give crude product, which was purified through column chromatography. Elute from 10% ethyl acetate in hexane afforded 1-benzyl-3-isobutylpiperidin-4-one. Yield 1.0 g (9%), $C_{16}H_{23}NO$, m/z 246 (M+1).

Sodium borohydride (0.3 g, 9.0 mmole) was added to the stirred solution of 1-benzyl-3-isobutylpiperidin-4-one (1.0 g, 4.0 mmole) in methanol (10 ml) at 0–5° C. over a period of 5 min, and stirring was continued for 1 hr at ambient temperature. The reaction mixture was concentrated to dryness, triturated with water (20 ml) and extracted with ethyl acetate. The ethyl acetate extract was dried ($Na_2SO_4$) and concentrated to dryness to furnish 1-benzyl-4-hydroxy-3-isobutylpiperidine as oil. Yield 0.63 g (54%), $C_{16}H_{25}NO$, m/z 248 (M+1).

A mixture of 1-benzyl-4-hydroxy-3-isobutylpiperidine (0.63 g, 2.5 mmole) and 20% palladium hydroxide (0.1 g) in methanol (20 ml) was stirred in hydrogen atmosphere (1 atm.) for 48 hr at 35° C. Catalyst was filtered off, washed with methanol, filtrate was concentrated to dryness to give 4-hydroxy-3-isobutylpiperidine as oil. Yield 0.35 g (91%), C9H19NO, m/z 158 (M+1).

Preparation 25

3-Benzyl-4-hydroxypiperidine

1-Benzylpiperidin-4-one (10 g, 53.0 mmole) was added to the stirred suspension of sodium hydride (1.8 g, 53.0 mmole) in tetrahydrofuran (50 ml) at 10° C. The reaction mixture was stirred for 15 min, benzyl bromide (9.0 g, 53.0 mmole) was added at 10° C. The resulting mixture stirred at room temperature for 4 hr and concentrated to dryness. The residue was triturated with water, extracted with ethyl acetate, dried ($Na_2SO_4$) and concentrated to give crude product, which was purified through column chromatography. Elute from 10% ethyl acetate in hexane afforded 1,3-dibenzylpiperidin-4-one. Yield 1.8 g (13%), $C_{19}H_{21}NO$, m/z 280 (M+1), PMR ($CDCl_3$): 2.22–2.62 (4H, m, $H_2$ & $H_6$), 2.86 (2H, m, $H_5$), 3.2 (1H, dd, $H_3$, j=12 Hz), 3.45 (2H, m, $CH_2Ar$), 3.68 (2H, m, N—$CH_2Ar$), 7.1–7.4 (10, m, ArH).

Sodium borohydride (0.3 g, 9.0 mmole) was added to the stirred solution of 1,3-dibenzylpiperidin-4-one (1.8 g, 6.45 mmole) in methanol (25 ml) at 0–5° C. over a period of 5 min, and stirring was continued for 1 hr at ambient temperature. The reaction mixture was concentrated to dryness, triturated with water (20 ml) and extracted with ethyl acetate. The ethyl acetate extract was dried ($Na_2SO_4$) and concentrated to dryness to furnish 1,3-dibenzyl-4-hydroxypiperidine as oil. Yield 1.7 g (91%), $C_{19}H_{23}NO$, m/z 282 (M+1).

A mixture of 1,3-dibenzyl-4-hydroxypiperidine (1.7 g, 6.0 mmole) and 20% palladium hydroxide (0.3 g) in methanol (20 ml) was stirred in hydrogen atmosphere (1 atm.) for 12 hr at 35° C. Catalyst was filtered off, washed with methanol, filtrate was concentrated to dryness to give 4-hydroxy-3-benzylpiperidine as oil. Yield 1.0 g (91%), C12H17NO, m/z 192 (M+1) PMR (CDCl3): 1.66 (1H, m, H3), 1.94 (1H, m, H5), 2.26 (2H, m, H5, & OH, D2O exchangeable), 2.62 (1H, m, H2), 2.74 (1H, m, H6), 3.02 (1H, m, H2), 3.34 (1H, m, H6), 3.52 (1H, bs, NH, D2O exchangeable), 3.9 (1H, m, H4), 4.74 (2H, m, CH2-Ar), 7.28 (5H, m, ArH).

Preparation 26

3-t-Butoxycarbonylaminomethyl-4-hydroxypiperidine

A mixture of ethyl 3-(N-benzylamino)propionate (5.0 g, 24.15 mmole) and acrylonitrile (1.473 g, 27.77 mmole) was heated at 90° C. for 24 hr, concentrated in vacuum to remove unreacted reagents to furnish ethyl 3-(N-benzyl amino-N-cyanoethyl) propionate as viscous oil. Yield 6.1 g (97%), $C_{15}H_{20}N_2O_2$, m/z 261 (M+1), PMR (CDCl$_3$): 1.26 (3H, t, CH$_3$, J=8 Hz), 2.32–2.62 (4H, m, 2×CH$_2$), 2.74–3.0 (4H, m, 2×NCH$_2$), 3.65 (2H, s, CH$_2$—Ar), 4.15 (2H, q, OCH$_2$, J=8 Hz), 7.32 (5H, m, ArH).

A solution of ethyl 3-(N-benzylamino-N-cyanoethyl) propionate (7.5 g, 28.85 mmole) in dry xylene (20 ml) was added dropwise to the stirred suspension of sodium hydride (1.384 g) in dry xylene (40 ml). The resulting mixture was stirred at 120° C. for 2 hr, cooled at 5° C., acidified with Conc. HCl (pH 2) and extracted with ethyl acetate. Ethyl extract was concentrated to give 1-benzyl-3-cyanopiperidin-4-one. Yield 6.0 g (97%), $C_{13}H_{14}N_2O$, m/z 215 (M+1).

Sodium borohydride (0.89 g, 23.37 mmole) was added to the stirred solution of 1-benzyl-3-cyanopiperidin-4-one (2.5 g, 11.68 mmole) in ethanol (125 ml) at 0° C. over a period of 30 min, and stirring was continued for 2 hr at 5° C. The reaction mixture was concentrated to dryness, triturated with water (20 ml) and extracted with ethyl acetate. The extract was concentrated to dryness to furnish 1-benzyl-3-cyano-4-hydroxypiperidine product as oil. Yield 1.85 g (73%) $C_{13}H_{16}N_2O$, m/z 217 (M+1), PMR (CDCl$_3$): 1.78 (2H, m, H$_5$), 2.22 (1H, m, H$_3$), 2.6–3.12 (4H, m, H$_2$ & H$_6$), 3.58 (1H, m, H$_4$), 3.65 (2H, s, CH$_2$—Ar), 7.32 (5H, s, ArH).

A mixture of 1-benzyl-3-cyano-4-hydroxypiperidine (2.3 g, 10.64 mmole) and lithium aluminum hydride (0.6 g, 15.97 mmole) in dry tetrahydrofuran (50 ml) was refluxed for 2 hr. The reaction mixture was cooled at 5° C. and quenched with water, aqueous NaOH (10%) and filtered. Filtrate was concentrated to dryness to afford crude 3-aminomethyl-1-benzyl-4-hydroxypiperidine. Yield 2.1 g (89.6%) $C_{13}H_{20}N_2O$, m/z 221 (M+1), PMR (CDCl$_3$): 1.1–1.9 (3H, m, H$_3$ & H$_5$), 2.1 (1H, m, H$_6$), 2.82 (2H, m, H$_2$), 3.4–3.96 (3H, m, H$_6$ & CH$_2$NH$_2$), 4.16 (1H, m, H$_4$), 4.84 (2H, s, N—CH$_2$Ar), 7.34 (5H, m, ArH).

Di-t-butoxycarbonate (2.5 g, 11.45 mmole) was added to the stirred solution of crude 3-aminomethyl-1-benzyl-4-hydroxypiperidine (2.1 g, 9.55 mmole) in a mixture of dioxane-water (80 ml; 2:1) at ambient temperature. The reaction mixture was stirred for 2 hr, concentrated in vacuum to dryness to give 1-benzyl-3-t-butoxycarbonylaminomethyl-4-hydroxypiperidine. Yield 2.5 g (82%), $C_{19}H_{28}N_2O_3$, m/z 321 (M+1).

A mixture of 1-benzyl-3-t-butoxycarbonylaminomethyl-4-hydroxypiperidine (2.0 g, 6.25 mmole) and 5% palladium on carbon (0.4 g) in methanol (30 ml) was stirred at ambient temperature in hydrogen atmosphere (1 atm.) for 8 hr. The catalyst was filtered off, washed with methanol, and filtrate was concentrated to dryness to afford 3-t-butoxyaminomethyl-4-hydroxypiperidine as oil. Yield 0.8 g (56%), $C_{11}H_{22}N_2O_3$, m/z 231 (M+1), PMR (CDCl$_3$): 1.4 (9H, S, 3×CH$_3$), 1.6–2.08 (3H, m, H$_3$ & H$_5$), 2.14–3.70 (6H, m, H$_2$, H$_6$ & NCH$_2$), 3.9 (1H, m, H$_4$), 5.02 (3H, bs, 2×NH & OH, D$_2$O exchangeable).

Preparation 27

3-Fluoro-4-hydroxypiperidine

Chlorotrimethylsilane (34 ml, 247 mmole) and dry Et$_3$N (34 ml, 247 mmole) were added dropwise respectively to the stirred solution of 1-t-butoxycarbonylpiperidin-4-one (20 g, 100.5 mmole) in dry N,N-dimethyl formamide (40 ml) under nitrogen. The reaction mixture was stirred at 80° C. for 26 hr under nitrogen. The reaction mixture was diluted with hexane (120 ml) and washed with cold saturated aqueous NaHCO$_3$ (3×50 ml) solution. The organic layer was dried (Na$_2$SO$_4$) and concentrated to give 1-t-butoxycarbonylpiperidine-4-silylenol ether as an oil. Yield 24.57 g(90%).

[1-(Chloromethyl)-4-fluoro-1,4-diazoniabicyclo[2.2.2] octanebis (tetrafluoroborate)] (Selectfluor™ reagent, 14.36 g, 40.59 mmole) was added dropwise to the stirred solution of 1-t-butoxycarbonylpiperdine-4-silylenol ether (10 g, 36.9 mmole) in dry acetonitrile (300 ml) under nitrogen over a period of 1 hr. The reaction mixture was diluted with ethyl acetate (800 ml), washed with 50% aqueous NaCl solution (300 ml), saturated NaCl solution (200 ml), dried (Na$_2$SO$_4$) and concentrated. The obtained crude compound was purified by on silica gel column chromatography, elute from a mixture of hexane and ethyl acetate (5:1) furnished 1-t-butoxycarbony-3-fluoropiperidin-4-one.

Sodium borohydride (0.4 g, 10.78 mmole) was added to the stirred solution of 1-t-butoxycarbony-3-fluoropiperidin-4-one (3.8 g, 17.69 mmole) in methanol (125 ml) at 0° C. over a period of 15 min, and stirring was continued for 2 hr at 25° C. The reaction mixture was concentrated to dryness, triturated with water (20 ml) and extracted with ethyl acetate. Ethyl acetate extract was washed with brine solution, water, dried (Na$_2$SO$_4$) and concentrated to dryness. The obtained crude product was purified on silica gel column chromatography, elute from a mixture of hexane and ethyl acetate (4:1) furnished a mixture of two distereomeric 1-t-butoxycarbony-3-fluoro-4-hydroxypiperidine (2.5:1) as oil. Yield 3.2 g.

Trifluoroacetic acid (10 ml) was added dropwise to the stirred solution of the above obtained mixture of two distereomeric 1-t-butoxycarbony-3-fluoro-4-hydroxypiperidine (2.4 g, 10.95 mmole) in dichloromethane (7 ml) at 0° C. over a period of 15 min. The reaction mixture was stirred at ambient temperature for 1 hr, concentrated to dryness in vacuum, methanol (2 ml) was added and again dried in vacuum. The residue was dissolved in aqueous 10% NaOH solution (10 ml) and extracted with ethyl acetate (3×50 ml).

Ethyl acetate extract was washed with water dried (Na$_2$SO$_4$) and concentrated to give quantitatively 3-fluoro-4-hydroxypiperidine. C$_5$H$_{10}$FNO, m/z 120 (M+1).

Preparation 28

4-Hydroxy-3-methyl-4-trifluoromethylpiperidine

Dry tetrahydrofuran (20 ml) was added to a stirred mixture of 1-benzyl-3-methylpiperidin-4-one (4 g, 19.7 mmole) and (Trifluoromethyl) trimethylsilane (3.35 g, 23.64 mmole) at 0° C. and stirred for 5 min. Tetrabutyl ammonium fluoride (0.05 g) was added to it at 0° C. and stirred for another 30 min at 0° C. The reaction mixture was allowed to warm to room temperature, stirred for 3 hr, acidified with 2N HCl to pH 2 and extracted with ether (3×50 ml). Ether extract was dried (Na$_2$SO$_4$) and concentrated in vacuum to give 1-benzyl-3-methyl-4-hydroxy-4-trifluoromethylpiperidine. Yield 5.1 g (95%), C$_{14}$H$_{18}$F$_3$NO, m/z 274 (M+1).

A mixture of 1-benzyl-4-hydroxy-3-methyl-4-trifluoromethylpiperidine (5.1 g, 18.68 mmole) and 20% palladium hydroxide (1 g) in methanol (100 ml) was stirred in hydrogen atmosphere (1 atm.) for 12 hr at 35° C. Catalyst was filtered off, washed with methanol, filtrate was concentrated to dryness to give 4-hydroxy-3-methyl-4-trifluoromethyl-piperidine as oil. Yield 3.4 g (99%), C$_7$H$_{12}$F$_3$NO, m/z 184 (M+1)

Preparation 29

4-Hydroxy-3,3,5-trimethypiperidine

Sodium borohydride (0.2 g, 5.26 mmole) was added to the stirred solution of 1-benzyl-3,3,5-trimethylpiperidin-4-one (2.0 g, 8.73 mmole) in methanol (25 ml) at 0–5° C. over a period of 5 min, and stirring was continued for 1 hr at ambient temperature. The reaction mixture was concentrated to dryness, triturated with water (20 ml) and extracted with ethyl acetate. The ethyl acetate extract was dried (Na$_2$SO$_4$) and concentrated to dryness to furnish 1-benzyl-4-hydroxy-3,3,5-trimethylpiperidine as oil. Yield 1.9 g (91%), C$_{15}$H$_{23}$NO, m/z 234 (M+l).

A mixture of 1-benzyl-4-hydroxy-3,3,5-trimethylpiperidine (1.9 g, 8.15 mmole) and 20% palladium hydroxide (0.2 g) in methanol (20 ml) was stirred in hydrogen atmosphere (1 atm.) for 48 hr at 35° C. Catalyst was filtered off, washed with methanol, filtrate was concentrated to dryness to give 4-hydroxy-3,3,5-trimethylpiperidine as oil. Yield 1.0 g (87%), C$_9$H$_{17}$NO, m/z 144 (M+1).

Preparation 30

3,5-Dimethyl-3-ethyl-4-hydroxypiperidine

1-Benzyl-3-ethyl-piperidin-4-one (33 g, 152.0 mmole) was added to the stirred suspension of sodium hydride (9.5 g, 200.0 mmole) in tetrahydrofuran (300 ml) at 32° C. and stirring was continued for 1 hr. Methyl iodide (30 ml, 490.0 mmole) in dry tetrahydrofuran (100 ml) was added it at 0–5° C. The resulting mixture stirred at room temperature for 4 hr, water (100 ml) and ethyl acetate (800 ml) were added respectively. Organic layer was separated, dried (Na$_2$SO$_4$) and concentrated to give crude product, which was purified through column chromatography. Elute from 10% ethyl acetate in hexane afforded 1-benzyl-3,5-dimethyl-3-ethylpiperidin-4-one. Yield 22.0 g (59%), C$_{16}$H$_{23}$NO, m/z 246 (M+1).

Sodium borohydride (0.8 g, 21.0 mmole) was added to the stirred solution of 1-benzyl-3,5-dimethyl-3-ethylpiperidin-4-one (3.0 g, 12.25 mmole) in methanol (10 ml) at 0–5° C. over a period of 5 min, and stirring was continued for 1 hr at ambient temperature. The reaction mixture was concentrated to dryness, triturated with water (20 ml) and extracted with ethyl acetate. The ethyl acetate extract was dried (Na$_2$SO$_4$) and concentrated to dryness to furnish 1-benzyl-3,5-dimethyl-3-ethyl-4-hydroxypiperidine as oil. Yield 2.9 g (96%), C$_{16}$H$_{25}$NO, m/z 248 (M+l).

A mixture of 1-benzyl-3,5-dimethyl-3-ethyl-4-hydroxypiperidine (2.9 g, 11.74 mmole) and 20% palladium hydroxide (0.5 g) in methanol (20 ml) was stirred in hydrogen atmosphere (1 atm.) for 8 hr at 35° C. Catalyst was filtered off, washed with methanol, filtrate was concentrated to dryness to give 3,5-dimethyl-3-ethyl-4-hydroxypiperidine as oil. Yield 1.7 g (93%), C$_9$H$_{19}$NO, m/z 158 (M+1).

Preparation 31

3,5-Diethyl-4-hydroxy-3-methylpiperidine

Sodium borohydride (0.18 g, 4.8 mmole) was added to the stirred solution of 1-benzyl-3,5-diethyl-3-methylpiperidin-4-one (2.0 g, 7.72 mmole) in methanol (20 ml) at 0–5° C. over a period of 5 min, and stirring was continued for 1 hr at ambient temperature. The reaction mixture was concentrated to dryness, triturated with water (20 ml) and extracted with ethyl acetate. The ethyl acetate extract was dried (Na$_2$SO$_4$) and concentrated to dryness to furnish 1-benzyl-3,5-diethyl-4-hydroxy-3-methylpiperidine as oil. Yield 1.8 g (89%), C$_{17}$H$_{27}$NO, m/z 262 (M+l).

A mixture of 1-benzyl-3,5-diethyl-4-hydroxy-3-methylpiperidine (1.8 g, 6.89 mmole) and 20% palladium hydroxide (0.2 g) in methanol (20 ml) was stirred in hydrogen atmosphere (4 atm.) for 3 hr at 45° C. Catalyst was filtered off, washed with methanol, filtrate was concentrated to give 3,5-diethyl-4-hydroxy-3-methylpiperidine as oil. Yield 1.1 g (94%), C$_{12}$H$_2$NO, m/z 172 (M+1).

EXAMPLE 1

S-(−)-9-fluoro-6,7-dihydro-8-(4-hydroxy-4-trifluoromethylpiperidin-1-yl)-5-methyl-1-oxo-1H, 5H-benzo[i,j]quinolizine-2-carboxylic Acid A mixture of (O-B)-diacetoxy-{S-(−)-8,9-difluoro-5-methyl-6,7-dihydro-5-methyl-1-oxo-1H, 5H-benzo[i,j]quinolizine-2-carboxy}borane (0.0558 g, 0.2 mmole), 4-hydroxy-4-trifluoromethylpiperidine (0.0303 g, 0.3 mmole) and triethylamine (0.0303 g, 0.3 mmole) in DMSO (2 ml) was stirred at 120° C. for 20 hr, concentrated to dryness in vacuum. The obtained residue was stirred with water and filtered. The precipitate was dissolved 1N NaOH and reprecipitated with Conc. HCl. The obtained crude product was purified by preparative HPLC. Yield 0.07 g (80%), m.p. 220–24° C., C$_{20}$H$_{20}$F$_4$N$_2$O$_4$, m/z 429 (M+1), PMR (CDCl$_3$): 1.5 (3H, d, CH$_3$, J=6 Hz), 1.57–2.28 (6H, m, H$_{5'}$, H$_3$, & H$_6$), 2.64–3.6 (6H, m, H$_{2'}$, H$_{6'}$ & H$_7$), 4.56 (1H, m, H$_5$), 8.02 (1H, d, H$_{10}$, J=16.5 Hz), 8.70 (1H, s, H$_3$), 15.1 (1H, bs, COOH, D$_2$O exchangeable).

EXAMPLE 2

S-(−)-9-fluoro-6,7-dihydro-8-(4-hydroxy-3-methylpiperidin-1-yl)-5-methyl-1-oxo-1H,5H-benzo[i,j]quinolizine-2-carboxylic Acid A mixture of (O-B)-diacetoxy-{S-(−)-8,9-difluoro-5-methyl-6,7-dihydro-5-methyl-1-oxo-1H, 5H-benzo[i,j]quinolizine-2-carboxy}borane (0.325 g, 0.8 mmole), 4-hydroxy-3-methyl piperidine (0.45 g, 3.91 mmole) and acetonitrile (15 ml) was heated at 90° C. for 22 hr, concentrated to dryness in vacuum. The obtained residue was stirred with aqueous NaOH (3.5%, 15 ml) solution for 1.5 hr, acidified with Conc. HCl, and extracted with ethyl acetate (25 ml×2). Organic layer was dried over sodium sulphate and concentrated to give crude product, which was purified by preparative HPLC. Yield 0.24 g (80%), m.p. 164–66° C., C20H23FN2O4, m/z 375 (M+1), [α]D25–261.4 0 (c=1%, methanol solution).

EXAMPLE 3

S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylic Acid It was prepared in a similar manner as described in example 2, where trans-4-(RS)-hydroxy-3-(RS)-methylpiperidine was used in place of 4-hydroxy-3-methylpiperidine. Yield 0.8 g (89.6%), m.p. 184–86° C., $[\alpha]_D^{25}$–274°(c=1%, methanol solution), $C_{20}H_{23}FN_2O_4$, m/z 375 (M+1), PMR (CDCl$_3$): 1.06 (3H, d, CH$_3$, J=6 Hz), 1.54 (3H, d, CH$_3$, J=7 Hz), 1.57–2.28 (5H, m, H$_5'$, H$_3'$ & H$_6$), 2.64–3.6 (7H, m, H$_2'$, H$_6'$, H$_4'$ & H$_7$), 4.56 (1H, m, H$_5$), 8.02 (1H, d, H$_{10}$, J=16.5 Hz), 8.70 (1H, s, H$_3$), 15.06 (1H, bs, COOH, D$_2$O exchangeable).

EXAMPLE 4

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic Acid

Method A

Condensation was carried similarly as described in Example 2, where trans-(+)-4-S-acetoxy-3-S-methylpiperidine was used in place of 4-hydroxy-3-methylpiperidine. The obtained residue was stirred with aqueous NaOH (3.5%, 25 ml) solution for 2 hr at 50° C., acidified with conc. HCl, and extracted with ethyl acetate. Organic layer was dried (Na$_2$SO$_4$) and concentrated to give crude product, which was purified by column chromatography. Yield 3.8 g (33%), m.p. 214–18° C., $[\alpha]_D^{25}$–288.8° (c=1%, methanol solution), $C_{20}H_{23}FN_2O_4$, m/z 375 (M+1), PMR (CDCl$_3$): 1.06 (3H, d, CH$_3$, J=6 Hz), 1.54 (3H, d, CH$_3$, J=7 Hz), 1.57–2.28 (5H, m, H$_5'$, H$_3'$ & H$_6$), 2.64–3.6 (7H, m, H$_2'$, H$_6'$, H$_4'$ & H$_7$), 4.56 (1H, m, H$_5$), 8.02 (1H, d, H$_{10}$, J=16.5 Hz), 8.70 (1H, s, H$_3$), 15.06 (1H, bs, COOH, D$_2$O exchangeable).

Method B

It was prepared in a similar manner as described example 2, where trans-(+)-4-S-hydroxy-3-S-methylpiperidine was used in place of 4-hydroxy-3-methylpiperidine. Yield 1.05 g (45%), m.p. 214–18° C., $[\alpha]_D^{25}$–288.8°(c=1%, methanol solution), $C_{20}H_{23}FN_2O_4$, m/z 375 (M+1).

EXAMPLE 5

S-(−)-9-fluoro-6,7-dihydro-8-{trans-(−)-4-R-hydroxy-3-R-methylpiperidin-1-yl}-5-methyl-1-oxo-1H,5H-benzo[i,j]quinolizine-2-carboxylic Acid

Method A

Condensation was carried similarly as described in example 2, where trans-(−)-4-R-acetoxy-3-R-methylpiperidine was used in place of 4-hydroxy-3-methylpiperidine. The obtained residue was stirred with aqueous NaOH (3.5%, 25 ml) solution for 2 hr at 50° C., acidified with conc. HCl, and extracted with ethyl acetate. Organic layer was dried (Na$_2$SO$_4$) and concentrated to give crude product, which was purified by column chromatography. Yield 5.8 g (36%), m.p. 216–18° C., $[\alpha]_D^{25}$–281° (c=1%, methanol solution), $C_{20}H_{23}FN_2O_4$, m/z 375 (M+1), PMR(CDCl$_3$): 1.06 (3H, d, CH$_3$, J=6 Hz), 1.54 (3H, d, CH$_3$, J=7 Hz), 1.57–2.28 (5H, m, H$_5'$, H$_3'$ & H$_6$), 2.64–3.6 (7H, m, H$_2'$, H$_6'$, H$_4'$ & $_{H7}$), 4.56 (1H, m, H$_5$), 8.02 (1H, d, H$_{10}$, J=16.5 Hz), 8.70 (1H, s, H$_3$), 15.06 (1H, bs, COOH, D$_2$O exchangeable).

Method B

It was prepared in a similar manner as described in example 2, where trans-(−)-4-R-hydroxy-3-R-methylpiperidine was used in place of 4-hydroxy-3-methylpiperidine. Yield 1.01 g (50%), m.p. 216–18° C., $[\alpha]_D^{25}$–281°(c=1%, methanol solution), $C_{20}H_{23}FN_2O_4$, m/z 375 (M+1).

EXAMPLE 6

S-(−)-9-fluoro-6,7-dihydro-8-{cis-4-(RS)-hydroxy-3-(RS)-methylpiperidin-1-yl]-5-methyl-1-oxo-1H,5H-benzo[i,j]quinolizine-2-carboxylic Acid It was prepared in a similar manner as described above in Example 4, method A, where cis-4-(RS)-acetoxy-3-(RS)-methylpiperidine was used in place of trans-(+)-4-S-acetoxy-3-S-methylpiperidine. Yield 0.6 g (93%), m.p. 140–42° C., $[\alpha]_D^{25}$–227° (c=1%, methanol solution), $C_{20}H_{23}FN_2O_4$, m/z 375 (M+1), PMR (CDCl$_3$): 1.06 (3H, d, CH$_3$, J=6 Hz), 1.6 (3H, d, CH$_3$, J=7 Hz), 1.82–2.12 (5H, m, H$_3'$, H$_5'$ & H$_6$), 2.78–3.64 (6H, m, H$_2'$, H$_6'$, & H$_7$), 4.02 (1H, m, H$_4'$), 4.54 (1H, m, H$_5$), 8.02 (1H, d, H$_{10}$, J=16.5 Hz), 8.74 (1H, s, H$_3$), 15.14 (1H, bs, COOH, D$_2$O exchangeable).

The obtained mixture of cis isomers was separated by preparative HPLC on YMC-ODS-AM column (250×4.6 mm). Elute from TFA (0.05%) in water-acetonitrile (gradient 0–100% in 20 min, flow rate 1.25 ml/min) gave S-(−)-9-fluoro-6,7-dihydro-8-{cis-(+)-4-S-hydroxy-3-R-methylpiperidin-1-yl}-5-methyl-1-oxo-1H,5H-benzo[i,j]quinolizine-2-carboxylic acid {retention time 12.08 min, m.p. 148–52° C., $[\alpha]_D^{25}$–230 (c=1%, methanol solution)} and S-(−)-9-fluoro-6,7-dihydro-8-{cis-(−)-4-R-hydroxy-3-S-methylpiperidin-1-yl}-5-methyl-1-oxo-1H,5H-benzo[i,j]quinolizine-2-carboxylic acid {retention time 12.19 min, m.p. 158–60° C., $[\alpha]_D^{25}$–216° (c=1%, methanol solution)}.

EXAMPLE 7

S-(−)-9-fluoro-6,7-dihydro-8-{cis-(+)-4-S-hydroxy-3-R-methylpiperidin-1-yl}-5-methyl-1-oxo-1H,5H-benzo[i,j]quinolizine-2-carboxylic Acid It was prepared in a similar manner as described above in Example 4, method A, where cis-(+)-4-S-acetoxy-3-R-methylpiperidine was used in place of trans-(+)-4-S-acetoxy-3-S-methylpiperidine. Yield 0.6 g (93%), m.p. 148–52° C., $[\alpha]_D^{25}$–230° (c=1%, methanol solution), $C_{20}H_{23}FN_2O_4$, m/z 375 (M+1), PMR (CDCl$_3$): 1.06 (3H, d, CH$_3$, J=6 Hz), 1.6 (3H, d, CH$_3$, J=7 Hz), 1.82–2.12 (5H, m, H$_3'$, H$_5'$ & H$_6$), 2.78–3.64 (6H, m, H$_2'$, H$_6'$, & H$_7$), 4.02 (1H, m, H$_4'$), 4.54 (1H, m, H$_5$), 8.02 (1H, d, H$_{10}$, J=16.5 Hz), 8.74 (1H, s, H$_3$), 15.14 (1H, bs, COOH, D$_2$O exchangeable).

EXAMPLE 8

S-(−)-9-fluoro-6,7-dihydro-8-{cis-(−)-4-R-hydroxy-3-S-methylpiperidin-1-yl}-5-methyl-1-oxo-1H,5H-benzo[i,j]quinolizine-2-carboxylic Acid It was prepared in a similar manner as described above in Example 4, method A, where cis-(−)-4-R-acetoxy-3-S-methylpiperidine was used in place of trans-(+)-4-S-acetoxy-3-S-methylpiperidine. Yield 0.6 g (93%), m.p. 158–62° C, $[\alpha]_D^{25}$ −216° (c=1%, methanol solution), $C_{20}H_{23}FN_2O_4$, m/z 375 (M+1), PMR (CDCl$_3$): 1.06 (3H, d, CH$_3$, J=6 Hz), 1.6 (3H, d, CH$_3$, J=7 Hz), 1.82–2.12 (5H, m, H$_{3'}$, H$_{5'}$ & H$_6$), 2.78–3.64 (6H, m, H$_{2'}$, H$_{6'}$, & H$_7$), 4.02 (1H, m, H$_{4'}$), 4.54 (1H, m, H$_5$), 8.02 (1H, d, H$_{10}$, J=16.5 Hz), 8.74 (1H, s, H$_3$), 15.14 (1H, bs, COOH, D$_2$O exchangeable).

EXAMPLE 9

S-(−)-9-fluoro-6,7-dihydro-8-(4-methoxy-3-methylpiperidin-1-yl)-5-methyl-1-oxo-1H,5H-benzo[i,j]quinolizine-2-carboxylic Acid It was prepared in a similar manner as described above in Example 2, where 4-methoxy-3-methyl piperidine was used in place of 4-hydroxy-3-methylpiperidine. Yield 0.16 g (55%), m.p. 160–62° C., $[\alpha]_D^{25}$ −254.4° (c=1%, methanol solution), $C_{21}H_{25}FN_2O_4$, m/z 389 (M+1).

EXAMPLE 10

S-(−)-9-fluoro-6,7-dihydro-8-(4-ethoxy-3-methylpiperidin-1-yl)-5-methyl-1-oxo-1H,5H-benzo[i,j]quinolizine-2-carboxylic Acid It was prepared in a similar manner as described above in Example 2, where 4-ethoxy-3-methyl piperidine was used in place of 4-hydroxy-3-methylpiperidine. Yield 0.15 g (57%), m.p. 180–84° C., $[\alpha]_D^{25}$ −238.6° (c=1%, methanol solution), $C_{22}H_{27}FN_2O_4$, m/z 403 (M+1)

EXAMPLE 11

S-(−)-9-fluoro-6,7-dihydro-8-(4-hydroxy-3-trifluoromethylpiperidin-1-yl)-5-methyl-1-oxo-1H, 5H-benzo[i,j]quinolizine-2-carboxylic Acid It was prepared in a similar manner as described above in Example 2, where 4-hydroxy-3-trifluoromethylpiperidine was used in place of 4-hydroxy-3-methyl piperidine. Yield 0.15 g (58%), m.p. 130–35° C., $C_{20}H_{20}F_4N_2O_4$, m/z 429 (M+1).

EXAMPLE 12

S-(−)-9-fluoro-6,7-dihydro-8-(3-ethyl-4-hydroxypiperidin-1-yl)-5-methyl-1-oxo-1H,5H-benzo[i,j]quinolizine-2-carboxylic Acid It was prepared in a similar manner as described above, where 3-ethyl-4-hydroxypiperidine was used in place of 4-hydroxy-3-methylpiperidine. Yield 0.25 g (80%), m.p.146–48° C., $[\alpha]_D^{25}$ −268° (c=1%, methanol solution), $C_{21}H_{25}FN_2O_4$, m/z 389 (M+1), PMR (CDCl$_3$): 1.02 (3H, t, CH$_3$, J=6 Hz), 1.61 (3H, d, CH$_3$, J=7 Hz), 1.74–2.24 (7H, m, H$_{3'}$, H$_{5'}$, H$_6$ & CH$_2$), 2.68–3.62 (6H, m, H$_{2'}$, H$_{6'}$ & H$_7$), 4.1 (1H, m, H$_{4'}$), 4.54 (1H, m, H$_5$), 8.06 (1H, d, H$_{10}$, J=16.5 Hz), 8.75 (1H, s, H$_3$), 15.1 (1H, bs, COOH, D$_2$O exchangeable).

EXAMPLE 13

S-(−)-9-fluoro-6,7-dihydro-8-(4-hydroxy-3-n-propylpiperidin-1-yl)-5-methyl-1-oxo-1H,5H-benzo[i,j]quinolizine-2-carboxylic Acid It was prepared in a similar manner as described in Example 2, where 4-hydroxy-3-n-propylpiperidine was used in place of 4-hydroxy-3-methylpiperidine. Yield 0.2 g (41%), m.p. 170–72° C., $C_{22}H_{27}FN_2O_4$, m/z 403 (M+1), PMR (CDCl$_3$): 0.9 (3H, t, CH$_3$, J=6 Hz), 1.2–1.5 (4H, m, 2×CH$_2$), 1.56 (3H, d, CH$_3$, J=7 Hz), 1.64–2.28 (6H, m, H$_{3'}$, H$_{5'}$, H$_6$ & OH, D$_2$O exchangeable), 2.68–3.58 (5H, m, H$_{2'}$, H$_{6'}$ & H$_7$), 4.08 (1H, m, H$_{4'}$), 4.52 (1H, m, H$_5$), 8.02 (1H, d, H$_{10}$, J=16.5 Hz), 8.72 (1H, s, H$_3$), 15.1 (1H, bs, COOH, D$_2$O exchangeable).

EXAMPLE 14

S-(−)-9-fluoro-6,7-dihydro-8-(4-hydroxy-3-isopropylpiperidin-1-yl)-5-methyl-1-oxo-1H,5H-benzo[i,j]quinolizine-2-carboxylic Acid It was prepared in a similar manner as described in Example 2, where 4-hydroxy-3-isopropyl piperidine was used in place of 4-hydroxy-3-methylpiperidine. Yield 0.2 g (40%), m.p. 188–90° C., $C_{22}H_{27}FN_2O_4$, m/z 403 (M+1), PMR (CDCl$_3$): 0.9 (3H, t, CH$_3$, J=6 Hz), 1.02 (3H, t, CH$_3$, J=6 Hz), 1.58 (3H, d, CH$_3$, J=7 Hz), 1.62–2.44 (6H, m, H$_{3'}$, H$_{5'}$, H$_6$ & OH, D$_2$O exchangeable), 2.68–3.84 (6H, m, H$_{2'}$, H$_{6'}$, H$_7$ & CH), 4.08 (1H, m, H$_{4'}$), 4.52 (1H, m, H$_5$), 8.04 (1H, d, H$_{10}$, J=16.5 Hz), 8.7 (1H, s, H$_3$), 15.1 (1H, bs, COOH, D$_2$O exchangeable).

EXAMPLE 15

S-(−)-9-fluoro-6,7-dihydro-8-(3-n-butyl-4-hydroxypiperidin-1-yl)-5-methyl-1-oxo-1H,5H-benzo[i,j]quinolizine-2-carboxylic Acid It was prepared in a similar manner as described in Example 2, wehre 3-n-butyl-4-hydroxy-piperidine was used in place of 4-hydroxy-3-methylpiperidine. Yield 0.1 g (50%), m.p. 176–78° C., $C_{23}H_{29}FN_2O_4$, m/z 417 (M+1), PMR (CDCl$_3$): 0.9 (3H, t, CH$_3$, J=6 Hz), 1.18–1.48 (6H, m, 3×CH$_2$), 1.6 (3H, d, CH$_3$, J=7 Hz), 1.64–2.2 (6H, m, H$_{3'}$, H$_{5'}$, H$_6$ & OH, D$_2$O exchangeable), 2.68–3.58 (5H, m, H$_{2'}$, H$_{6'}$ & H$_7$), 4.1 (1H, m, H$_{4'}$), 4.56 (1H, m, H$_5$), 8.04 (1H, d, H$_{10}$, J=16.5 Hz), 8.78 (1H, s, H$_3$), 15.04 (1H, bs, COOH, D$_2$O exchangeable).

EXAMPLE 16

S-(−)-9-fluoro-6,7-dihydro-8-(4-hydroxy-3-isobutylpiperidin-1-yl)-5-methyl-1-oxo-1H,5H-benzo[i,j]quinolizine-2-carboxylic Acid It was prepared in a similar manner as described in Example 2, where 4-hydroxy-3-isobutyl piperidine was used in place of 4-hydroxy-3-methylpiperidine. Yield 0.75 g (45%), m.p. 206–8° C., $C_{23}H_{29}FN_2O_4$, m/z 417 (M+1), PMR (CDCl$_3$): 0.94 (6H, m, 2×CH$_3$), 1.18 (2H, m, CH$_2$), 1.6 (3H, d, CH$_3$, J=7 Hz), 1.68–2.2 (6H, m, H$_{3'}$, H$_{5'}$, H$_6$ & OH, D$_2$O exchangeable), 2.8–3.6 (6H, m, H$_{2'}$, H$_{6'}$ & H$_7$), 3.68 (1H, m, CH), 4.28 (1H, m, H$_{4'}$), 4.54 (1H, m, H$_5$), 8.04 (1H, d, H$_{10}$, J=16.5 Hz), 8.7 (1H, s, H$_3$), 15.08 (1H, bs, COOH, D$_2$O exchangeable).

EXAMPLE 17

S-(−)-9-fluoro-6,7-dihydro-8-(3-benzyl-4-hydroxypiperidin-1-yl)-5-methyl-1-oxo-1H,5H-benzo[i,j]quinolizine-2-carboxylic Acid It was prepared in a similar manner as described in example 2, where 3-benzyl-4-hydroxy-piperidine was used in place of 4-hydroxy-3-methylpiperidine. Yield 0.5 g (50%), m.p.204° C., $C_{26}H_{27}FN_2O_4$, m/z 451 (M+1).

EXAMPLE 18

S-(−)-9-fluoro-6,7-dihydro-8-(3-fluoro-4-hydroxypiperidin-1-yl)-5-methyl-1-oxo-1H,5H-benzo[i,j]quinolizine-2-carboxylic Acid It was prepared in a similar manner as described in Example 2, where 3-fluoro-4-hydroxy-piperidine was used in place of 4-hydroxy-3-methylpiperidine. Yield 0.1 g (25%), m.p. 180° C. (decompose), $C_{19}H_{20}F_2N_2O_4$, m/z 379 (M+1).

EXAMPLE 19

S-(−)-9-fluoro-6,7-dihydro-8-(3,3-dimethyl-4-hydroxypiperidin-1-yl)-5-methyl-1-oxo-1H,5H-benzo[i,j]quinolizine-2-carboxylic Acid It was prepared in a similar manner as described in Example 2, where 3,3-dimethyl-4-hydroxy piperidine was used in place of 4-hydroxy-3-methylpiperidine. Yield 0.25 g (80%), m.p. 220–24° C., $[\alpha]_D^{25}$ −143.5° (c=1, methanol), $C_{21}H_{25}FN_2O_4$, m/z 389 (M+1), PMR(CDCl$_3$): 1.05 (6H, 2s, 2×CH$_3$), 1.5 (3H, d, CH$_3$, J=7 Hz), 1.62–2.38 (4H, m, H$_5$, & H$_6$), 2.54–3.64 (6H, m, H$_{2'}$, H$_{6'}$ & H$_7$), 4.28 (1H, m, H$_{4'}$), 4.54 (1H, m, H$_5$), 8.04 (1H, d, H$_{10}$, J=16.5 Hz), 8.76 (1H, s, H$_3$), 15.0 (1H, bs, COOH, D$_2$O exchangeable).

EXAMPLE 20

S-(−)-9-fluoro-6,7-dihydro-8-(3,5-dimethyl-4-hydroxypiperidin-1-yl)-5-methyl-1-oxo-1H,5H-benzo[i,j]quinolizine-2-carboxylic Acid It was prepared in a similar manner as described in Example 2, where 3,5-dimethyl-4-hydroxy-piperidine was used in place of 4-hydroxy-3-methylpiperidine. Yield 0.5 g (40%), m.p. 208–10° C., $C_{21}H_{25}FN_2O_4$, m/z 389 (M+1), PMR (CDCl$_3$): 1.05 (6H, m, 2×CH$_3$), 1.5 (3H, d, CH$_3$, J=7 Hz), 1.62–2.38 (4H, m, H$_{3'}$, H$_5$, & H$_6$), 2.54–3.74 (6H, m, H$_{2'}$, H$_{6'}$ & H$_7$), 4.5 (2H, m, H$_{4'}$ & H$_5$), 8.04 (1H, d, H$_{10}$, J=16.5 Hz), 8.76 (1H, s, H$_3$), 15.04 (1H, bs, COOH, D$_2$O exchangeable).

EXAMPLE 21

S-(−)-9-fluoro-6,7-dihydro-8-{trans-3,5-dimethyl-4-hydroxypiperidin-1-yl)-5-methyl-1-oxo-1H,5H-benzo[i,j]quinolizine-2-carboxylic Acid It was prepared in a similar manner as described in Example 2, where trans-3,5-dimethyl-4-hydroxypiperidine was used in place of 4-hydroxy-3-methylpiperidine. Yield 1.0 g (35%), m.p. 140–50° C., $C_{21}H_{25}FN_2O_4$, m/z 389 (M+1), PMR (CDCl$_3$): 1.05 (6H, d, 2×CH$_3$, j=6.8 Hz), 1.5 (3H, d, CH$_3$, J=7 Hz), 1.83 (2H, m, H$_{3'}$, & H$_5$'), 2.21 (2H, m, H$_6$), 2.62–2.81 (6H, m, H$_{2'}$, H$_{6'}$ & H$_7$), 4.5 (2H, m, H$_{4'}$ & H$_5$), 8.04 (1H, d, H$_{10}$, J=16.5 Hz), 8.76 (1H, s, H$_3$), 15.04 (1H, bs, COOH, D$_2$O exchangeable).

The obtained mixture of trans isomers was separated by preparative HPLC on YMC-ODS-AM column (250×4.6 mm). Elute from TFA (0.05%) in water-acetonitrile (gradient 0–100% in 20 min, flow rate 1.25 ml/min) gave early isomer {retention time 10.4 min, m.p. 110° C., $[\alpha]_D^{25}$ −104° (c=1%, chloroform solution)} and late isomer {retention time 12.7 min, m.p. 210–12° C., $[\alpha]_D^{25}$ −191.5° (c=1%, chloroform solution)}.

EXAMPLE 22

S-(−)-9-fluoro-6,7-dihydro-8-{cis-3,5-dimethyl-4-hydroxypiperidin-1-yl)-5-methyl-1-oxo-1H,5H-benzo[i,j]quinolizine-2-carboxylic Acid It was prepared in a similar manner as described in Example 2, where cis-3,5-dimethyl-4-hydroxypiperidine was used in place of 4-hydroxy-3-methylpiperidine. Yield 0.48 g (50%), m.p. 200–02° C., $C_{21}H_{25}FN_2O_4$, m/z 389 (M+1), PMR (CDCl$_3$): 1.05 (6H, d, 2×CH$_3$, j=7.2 Hz), 1.5 (3H, d, CH$_3$, J=7 Hz), 1.81–2.35 (4H, m, H$_{3'}$, H$_5$, & H$_6$), 2.61–3.51 (6H, m, H$_{2'}$, H$_{6'}$ & H$_7$), 4.5 (2H, m, H$_{4'}$ & H$_5$), 8.04 (1H, d, H$_{10}$, J=16.5 Hz), 8.7 (1H, s, H$_3$), 15.1 (1H, bs, COOH, D$_2$O exchangeable).

EXAMPLE 23

S-(−)-9-fluoro-6,7-dihydro-8-(3,3-diethyl-4-hydroxypiperidin-1-yl)-5-methyl-1-oxo-1H,5H-benzo[i,j]quinolizine-2-carboxylic Acid It was prepared in a similar manner as described in Example 2, where 3,3-diethyl-4-hydroxy-piperidine was used in place of 4-hydroxy-3-methylpiperidine. Yield 0.63 g (31%), m.p.126–28° C., $[\alpha]_D^{25}$ −221° (c=1%, methanol solution), $C_{23}H_{29}FN_2O_4$, m/z 417 (M+1)

EXAMPLE 24

S-(−)-9-fluoro-6,7-dihydro-8-(3-ethyl-4-hydroxy-3-methylpiperidin-1-yl)-5-methyl-1-oxo-1H,5H-benzo[i,j]quinolizine-2-carboxylic Acid It was prepared in a similar manner as described in Example 2, where 3-ethyl-4-hydroxy-3-methyl piperidine was used in place of 4-hydroxy-3-methylpiperidine. Yield 0.153 g (81%), m.p. 192–4° C., $C_{22}H_{27}FN_2O_4$, m/z 403 (M+1), PMR(CDCl$_3$): 0.94 (3H, t, CH$_3$, j=6 Hz), 1.1 (3H, s, CH$_3$), 1.3 (2H, m, CH$_2$), 1.58 (3H, d, CH$_3$, J=7 Hz), 1.68–2.3 (5H, m, H$_5$, H$_6$ & OH, D$_2$O exchangeable), 2.58–3.7 (6H, m, H$_{2'}$, H$_{6'}$ & H$_7$), 4.28 (1H, m, H$_{4'}$), 4.54 (1H, m, H$_5$), 8.04 (1H, d, H$_{10}$, J=16.5 Hz), 8.78 (1H, s, H$_3$), 15.2 (1H, bs, COOH, D$_2$O exchangeable).

EXAMPLE 25

S-(−)-9-fluoro-6,7-dihydro-8-(3-aminomethyl-4-hydroxypiperidin-1-yl-5-methyl-1-oxo-1H,5H-benzo[i,j]quinolizine-2-carboxylic Acid A mixture of (O-B)-diacetoxy-{S-(−)-8,9-difluoro-5-methyl-6,7-dihydro-5-methyl-1-oxo-1H,5H-benzo[i,j]quinolizine-2-carboxy}borane (0.77 g, 1.88 mmole), 4-hydroxy-3-(t-butoxycarbonylaminomethylpiperidine (1.1 g, 4.78 mmole) and acetonitrile (20 ml) was heated at 90° C. for 6 hr, and concentrated to dryness in vacuum. The obtained residue was triturated with water, filtered and washed with water to provide S-(−)-9-fluoro-6,7-dihydro-8-(4-hydroxy-3-t-butoxycarbonylaminomethylpiperidin-1-yl)-5-methyl-1-oxo-1H,5H-benzo[i,j]quinolizine-2-carboxylic acid. Yield 0.3 g (34%), m.p. 188–90° C., $[\alpha]_D^{24}$ −209° (c=1%, methanol solution), $C_{25}H_{32}FN_3O_6$, m/z 490 (M+1), PMR (CDCl$_3$): 1.42 (9H, s, 3×CH$_3$), 1.6 (3H, d, CH$_3$, J=7 Hz), 1.75–2.32 (5H, m, H$_{3'}$, H$_5$, & H$_6$), 2.72–3.82 (8H, m, NCH$_2$, H$_{2'}$, H$_{6'}$, H$_7$), 4.05 (1H, m, H$_{4'}$), 4.54 (1H, m, H$_5$), 4.88 (1H, m, NH, D$_2$O exchangeable), 8.02 (1H, d, H$_{10}$, J=16.5 Hz), 8.72 (1H, s, H$_3$), 15.05 (1H, bs, OH, D$_2$O exchangeable).

The obtained S-(−)-9-fluoro-6,7-dihydro-8-(4-hydroxy-3-t-butoxycarbonylaminomethyl piperidin-1-yl)-5-methyl-1-oxo-1H,5H-benzo[i,j]quinolizine-2-carboxylic acid was refluxed with conc. HCl (2 ml) for 5 hr, concentrated in vacuum to dryness, triturated with ether and filtered to give title product as hydrochloride. Yield 0.21 g (60%), m.p. 238–40° C., $[\alpha]_D^{24}$ −143° (c=0.25%, methanol solution), $C_{20}H_{24}FN_3O_4\cdot HCl$, m/z 425 and 426 (M+), PMR(DMSOd$_6$): 1.46 (3H, d, CH$_3$, J=7 Hz), 1.72–2.36 (5H, m, H$_3$', H$_5$' & H$_6$), 2.64–3.8 (8H, m, NCH$_2$, H$_2$', H$_6$', H$_7$), 4.0 (1H, m, H$_4$'), 4.92 (1H, m, H$_5$), 5.36 (1H, m, NH, D$_2$O exchangeable), 7.92 (1H, d, H$_{10}$, J=16.5 Hz), 9.0 (1H, s, H$_3$), 15.24 (1H, bs, OH, D$_2$O exchangeable).

EXAMPLE 26

S-(−)-9-fluoro-6,7-dihydro-8-(4-hydroxy-4-methylpiperidin-1-yl)-5-methyl-1-oxo-1H,5H-benzo[i,j]quinolizine-2-carboxylic Acid It was prepared in a similar manner as described in Example 1, where 4-hydroxy-4-methyl piperidine was used in place of 4-hydroxy-3-trifluoromethylpiperidine. Yield 0.5 g (42%), m.p. 276° C., [α]$_D^{25}$ −283° (c=0.25, methanol solution), C$_{20}$H$_{23}$FN$_2$O$_4$, m/z 375 (M+1), PMR(CDCl$_3$): 1.32 (3H, s, CH$_3$), 1.53 (3H, d, CH$_3$, J=6.8 Hz), 1.58–2.13 (6H, m, H$_5$', H$_3$' & H$_6$), 2.68–3.61 (7H, m, H$_2$', H$_6$', H$_7$ & OH), 4.52 (1H, m, H$_5$), 8.1 (1H, d, H$_{10}$, J=12.2 Hz), 8.64 (1H, s, H$_3$), 15.13 (1H, bs, COOH, D$_2$O exchangeable).

EXAMPLE 27

S-(−)-9-fluoro-6,7-dihydro-8-(4-hydroxy-4-phenylpiperidin-1-yl)-5-methyl-1-oxo-1H,5H-benzo[i,j]quinolizine-2-carboxylic Acid It was prepared in a similar manner as described in Example 1, where 4-hydroxy-4-phenyl piperidine was used in place of 4-hydroxy-4-trifluoromethylpiperidine. Yield 0.05 g (36%), m.p. 223° C., [α]$_D^{26}$ −242° (c=0.1, methanol solution), C$_{20}$H$_{23}$FN$_2$O$_4$, m/z 437 (M+1), PMR (CDCl$_3$): 1.64 (3H, d, CH$_3$, J=6.5 Hz), 1.98–2.43 (6H, m, H$_5$', H$_3$' & H$_6$), 2.8–3.93 (6H, m, H$_2$', H$_6$' & H$_7$), 4.59 (1H, m, H$_5$), 7.32–7.64 (5H, m, Ar—H), 8.03 (1H, d, H$_{10}$, J=12.4 Hz), 8.70 (1H, s, H$_3$), 15.09 (1H, bs, COOH, D$_2$O exchangeable).

EXAMPLE 28

S-(−)-9-fluoro-6,7-dihydro-8-(4-hydroxy-3-methyl-4-trifluoromethylpiperidin-1-yl)-5-methyl-1-oxo-1H,5H-benzo[i,j]quinolizine-2-carboxylic Acid It was prepared in a similar manner as described in example 1 as a mixture of two diastereomers (75:25), where 4-hydroxy-3-methyl-4-trifluoromethylpiperidine was used in place of 4-hydroxy-4-trifluoromethylpiperidine. Yield 0.35 g (50%), m.p. 250° C. (decompose), C$_{21}$H$_{22}$F$_4$N$_2$O$_4$, m/z 443 (M+1).

EXAMPLE 29

S-(−)-9-fluoro-6,7-dihydro-8-(4-hydroxy-3-methylpiperidin-1-yl)-5-methyl-1-oxo-1H,5H-benzo[i,j]quinolizine-2-carboxylic Acid Sodium Salt Dihydrate S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid (1.0 g, 2.6737 mmole) was added to the stirred aqueous NaOH solution (2.631 ml, 1.0162 N) to obtain a clear solution, which was diluted with distilled water (10 ml). The obtained solution was lyophilized to furnish sodium salt dihydrate as white solid. Yield 0.98 g (92.5%), m.p. 296–98° C. (d), [α]D25−239.4 0 (c=1%, methanol solution), moisture content 8.32% (by Karl Fisher method), m/z 397 (M+1), C20H22FN2O4Na.2H2O, found C 55.73, H 6.03, N 6.48 calcd. C 55.55, H 6.01, and N 6.51.

EXAMPLE 30

S-(−)-9-fluoro-6,7-dihydro-8-{trans-(+)-4-S-hydroxy-3-S-methylpiperidin 1-yl}-5-methyl-1-oxo-1H,5H-benzo[i,j]quinolizine-2-carboxylic Acid Arginine Salt Dihydrate Aqueous L-arginine solution (0.441 g, 2.54 mmole, 15 ml) was added to a stirred solution of S-(−)-9-fluoro-6,7-dihydro-8-{trans-(+)-4-S-hydroxy-3-S-methylpiperidin-1-yl}-5-methyl-1-oxo-1H, 5H-benzo[i,j]quinolizine-2-carboxylic acid (0.95 g, 2.54 mmole) in methanol (40 ml). The obtained clear solution (filter through a micron filter to remove if any suspended impurity is there) was concentrated to dryness to give arginine salt dihydrate. Yield 1.37 g (92%), m.p. 190–92° C. (d), [α]$_D^{25}$−158.4° (c=1%, methanol solution), C$_{26}$H$_{37}$FN$_6$O$_6$.2H$_2$O, m/z 584 (M$^+$), found C 53.09, H 7.22, N 13.96; calcd. C 53.42, H 7.02, and N 14.38, PMR (D$_2$O): 1.06 (3H, d, CH$_3$, j=6 Hz), 1.54 (3H, d, CH$_3$, j=7 Hz), 1.57–2.28 (9H, m, H$_3$', H$_5$', H$_6$ & 2×CH$_2$), 2.64–3.6 (9H, m, H$_2$', H$_6$', H$_4$', H$_7$, and NCH$_2$), 4.56 (1H, m, H$_5$), 7.68 (1H, d, H$_{10}$ j=16.1 Hz), 8.42 (1H, s, H$_3$).

EXAMPLE 31

S-(−)-9-fluoro-6,7-dihydro-8-{trans-(−)-4-R-hydroxy-3-R-methylpiperidin-1-yl}-5-methyl-1-oxo-1H,5H-benzo[i,j]quinolizine-2-carboxylic Acid Arginine Salt 3.5 Hydrate Aqueous L-arginine solution (0.441 g, 2.54 mmole, 15 ml) was added to a stirred solution of S-(−)-9-fluoro-6,7-dihydro-8-{trans-(−)-4-R-hydroxy-3-R-methylpiperidin-1-yl}-5-methyl-1-oxo-1H, 5H-benzo[i,j]quinolizine-2-carboxylic acid (0.95 g, 2.54 mmole) in methanol (40 ml). The obtained clear solution (filter through a micron filter to remove if any suspended impurity is there) was concentrated to dryness to give arginine salt dihydrate. Yield 1.39 g (93%), m.p. 188–90° C. (d), [α]$_D^{25}$−167.20 (c=1%, methanol solution), C$_{26}$H$_{37}$FN$_6$O$_6$. 3.5H$_2$O, found C 51.15, H 7.48, N 13.58; calcd. C 51.06, H 7.2, and N 13.75, PMR (D$_2$O): 1.06 (3H, d, CH$_3$, j=6 Hz), 1.54 (3H, d, CH$_3$, j=7 Hz), 1.57–2.28 (9H, m, H$_3$', H$_5$', H$_6$ & 2×CH$_2$), 2.64–3.6 (9H, m, H$_2$', H$_6$', H$_4$', H$_7$, and NCH$_2$), 4.56 (1H, m, H$_5$), 7.68 (1H, d, H$_{10}$, j=16.1 Hz), 8.42 (1H, s, H$_3$).

EXAMPLE 32

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic Acid Histidine Salt Aqueous L-histidine solution (0.078 g, 0.5 mmole, 5 ml) was added to a stirred solution of S-(−)-9-fluoro-6,7-dihydro-8-{trans-(+)-4-S-hydroxy-3-S-methylpiperidin-1-yl}-5-methyl-1-oxo-1H, 5H-benzo[i,j]quinolizine-2-carboxylic acid (0.187 g, 0.5 mmole) in methanol (10 ml) and concentrated to dryness to give histidine salt. Yield 0.265 g (100%), m.p. 216° C., [α]$_D^{25}$−200° C. (c=1%, 20% aqueous methanol solution), C$_{26}$H$_{32}$FN$_5$O$_6$, m/z 530 (M+1).

EXAMPLE 33

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic Acid Lysine Salt It was prepared in a similar manner as described in example 32, where lysine was used in place of histidine.

Yield 0.26 g (100%), m.p. 204° C., $[\alpha]_D^{25}$ −174° (c=1%, methanol solution), $C_{26}H_{37}FN_4O_6$, m/z 521 (M+1).

EXAMPLE 34

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic Acid Arginine Methyl Ester Salt A solution L-arginine methyl ester (0.094 g, 0.5 mmole) in methanol (10 ml) was added to a stirred solution of S-(−)-9-fluoro-6,7-dihydro-8-{trans-(+)-4-S-hydroxy-3-S-methylpiperidin-1-yl}-5-methyl-1-oxo-1H, 5H-benzo[i,j]quinolizine-2-carboxylic acid (0.187 g, 0.5 mmole) in methanol (10 ml). The resulting solution was concentrated to dryness to give arginine methyl ester salt. Yield 0.28 g (99%), m.p. 210° C. (d), $[\alpha]_D^{25}$ −180° C.(c=1%, methanol solution), $C_{27}H_{39}FN_6O_6$, m/z 563 (M+1).

EXAMPLE 35

S-(−)-9-fluoro-6,7-dihydro-S-{trans-(+)-4-S-hydroxy-3-S-methylpiperidin-1-yl}-5-methyl-1-oxo-1H,5H-benzo[i,j]quinolizine-2-carboxylic Acid Histidine Methyl Ester Salt It was prepared in a similar manner as described in Example 34, where histidine methyl ester was used in place of L-arginine methyl ester. Yield 0.27 g (100%) m.p. 210° C., $[\alpha]_D^{25}$ −219° C. (c=1%, 10% aqueous methanol solution), $C_{27}H_{34}FN_5O_6$, m/z 544 (M+1).

EXAMPLE 36

S-(−)-9-fluoro-6,7-dihydro-8-(4-acetoxy-3-methylpiperidin-1-yl)-5-methyl-1-oxo-1H,5H-benzo[i,j]quinolizine-2-carboxylic Acid Acetic anhydride (0.217 ml, 2.13 mmole) was added to a stirred solution of S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid (0.2 g, 0.534 mmole) in pyridine (3 ml) at 0° C. The reaction mixture was heated at 80–85° C. for 2 hr, concentrated in vacuum to dryness, and triturated with water (20 ml). The solid thus separated was filtered, washed with water (10 ml) and dried to give titled product. Yield 0.18 g (81%), m.p. 140–42° C., $[\alpha]_D^{25}$ −234° (c=1%, methanol solution), $C_{22}H_{25}FN_2O_5$, m/z 417 (M+1), PMR (CDCl$_3$): 1.00 (3H, d, CH$_3$, J=7 Hz), 1.62 (3H, d, CH$_3$, J=7 Hz), 2.1 (3H, s, COCH$_3$), 1.8–2.38 (4H, m, H$_{5'}$ & H$_6$), 2.78–3.5 (5H, m, H$_{2'}$, H$_{6'}$, H$_7$), 4.51 (1H, m, H$_5$), 4.62 (1H, m, H$_{3'}$), 5.12 (1H, m, H$_{4'}$), 8.02 (1H, d, H$_{10}$, J=17 Hz), 8.72 (1H, s, H$_3$), 15.02 (1H, bs, COOH, D$_2$O exchangeable).

EXAMPLE 37

S-(−)-9-fluoro-6,7-dihydro-8-(4-acetoxy-3,3-dimethylpiperidin-1-yl)-5-methyl-1-oxo-1H,5H-benzo[i,j]quinolizine-2-carboxylic Acid It was prepared in a similar manner as described in example 36, where S-(−)-9-fluoro-6,7-dihydro-8-(4-hydroxy-3,3-dimethylpiperidin-1-yl)-5-methyl-1-oxo-1H, 5H-benzo[i,j]quinolizine-2-carboxylic acid was used in place of S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid. Yield 0.035 g (31%), m.p. 195° C., $[\alpha]_D^{25}$ −170.75° (c=1%, methanol solution), $C_{23}H_{27}FN_2O_5$, m/z 431 (M+1), PMR (CDCl$_3$): 1.02 (6H, 2s, 2×CH$_3$), 1.54 (3H, d, CH$_3$, J=7 Hz), 2.1 (3H, s, COCH$_3$), 1.8–2.38 (4H, m, H$_{5'}$, H$_6$), 2.72–3.52 (6H, m, H$_{2'}$, H$_{6'}$,H$_7$), 4.6 (1H, m, H$_5$), 4.82 (1H, m, H$_{4'}$), 8.04 (1H, d, H$_{10}$, J=17 Hz), 8.74 (1H, s, H$_3$), 15.02 (1H, bs, COOH, D$_2$O exchangeable).

EXAMPLE 38

S-(−)-9-fluoro-6,7-dihydro-8-(4-acetoxy-3-ethylpiperidin-1-yl)-5-methyl-1-oxo-1H,5H-benzo[i,j]quinolizine-2-carboxylic Acid It was prepared in a similar manner as described Example 36, where S-(−)-9-fluoro-6,7-dihydro-8-(4-hydroxy-3-ethylpiperidin-1-yl)-5-methyl-1-oxo-1H,5H-benzo[i,j]quinolizine-2-carboxylic acid was used in place of S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid. Yield 0.8 g (29%), m.p.148–50° C., $[\alpha]_D^{25}$ −199° C. (c=1%, methanol solution), $C_{23}H_{27}FN_2O_5$, m/z 431 (M$^+$), PMR (CDCl$_3$): 0.98 (3H, t, CH$_3$, J=7 Hz), 1.58 (3H, d, CH$_3$, J=7 Hz), 2.1 (3H, s, COCH$_3$), 1.18–2.38 (6H, m, H$_{5'}$, H$_6$ & CH$_2$), 2.78–3.58 (6H, m, H$_{2'}$, H$_{6'}$, H$_7$), 4.56 (1H, m, H$_5$), 4.76 (1H, m, H$_{3'}$), 5.24 (1H, m, H$_{4'}$), 8.08 (1H, d, H$_{10}$, J=17 Hz), 8.72 (1H, s, H$_3$), 15.06 (1H, bs, COOH, D$_2$O exchangeable).

EXAMPLE 39

S-(−)-9-fluoro-6,7-dihydro-8-(4-acetoxy-3-ethyl-3-methylpiperidin-1-yl)-5-methyl-1-oxo-1H,5H-benzo[i,j]quinolizine-2-carboxylic Acid It was prepared in a similar manner as described in Example 36, where S-(−)-9-fluoro-6,7-dihydro-8-(3-ethyl-4-hydroxy-3-methylpiperidin-1-yl)-5-methyl-1-oxo-1H,5H-benzo[i,j]quinolizine-2-carboxylic acid was used in place of S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid. Yield 0.15 g (90%), m.p. 212–14° C., $[\alpha]_D^{25}$ −158° C. (c=1%, methanol solution), $C_{24}H_{29}FN_2O_5$, m/z 445 (M$^+$), PMR (CDCl$_3$): 0.98 (6H, m, 2×CH$_3$), 1.58 (3H, d, CH$_3$, J=7 Hz), 2.1 (3H, s, COCH$_3$), 1.18–2.38 (6H, m, H$_{5'}$, H$_6$ & CH$_2$), 2.78–3.58 (6H, m, H$_{2'}$, H$_{6'}$, H$_7$), 4.56 (1H, m, H$_5$), 4.85 (1H, m, H$_{4'}$), 8.04 (1H, d, H$_{10}$, J=17 Hz), 8.72 (1H, s, H$_3$), 15.12 (1H, bs, COOH, D$_2$O exchangeable).

EXAMPLE 40

S-(−)-9-fluoro-6,7-dihydro-8-(3-methyl-4-pivaloyloxypiperidin-1-yl)-5-methyl-1-oxo-1H,5H-benzo[i,j]quinolizine-2-carboxylic Acid Pivaloyl chloride (0.0128 ml, 1.06 mmole) was added to a stirred solution of S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid (0.2 g, 0.534 mmole) in pyridine (3 ml) at 0° C. The reaction mixture was stirred at room temperature for 4 hr, concentrated in vacuum to dryness, and triturated with water (20 ml). The solid thus separated was filtered, washed with water (10 ml) and dried to give crude product, which was purified by preparative HPLC. Yield 0.15 g (60%), m.p. 120–22° C., $[\alpha]_D^{25}$ −211° C. (c=1%, methanol solution), $C_{25}H_{31}FN_2O_5$, m/z 459 (M+1), PMR (CDCl$_3$): 1.01 (3H, d, CH$_3$, J=7 Hz), 1.28 (9H, s, 3×CH$_3$), 1.58 (3H, d, CH$_3$, J=7 Hz), 1.94–2.32 (4H, m, H$_{5'}$ & H$_6$), 2.76–3.51(6H, m, H$_{2'}$, H$_{6'}$, H$_7$), 4.58 (1H, m, H$_5$), 4.8 (1H, m, H$_{3'}$), 5.12 (1H, m, H$_{4'}$), 8.06 (1H, d, H$_{10}$, J=17 Hz), 8.76 (1H, s, H$_3$), 15.02 (1H, bs, COOH, D$_2$O exchangeable).

EXAMPLE 41

S-(−)-9-fluoro-6,7-dihydro-8-(3-ethyl-4-pivaloyloxypiperidin-1-yl)-5-methyl-1-oxo-1H, 5H-benzo[i,j]quinolizine-2-carboxylic Acid It was prepared in a similar manner as described Example 40, where S-(−)-9-fluoro-6,7-dihydro-8-(3-ethyl-4-hydroxypiperidin-1-yl)-5-methyl-1-oxo-1H,5H-benzo[i,j]quinolizine-2-carboxylic acid was used in place of S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid. The obtained crude product was purified by preparative HPLC. Yield 0.105 g (36%), m.p.156–58° C., $[\alpha]_D^{25}$–186.5° C. (c=1%, methanol solution), $C_{26}H_{33}FN_2O_5$, m/z 473 (M+1), PMR (CDCl$_3$): 0.98 (3H, d, CH$_3$, J=7 Hz), 1.28 (9H, s, 3×CH$_3$), 1.58 (3H, d, CH$_3$, J=7 Hz), 1.6–2.3 (6H, m, H$_{5'}$, H$_6$ & CH$_2$), 2.78–3.48 (6H, m, H$_{2'}$, H$_{6'}$, H$_7$), 4.56 (1H, m, H$_5$), 4.7 (1H, m, H$_{3'}$), 5.2 (1 H, m, H$_{4'}$), 8.02 (1H, d, H$_{10}$, J=17 Hz), 8.72 (1H, s, H$_3$), 15.12 (1H, bs, COOH, D$_2$O exchangeable).

EXAMPLE 42

S-(−)-9-fluoro-6,7-dihydro-8-(3,3-dimethyl-4-pivaloyloxypiperidin-1-yl)-5-methyl-1-oxo-1H,5H-benzo[i,j]quinolizine-2-carboxylic Acid It was prepared in a similar manner as described Example 40, where S-(−)-9-fluoro-6,7-dihydro-8-(3,3-dimethyl-4-hydroxypiperidin-1-yl)-5-methyl-1-oxo-1H,5H-benzo[i,j]quinolizine-2-carboxylic acid was used in place of S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid. Yield 0.52 g (66%), m.p. 215–17° C., $C_{26}H_{33}FN_2O_5$, m/z 473 (M+1), PMR (CDCl$_3$): 1.02 (6H, 2s, 2×CH$_3$), 1.28 (9H, s, 3×CH$_3$), 1.54 (3H, d, CH$_3$, J=7 Hz), 1.8–2.38 (4H, m, H$_{5'}$ & H$_6$), 2.72–3.52 (6H, m, H$_{2'}$, H$_{6'}$ & H$_7$), 4.6 (1H, m, H$_5$), 4.82 (1H, m, H$_{4'}$), 8.04 (1H, d, H$_{10}$, J=17 Hz), 8.74 (1H, s, H$_3$), 15.02 (1H, bs, COOH, D$_2$O exchangeable).

EXAMPLE 43

S-(−)-9-fluoro-6,7-dihydro-8-(3-ethyl-3-methyl-4-pivaloyloxypiperidin-1-yl)-5-methyl-1-oxo-1H,5H-benzo[i,j]quinolizine-2-carboxylic Acid It was prepared in a similar manner as described Example 40, where S-(−)-9-fluoro-6,7-dihydro-8-(3-ethyl-4-hydroxy-3-methylpiperidin-1-yl)-5-methyl-1-oxo-1H,5H-benzo[i,j]quinolizine-2-carboxylic acid was used in place of S-(−)-9-fluoro-6,7-dihydro-8-(4-hydroxy-3-methyl piperidin-1-yl)-5-methyl-1-oxo-1H,5H-benzo[i,j]quinolizine-2-carboxylic acid. The obtained crude product was purified by preparative HPLC. Yield 0.05 g (50%), m.p. 188–90° C., $C_{27}H_{35}FN_2O_5$, m/z 487 (M+1)

EXAMPLE 44

Pivaloyloxymethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate Powdered anhydrous potassium carbonate (0.055 g, 0.4 mmole) was added to a stirred solution of S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylic acid (0.15 g, 0.4 mmole) in N,N-dimethyl formamide (5 ml) at 50° C. and stirring was continued for 6 hr at 50° C. Chloro methyl pivalate (0.072 g, 0.48 mmole) was added to the resulting mixture and stirring was continued for 18 h at 50° C. The reaction mixture was concentrated, triturated with water, extracted with chloroform to give crude product, which was purified by chromatography. Yield 0.188 g (96%), m.p. 198–200° C., $[\alpha]_D^{25}$–153° (0.1% CHCl$_3$ solution), $C_{26}H_{33}FN_2O_6$, m/z 489 (M+1).

EXAMPLE 45

Acetoxymethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate It was prepared according to procedure described in Example 44, where chloro methyl acetate was used in place of chloro methyl pivalate. Yield 0.128 g (72%), m.p 178–80° C., $[\alpha]_D^{25}$–165° C. (0.1% CHCl$_3$ solution), $C_{23}H_{27}FN_2O_6$, m/z 447 (M+1).

EXAMPLE 46

Carbethoxymethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate It was prepared according to procedure described in example 44, where ethyl bromo acetate was used in place of chloro methyl pivalate Yield 0.141 g (76%), m.p. 168–70° C., $[\alpha]_D^{25}$–186° C. (0.1% CHCl$_3$ solution), $C_{24}H_{29}FN_2O_6$, m/z 461 (M+1).

EXAMPLE 47

2-Morpholino-ethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate 4-N,N-Dimethylamino pyridine (0.061 g, 0.52 mmole), N-2-hydroxyethyl morpholine (0.07 g, 0.53 mmole) and N,N-dicyclohexylcabodiimide (0.086 g, 0.5 mmole) were added sequentially to a solution of S-(−)-9-fluoro-6,7-dihydro-8-{(+)-trans-4-hydroxy-3-methylpiperidin-1-yl}-5-methyl-1-oxo-1H,5H-benzo[i,j]quinolizine-2-carboxylic acid (0.15 g, 0.4 mmole) in a mixture of N,N-dimethyl acetamide (6 ml) and triethyl amine (0.06 ml, 0.6 mmole). The resulting mixture was stirred for 48 h at 100° C. The reaction mixture was diluted with ethyl acetate (50 ml), washed with 0.5N HCl, saturated NaHCO$_3$ solution and water. Ethyl acetate extract was dried (Na$_2$SO$_4$) and concentrated to give crude product, which was purified by chromatography to furnish the required product. Yield 0.065 g (33%), m.p. 205–208° C., $[\alpha]_D^{25}$–154° C. (0.1% CHCl$_3$ solution), $C_{26}H_{34}FN_3O_5$, m/z 488 (M+1).

EXAMPLE 48

2-Piperazino-ethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate It was prepared according to procedure described in Example 47, where N-2-hydroxyethyl piperazine was used in place of N-2-hydroxyethyl morpholine. Yield 0.045 g (23%), m.p. 120–25° C., $[\alpha]_D^{25}$–159° C. (0.1% CHCl$_3$ solution), $C_{26}H_{35}FN_4O_4$, m/z 487 (M+1).

EXAMPLE 49

2-Pyrrolidino-ethyl S-(−)-9-fluoro-6,7-dihydro-8-{trans-4-(RS)-hydroxy-3-(RS)-methyl piperidin-1-yl}-5-methyl-1-oxo-1H,5H-benzo[i,j]quinolizine-2-carboxylate It was prepared according to procedure described in Example 48, where N-2-hydroxyethyl pyrrolidine was used in place of N-2-hydroxyethyl morpholine. Yield 0.128 g (68%), m.p. 170–75° C., $[\alpha]_D^{25}$–128° C. (0.1% CHCl$_3$ solution), C$_{26}$H$_{34}$FN$_3$O$_4$, m/z 472 (M+1).

EXAMPLE 50

4-(N-methyl)-piperidinyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate It was prepared according to procedure described in example 48, where 4-hydroxy-N-methylpiperidine was used in place of 2-hydroxyethyl-N-4-morpholine. Yield 0.132 g (70%), m.p. 208–10° C., $[\alpha]_D^{25}$–157° C. (0.1% CHCl$_3$ solution), C$_{26}$H$_{34}$FN$_3$O$_4$, m/z 472 (M+1).

EXAMPLE 51

S-(−)-9-fluoro-6,7-dihydro-8-(3,3-di-n-propyl-4-hydroxy piperidin-1-yl)-5-methyl-1-oxo-1H,5H-benzo[i,j]quinolizine-2-carboxylic Acid It was prepared in a similar manner as described in example 2, where 3,3-di-n-propyl-4-hydroxy piperidine was used in place of 4-hydroxy-3-methylpiperidine. Yield 0.21 g (77%), m.p. 260–64° C., $[\alpha]_D^{25}$–177° (c=1% methanol solution), C$_{25}$H$_{33}$FN$_2$O$_4$, m/z 445 (M+1).

EXAMPLE 52

S-(−)-9-fluoro-6,7-dihydro-8-(3,3-di-n-butyl-4-hydroxy piperidin-1-yl)-5-methyl-1-oxo-1H,5H-benzo[i,j]quinolizine-2-carboxylic Acid It was prepared in a similar manner as described in Example 2, where 3,3-di-n-butyl-4-hydroxy piperidine was used in place of 4-hydroxy-3-methylpiperidine. Yield 0.165 g (57%), m.p. 288–92° C., $[\alpha]_D^{25}$–137° (c=1% methanol solution), C$_{27}$H$_{37}$FN$_2$O$_4$, m/z 473 (M+1).

EXAMPLE 53

S-(−)-9-fluoro-6,7-dihydro-8-(4-hydroxy-3,3,5-trimethylpiperidin-1-yl)-5-methyl-1-oxo-1H,5H-benzo[i,j]quinolizine-2-carboxylic Acid It was prepared in a similar manner as described in example 2, where 4-hydroxy-3,3,5-trimethyl piperidine was used in place of 4-hydroxy-3-methylpiperidine. Yield 0.035 g (30%), m.p. 178–80° C., C$_{22}$H$_{27}$FN$_2$O$_4$, m/z 403 (M+1).

EXAMPLE 54

S-(−)-9-fluoro-6,7-dihydro-8-(4-hydroxy-3,5-dimethyl-3-ethylpiperidin-1-yl)-5-methyl-1-oxo-1H,5H-benzo[i,j]quinolizine-2-carboxylic Acid It was prepared in a similar manner as described in Example 2, where 4-hydroxy-3,5-dimethyl-3-ethylpiperidine was used in place of 4-hydroxy-3-methylpiperidine. Yield 0.07 g (36%), m.p. 182–84° C., $[\alpha]_D^{25}$–176° (c=1%, methanol solution), C$_{23}$H$_{29}$FN$_2$O$_4$, m/z 417 (M+1).

EXAMPLE 55

S-(−)-9-fluoro-6,7-dihydro-8-(4-hydroxy-3,5-diethyl-3-methylpiperidin-1-yl)-5-methyl-1-oxo-1H,5H-benzo[i,j]quinolizine-2-carboxylic Acid It was prepared in a similar manner as described in example 2, where 4-hydroxy-3,5-diethyl-3-methylpiperidine was used in place of 4-hydroxy-3-methylpiperidine. Yield 0.04 g (40%), m.p. 180–82° C., C$_{24}$H$_{31}$FN$_2$O$_4$, m/z 431 (M+1).

BIOLOGICAL EXAMPLES

Microbiological and pharmacological studies can be used to determine the relative potency, and the profile of specificity of the optically pure compounds of the invention as antibacterial agents with a spectrum of activity as described in the specification above.

BIOLOGICAL EXAMPLE 1

In-vitro Antimicrobial Test

The activity of the compounds of the invention in-vitro can be illustrated as follows:

The comparative antimicrobial activity of the compounds of the invention against various microorganisms is given in Table 1. The test method was in accordance with the standard NCCLS protocol.

TABLE 1

Comparative Mics (μG/Ml) Of The Compounds Of The Invention

| Compound | MIC (μg/ml) | | | | |
| --- | --- | --- | --- | --- | --- |
| @ | MRSA | S. pneumoniae | VRE | E. coli | P. aeruginosa |
| A | 0.4 | 0.2 | 6.25 | 0.2 | 3.12 |
| B | 0.8 | 0.2 | 6.25 | 0.2 | 6.25 |
| C | 0.8 | 0.1 | 6.25 | 0.1 | 6.25 |
| D | 0.8 | 0.8 | 6.25 | 0.2 | 6.25 |
| E | 1.56 | 0.2 | 12.5 | 0.8 | >12.5 |
| Ref. 1 * | 1.56 | 0.4 | 12.5 | 0.4 | 6.25 |
| Ref. 2* | 0.8 | 0.2 | 6.25 | 0.2 | 3.12 |

Compound A

S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylic acid

Compound B

S-(−)-9-fluoro-6,7-dihydro-8-{cis-4-(RS)-hydroxy-3-(RS)-methylpiperidin-1-yl-5-methyl-1-oxo-1H,5H-benzo[i,j]quinolizine-2-carboxylic acid.

Compound C

S-(−)-9-fluoro-6,7-dihydro-8-{cis-(−)-4-R-hydroxy-3-S-methylpiperidin-1-yl}-5-methyl-1-oxo-1H,5H-benzo[i,j]quinolizine-2-carboxylic acid.

Compound D

S-(−)-9-fluoro-6,7-dihydro-8-{cis-(+)-4-S-hydroxy-3-R-methylpiperidin-1-yl}-5-methyl-1-oxo-1H,5H-benzo[i,j]quinolizine-2-carboxylic acid

Compound E

S-(−)-9-fluoro-6,7-dihydro-8-(3-ethyl-4-hydroxypiperidin-1-yl)-5-methyl-1-oxo-1H,5H-benzo[i,j]

quinolizine-2-carboxylic acid (mixture of cis racemate and trans racemate)

Ref. 1=RS(±)-9-fluoro-8-(4'-hydroxypiperidin-1-yl)-5-methyl-6,7-dihydro-1-oxo-1H-5H-benzo[i,j]quinolizine-2-carboxylic acid

*Ref. 2=S-(−)-9-fluoro-8-(4'-hydroxypiperidin-1-yl)-5-methyl-6,7-dihydro-1-oxo-1H-5H-benzo[i,j]quinolizine-2-carboxylic acid The compounds of the invention show superior potency in comparison to RS(±)-9-fluoro-8-(4'-hydroxypiperidin-1-yl)-5-methyl-6,7-dihydro-1-oxo-1H-5H-benzo[i,j]quinolizine-2-carboxylic acid and S-(−)-9-fluoro-8-(4'-hydroxypiperidin-1-yl)-5-methyl-6,7-dihydro-1-oxo-1H-5H-benzo[i,j]quinolizine-2-carboxylic acid.

BIOLOGICAL EXAMPLE 2

Comparison of a typical compound of the invention vs S-(−)-9-fluoro-8-(4'-hydroxypiperidin-1-yl)-5-methyl-6,7-dihydro-1-oxo-1H-5H-benzo[i,j]quinolizine-2-carboxylic acid in terms of % Killing of Streptococci

TABLE 2

|  | 4 MIC-% Kill at 8 hrs. | |
| --- | --- | --- |
|  | Ref. 2* | Typical compound of the invention** |
| S. salivarius ATCC 13419 | 0 | 99.7 |
| S. pyogenes ATCC 25147 | 45.4 | 98.4 |
| S. sanguis ATCC 10556 | 40 | 98.6 |
| S. pneumoniae ATCC 6303 | 50 | 99.8 |

*For Ref. 2 cf. above
**A typical compound of the invention is S-(-)-9-fluoro-6,7-dihydro-8-(4-hydroxy-3-methylpiperidin-1-yl)-5-methyl-1-oxo-1H,5H-benzo[i,j] quinolizine-2-carboxylic acid (mixture of cis racemate and trans racemate).

As seen in the table, depending upon the streptococcal strain under consideration, S-(−)-9-fluoro-8-(4'-hydroxypiperidin-1-yl)-5-methyl-6,7-dihydro-1-oxo-1H-5H-benzo[i,j]quinolizine-2-carboxylic acid either fails to kill (0%) or at best kills only 50% of the population when exposed to 4×MIC concentrations for 8 hours. As against this, a typical compound of the invention, which has an improved bactericidal power againt streptococci, consistently brings about killing of 99% of streptococcal population.

What is claimed is:
1. A compound of formula I

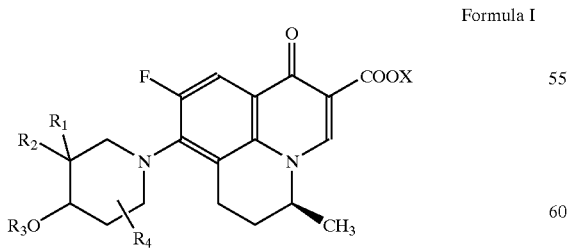

Formula I

X is hydrogen, X is $C_1$–$C_{20}$ alkyl, aralkyl, —$(CH_2)$n—$CHR_{10}$—$OCOR_{11}$, or $(CH_2)_n$—$CHR_{10}$—$OCO_2R_{11}$ wherein $R_{10}$ is H, or $CH_3$; n is 0–3 and $R_{11}$ is $C_1$–$C_{20}$ alkyl or substituted $C_1$–$C_6$ alkyl, or aralkyl or $R_{11}$ is

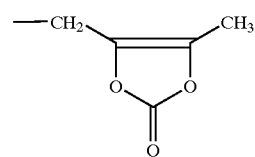

or X is acetoxymethyl, acetoxyethyl, carbethoxymethyl, pivaloyloxymethyl, or pivaloyloxyethyl group;
or X is heterocyclic amino or heterocyclic aminoalkyl of the formula

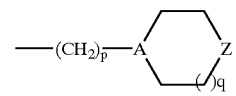

wherein A is CH or N, and when A is CH, Z is NH or $NCH_3$, and when A is N, Z is $CH_2$, O, NH, S, or $NCH_3$; p is 0–2; and q is 0–2;

$R_1$ is hydrogen, $C_{1-4}$ alkyl, aralkyl, aminoalkyl, trifluoroalkyl, or halogen, $R_2$ is hydrogen, $C_{1-4}$ alkyl, aralkyl, aminoalkyl, trifluoroalkyl, or halogen with the proviso that when $R_1$ is hydrogen $R_2$ is not hydrogen;

$R_3$ is hydrogen, $C_1$–$C_{20}$ alkyl, glycosyl, aralkyl, $C_1$–$C_6$ alkanoyl; or aminoalkanoyl derived from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine, or the optically active isomers thereof, or the racemic mixtures thereof, or 1-aminocyclohexylcarbonyl or $COOR_{11}$ wherein $R_{11}$ is as defined above, or —$(CH_2)_n$—$CHR_{10}$—$OCOR_{11}$ or —$(CH_2)_n$—$CHR_{10}$—$OCOOR_{11}$ where n, $R_{10}$ and $R_{11}$ are as defined above, or $C_6H_{11}O_6$, $PO_2(CH_3)H$, $PO_3H_2$, $PO_2(OCH_3)H$ or $SO_3H$, provided that $R_1$, $R_2$ and $R_3$ are not equal to H at the same time;

$R_4$ is H, $C_{1-4}$ alkyl, $CF_3$, phenyl, F, substituted at one or more of the positions of 2-, 4-, 5-, or 6- of the piperidine ring, or an optical isomer, diastereomer or enantiomer thereof, or polymorph or pseudopolymorph or prodrug thereof or pharmaceutically acceptable salt or hydrate thereof.

2. A compound according to claim 1, wherein:
X is acetoxymethyl, carbethoxymethyl, pivaloyloxymethyl, 2-piperazinoethyl, 2-morpholinoethyl, 2-pyrrolidinoethyl, or 4-N-methyl piperidinyl;

$R_1$ is $CH_3$, $C_2H_5$, n-$C_3H_7$, i-$C_3H_7$, n-$C_4H_9$, i-$C_4H_9$, $CF_3$, $CH_2C_6H_5$, $CH_2NH_2$, or F;

$R_2$ is H, $CH_3$, $C_2H_5$, n-$C_3H_7$, or n-$C_4H_9$;

$R_3$ is H, $CH_3$, $C_2H_5$, $COCH_3$, or $COC(CH_3)_3$; and $R_4$ is H, 5-$CH_3$, 5-$C_2H_5$, 4-$CH_3$, 4-$CF_3$, or 4-$C_6H_5$; or an optical isomer, diastereomer or enantiomer thereof, or polymorph or pseudopolymorph, or prodrug thereof or pharmaceutically acceptable salt or hydrate thereof.

3. A compound selected from the group consisting of
S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-(4-hydroxy-3-methylpiperidin-1-yl)-5-methyl-1-oxo-1H,5H-benzo[i, j]quinolizine-2-carboxylic acid sodium salt (mixture of cis racemate and trans racemate);

S-(−)-9-fluoro-6,7-dihydro-8-(4-methoxy-3-methylpiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-(4-ethoxy-3-methylpiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-(4-acetoxy-3-methylpiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-(3-methyl-4-pivaloyloxypiperidin-1-yl)-5-methyl-1-oxo-1H,5H-benzo[i,j]quinolizine-2-carboxylic acid (mixture of cis racemate and trans racemate);

S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylic acid, optical isomers, prodrugs and salts thereof;

S-(−)-9-fluoro-6,7-dihydro-8-{trans-(−)-4-R-hydroxy-3-R-methylpiperidin-1-yl}-5-methyl-1-oxo-1H,5H-benzo[i,j]quinolizine-2-carboxylic acid;

S-(−)-9-fluoro-6,7-dihydro-8-{trans-(−)-4-R-hydroxy-3-R-methylpiperidin-1-yl}-5-methyl-1-oxo-1H,5H-benzo[i,j]quinolizine-2-carboxylic acid arginine salt;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid arginine salt;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid histidine salt;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid lysine salt;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid arginine methyl ester salt;

S-(−)-9-fluoro-6,7-dihydro-8-{trans-(+)-4-S-hydroxy-3-S-methylpiperidin-1-yl}-5-methyl-1-oxo-1H,5H-benzo[i,j]quinolizine-2-carboxylic acid histidine methyl ester salt;

S-(−)-9-fluoro-6,7-dihydro-8-{cis-4-(RS)-hydroxy-3-(RS)-methylpiperidin-1-yl-5-methyl-1-oxo-1H,5H-benzo[i,j]quinolizine-2-carboxylic acid, optical isomers, prodrugs and salts thereof;

S-(−)-9-fluoro-6,7-dihydro-8-{cis-(−)-4-R-hydroxy-3-S-methylpiperidin-1-yl}-5-methyl-1-oxo-1H,5H-benzo[i,j]quinolizine-2-carboxylic acid, prodrugs and salts thereof;

S-(−)-9-fluoro-6,7-dihydro-8-{cis-(+)-4-S-hydroxy-3-R-methylpiperidin-1-yl}-5-methyl-1-oxo-1H,5H-benzo[i,j]quinolizine-2-carboxylic acid, prodrugs and salts thereof;

S-(−)-9-fluoro-6,7-dihydro-8-(4-hydroxy-3-trifluoromethylpiperidin-1-yl)-5-methyl-1-oxo-1H,5H-benzo[i,j]quinolizine-2-carboxylic acid and its optical isomers (mixture of cis racemate and trans racemate);

S-(−)-9-fluoro-6,7-dihydro-8-(3,3-dimethyl-4-hydroxypiperidin-1-yl)-5-methyl-1-oxo-1H,5H-benzo[i,j]quinolizine-2-carboxylic acid and its optical isomers;

S-(−)-9-fluoro-6,7-dihydro-8-(4-acetoxy-3,3-dimethylpiperidin-1-yl)-5-methyl-1-oxo-1H,5H-benzo[i,j]quinolizine-2-carboxylic acid and its optical isomers;

S-(−)-9-fluoro-6,7-dihydro-8-(3,3-dimethyl-4-pivaloyloxypiperidin-1-yl)-5-methyl-1-oxo-1H,5H-benzo[i,j]quinolizine-2-carboxylic acid and its optical isomers;

S-(−)-9-fluoro-6,7-dihydro-8-(3ethyl-4-hydroxypiperidin-1-yl)-5-methyl-1-oxo-1H,5H-benzo[i,j]quinolizine-2-carboxylic acid (mixture of cis racemate and trans racemate) and its optical isomers;

S-(−)-9-fluoro-6,7-dihydro-8-(4-acetoxy-3-ethylpiperidin-1-yl)-5-methyl-1-oxo-1H,5H-benzo[i,j]quinolizine-2-carboxylic acid mixture of cis racemate and trans racemate and its optical isomers;

S-(−)-9-fluoro-6,7-dihydro-8-(3-ethyl-4-pivaloyloxypiperidin-1-yl)-5-methyl-1-oxo-1H,5H-benzo[i,j]quinolizine-2-carboxylic acid and its optical isomers;

S-(−)-9-fluoro-6,7-dihydro-8-(3,3-diethyl-4-hydroxypiperidin-1-yl)-5-methyl-1-oxo-1H,5H-benzo[i,j]quinolizine-2-carboxylic acid and its optical isomers;

S-(−)-9-fluoro-6,7-dihydro-8-(3-ethyl-4-hydroxy-3-methylpiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(4-acetoxy-3-ethyl-3-methylpiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3-ethyl-4-pivaloyloxy-3-methylpiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3,5-dimethyl-4-hydroxypiperidin-1-yl)-5-methyl-1-oxo-1H,5H-benzo[i,j]quinolizine-2-carboxylic acid (mixture of cis racemate and trans racemate); and its optical isomers;

S-(−)-9-fluoro-6,7-dihydro-8-(trans-3,5-dimethyl-4-hydroxypiperidin-1-yl)-5-methyl-1-oxo-1H,5H-benzo[i,j]quinolizine-2-carboxylic acid, optical isomers, prodrugs and salts thereof;

S-(−)-9-fluoro-6,7-dihydro-8-(cis-3,5-dimethyl-4-hydroxypiperidin-1-yl)-5-methyl-1-oxo-1H,5H-benzo[i,j]quinolizine-2-carboxylic acid, optical isomers, salts and prodrugs thereof;

S-(−)-9-fluoro-6,7-dihydro-8-(4-hydroxy-3-n-propylpiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3,3-di-n-propyl-4-hydroxypiperidin-1-yl)-5-methyl-1-oxo-1H,5H-benzo[i,j]quinolizine-2-carboxylic acid and its optical isomers;

S-(−)-9-fluoro-6,7-dihydro-8-(4-hydroxy-3-isopropylpiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3-n-butyl-4-hydroxypiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3,3-di-n-butyl-4-hydroxypiperidin-1-yl)-5-methyl-1-oxo-1H,5H-benzo[i,j]quinolizine-2-carboxylic acid and its optical isomers;

S-(−)-9-fluoro-6,7-dihydro-8-(4-hydroxy-3-isobutylpiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3-benzyl-4-hydroxypiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(4-hydroxy-4-methylpiperidin-1-yl)-5-methyl-1-oxo-1H,5H-benzo[i,j]quinolizine-2-carboxylic acid;

S-(−)-9-fluoro-6,7-dihydro-8-(4-hydroxy-4-trifluoromethylpiperidin-1-yl)-5-methyl-1-oxo-1H,5H-benzo[i,j]quinolizine-2-carboxylic acid;

S-(−)-9-fluoro-6,7-dihydro-8-(4-hydroxy-4-phenylpiperidin-1-yl)-5-methyl-1-oxo-1H,5H-benzo[i,j]quinolizine-2-carboxylic acid;

S-(−)-9-fluoro-6,7-dihydro-8-(4-hydroxy-3-methyl-4-trifluoromethyl piperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3-fluoro-4-hydroxypiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3-aminomethyl-4-hydroxypiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(4-hydroxy-3,3,5-trimethylpiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3,5-dimethyl-3-ethyl-4-hydroxypiperidin-1-yl)-5-methyl-1-oxo-1H,5H-benzo[i,j]quinolizine-2-carboxylic acid, its diastereomers and its optical isomers;

S-(−)-9-fluoro-6,7-dihydro-8-(3,5-diethyl-4-hydroxy-3-methylpiperidin-1-yl)-5-methyl-1-oxo-1H,5H-benzo[i,j]quinolizine-2-carboxylic acid, its diastereomers and its optical isomers;

Pivaloyloxymethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

Acetoxymethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

Carbethoxymethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

2-Piperazino-ethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

2-Morpholino-ethyl S-(−)-9-fluoro-6,7-dihydro-8-{trans-4-(RS)-hydroxy-3-(RS)-methylpiperidin-1-yl}-5-methyl-1-oxo-1H,5H-benzo[i,j]quinolizine-2-carboxylate;

2-Pyrrolidino-ethyl S-(−)-9-fluoro-6,7-dihydro-8-{trans-4-(RS)-hydroxy-3-(RS)-methyl piperidin-1-yl)-5-methyl-1-oxo-1H,5H-benzo[i,j]quinolizine-2-carboxylate; or 4-(N-methyl)-piperidinyl S-(−)-9-fluoro-6,7-dihydro-8-{trans-4-(RS)-hydroxy-3-(RS)-methyl piperidin-1-yl}-5-methyl-1-oxo-1H,5H-benzo[i,j]quinolizine-2-carboxylate.

4. A method for preparing S-(−)-9-fluoro-6,7-dihydro-8-(3-, 4-substituted-4-hydroxypiperidin-1-yl)-5-methyl-1-oxo-1H,5H-benzo[i,j]quinolizine-2-carboxylic acid according to claim 1 comprising the steps of heating a mixture of (O-B)-diacetoxy-{S-(−)-8,9-difluoro-5-methyl-6,7-dihydro-5-methyl-1-oxo-1H,5H-benzo[i,j]quinolizine-2-carboxy}borane and 3-, 4-substituted-4-hydroxypiperidine in an organic solvent, optionally in the presence of a base at 50°–120° C. for 4–24 hr.

5. A method for preparing S-(−)-9-fluoro-6,7-dihydro-8-(3-, 4-, 5-substituted-4-hydroxypiperidin-1-yl)-5-methyl-1-oxo-1H,5H-benzo[i,j]quinolizine-2-carboxylic acid according to claim 1 comprising the steps of heating a mixture of (O-B)-diacetoxy-{S-(−)-8,9-difluoro-5-methyl-6,7-dihydro-5-methyl-1-oxo-1H,5H-benzo[i,j]quinolizine-2-carboxy}borane and 3-, 4-, 5-substituted-4-hydroxypiperidine in an organic solvent, optionally in the presence of a base at 50°–120° C. for 4–24 hr.

6. A method for preparing S-(−)-9-fluoro-6,7-dihydro-8-(3-, 4-substituted-4-alkanoyloxypiperidin-1-yl)-5-methyl-1-oxo-1H,5H-benzo[i,j]quinolizine-2-carboxylic acid according to claim 1 comprising the steps of stirring a mixture of S-(−)-9-fluoro-6,7-dihydro-8-(3-, 4-substituted-4-hydroxypiperidin-1-yl)-5-methyl-1-oxo-1H,5H-benzo[i,j]quinolizine-2-carboxylic acid with an alkanoylating agent in presence of a base in the presence or absence of an organic solvent at 0°–100° C. for 0.5–8 hr.

7. A method for preparing S-(−)-9-fluoro-6,7-dihydro-8-(3-, 4-, 5-substituted-4-alkanoyloxypiperidin-1-yl)-5-methyl-1-oxo-1H,5H-benzo[i,j]quinolizine-2-carboxylic acid according to claim 1 comprising the steps of stirring a mixture of S-(−)-9-fluoro-6,7-dihydro-8-(3-, 4-, 5-substituted-4-hydroxypiperidin-1-yl)-5-methyl-1-oxo-1H,5H-benzo[i,j]quinolizine-2-carboxylic acid with an alkanoylating agent in presence of a base in the presence or absence of an organic solvent at 0°–100° C. for 0.5–8 hr.

8. A method for preparing alkanoyloxymethyl S-(−)-9-fluoro-6,7-dihydro-8-(trans 4-hydroxy-3-methylpiperidin-1-yl)-5-methyl-1-oxo-1H,5H-benzo[i,j]quinolizine-2-carboxylate according to claim 1 comprising the steps of treating S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid with halomethyl alkanoate in presence of a base in the presence or absence of an organic solvent at 0°–100° C. for 2–24 hr.

9. A method for preparing heterocyclic amino or heterocyclic aminoalkyl S-(−)-9-fluoro-6,7-dihydro-8-{trans-4-hydroxy-3-methylpiperidin-1-yl)-5-methyl-1-oxo-1H,5H-benzo[i,j]quinolizine-2-carboxylate according to claim 1 comprising the steps of treating S-(−)-9-fluoro-6,7-dihydro-8-(4-hydroxy-3-methylpiperidin-1-yl)-5-methyl-1-oxo-1H,5H-benzo[i,j]quinolizine-2-carboxylic acid with hydroxy heteroyclic amine or hydroxy alkyl heterocyclic amine in presence of a base in the presence or absence of an organic solvent at 50°–100° C. for 2–48 hr.

10. A composition comprising a compound according to claim 1 and an excipient, diluent, solvent or carrier.

11. A composition comprising a compound according to claim 2 and an excipient, diluent, solvent or carrier.

12. A composition comprising a compound according to claim 3 and an excipient, diluent, solvent or carrier.

13. A method for treating an infection caused by gram-positive organisms, gram-negative organisms, mycobacteria or nosocomial pathogens comprising administering an effective amount of a compound according to claim 1 to a patient in need thereof.

14. A method for treating an infection caused by gram-positive organisms, gram-negative organisms, mycobacteria or nosocomial pathogens comprising administering an effective amount of a compound according to claim 2 to a patient in need thereof.

15. A method for treating an infection caused by gram-positive organisms, gram-negative organisms, mycobacteria or nosocomial pathogens comprising administering an effective amount of a compound according to claim 3 to a patient in need thereof.

* * * * *